United States Patent
Skelly et al.

(10) Patent No.: US 11,348,670 B2
(45) Date of Patent: May 31, 2022

(54) METHODS FOR TREATING ERECTILE DYSFUNCTION WITH A CGMP-SPECIFIC PHOSPHODIESTERASE 5 INHIBITOR PHARMACEUTICAL COMPOSITION

(71) Applicant: AstraZeneca UK Limited, Cambridge (GB)

(72) Inventors: Richard L. Skelly, Flourtown, PA (US); Judy Firor, Landenberg, PA (US)

(73) Assignee: ASTRAZENECA UK LIMITED, Cambridge (GB)

( * ) Notice: Subject to any disclaimer, the term of this patent is extended or adjusted under 35 U.S.C. 154(b) by 308 days.

(21) Appl. No.: 16/440,811

(22) Filed: Jun. 13, 2019

(65) Prior Publication Data
US 2019/0385719 A1 Dec. 19, 2019

Related U.S. Application Data

(60) Provisional application No. 62/685,230, filed on Jun. 14, 2018.

(51) Int. Cl.
| | | |
|---|---|---|
| *G16H 20/10* | (2018.01) | |
| *A61P 15/10* | (2006.01) | |
| *G16H 50/70* | (2018.01) | |
| *G16H 10/20* | (2018.01) | |
| *A61K 31/4985* | (2006.01) | |
| *A61K 31/53* | (2006.01) | |
| *G16H 50/30* | (2018.01) | |

(52) U.S. Cl.
CPC .......... *G16H 20/10* (2018.01); *A61K 31/4985* (2013.01); *A61K 31/53* (2013.01); *A61P 15/10* (2018.01); *G16H 10/20* (2018.01); *G16H 50/30* (2018.01); *G16H 50/70* (2018.01)

(58) Field of Classification Search
CPC ........ G16H 20/10; G16H 50/30; G16H 50/70; G16H 10/20; A61P 15/10; A61K 31/4985; A61K 31/53
See application file for complete search history.

(56) References Cited

U.S. PATENT DOCUMENTS

| | | |
|---|---|---|
| 7,493,264 B1 | 2/2009 | Kelly et al. |
| 2005/0108053 A1 | 5/2005 | Jones |
| 2009/0125324 A1 | 5/2009 | Keravich et al. |
| 2011/0166876 A1 | 7/2011 | Chapman |
| 2011/0178812 A1 | 7/2011 | Lindsay |

FOREIGN PATENT DOCUMENTS

WO    WO 2010/041052 A1    4/2010

OTHER PUBLICATIONS

International Search Report and Written Opinion for International Patent Application No. PCT/US2019/037091, dated Dec. 3, 2019, 26 pages.

Pfizer: Viagra Connect Checklist: Viagra Connect HPC, Mar. 31, 2018, [online], [retrieved on Sep. 19, 2019], Retrieved from the Internet: <URL: https://hpc.viagraconnect.co.uk/viagra-connect-checklist>.

Pfizer: Viagra Connect Pharmacy Checklist, Mar. 31, 2018, [online], [retrieved on Sep. 19, 2019], Retrieved from the Internet: <URL: https://hpc.viagraconnect.co.uk/sites/default/files/2018-01/Viagra%20Connect%20Checklist_0.pdf>.

Moss, How to Get Over the Counter Viagra Without a Prescription, Plus Dosage and Side Effects Explained: Huffpost Life:, Mar. 27, 2018, [online], [retrieved on Sep. 19, 2019], Retrieved from the Internet: <URL: https://www.huffingtonpost.co.uk/entry/how-to-get-over-the-counter-viagra-without-a-prescription-plus-dosage-and-side-effects-explained_uk_ 5aba0606e4b008c9e5fae9d9?guccounter=1&guce_referrer=aHROcHM6Ly93d3cuZ29vZ2xlLmNvbS8&guce_referrer_sig=AQAAAEaxmX05B9rZXpRTySOWvbAZTMbLbFctVHTQkbDVtivNeB75MIDsJw>.

Basford, "Buying Over the Counter Viagra—UK | Zava", Oct. 14, 2018, [online], [retrieved on Sep. 9, 2019], Retrieved from the Internet: <URL: https://zavamed.com/uk/over-the-counter-viagra.html>.

Korkmaz-Icoz et al., "Targeting phosphodiesterase 5 as a therapeutic option against myocardial ischaemia / reperfusion injury and for treating heart failure : PDE5 and myocardial protection", British Journal of Pharmacology, vol. 175, No. 2, Jan. 1, 2018.

Anonymous, "Cialis Over the Counter from USA—Get Cialis without a Doctor Prescription", Oct. 10, 2017, [online], [retrieved on Sep. 19, 2019], Retrieved from the Internet: <URL: http://cialisoverthecounterusa.com>.

Ramkumar, S. et al., Acta Cardiol. Sin., 32(6):631-39 (2016).

Barias S. FDA Considers a New Paradigm for Over-the-Counter Medications: More Power—but More Burdens—for Pharmacists and Pharmacies. P T. May 2012;37(5):300-5. PubMed PMID: 22876088; PubMed Central PMCID: PMC3411219.

Crestor, Full Prescribing Information, 2012, AstraZeneca Pharmaceuticals LP.

Dyer O., "FDA Rejects sale of over the counter Statins", BMJ, Jan. 22, 2005; 330(7484):164.

May 9, 2013, power point presentations from the Engelberg Center for Health Care Reform.

Pfizer Wants Atorvastatin Available Over the Counter—Medscape—Aug. 4, 2011, downloaded from the Internet Nov. 30, 2018.

PR Newswire Association, "Americans Should Pay More Attention to Over-the-Counter (OTC) medicine Labels According to New Survey", Oct. 15, 2015 (citing McNeil Consumer Healthcare research).

Cialis (tadalafil) Prescribing Information, (Eli Lilly) Oct. 2011, [online], [retrieved on Feb. 28, 2021], Retrieved from the Internet: <URL: https://www.accessdata.fda.gov/drugsatfda_docs/label/2011/021368s20s21 lbl.pdf>.

(Continued)

*Primary Examiner* — Jerry Lin

(74) *Attorney, Agent, or Firm* — Brett A. Lovejoy; Andrew J. Antczak; Morgan, Lewis & Bockius LLP

(57) ABSTRACT

A method is provided for treating erectile dysfunction in a subject in need thereof by administering a cGMP-specific phosphodiesterase 5 ($PDE_5$) inhibitor pharmaceutical composition to a subject qualified for over-the-counter access to the $PDE_5$ inhibitor pharmaceutical composition. In some embodiments, the $PDE_5$ inhibitor pharmaceutical composition includes tadalafil or vardenafil.

48 Claims, 27 Drawing Sheets

(56) References Cited

OTHER PUBLICATIONS

Levitra (vardenafil hydrochloride) Prescribing Information, (Bayer) Apr. 2014, [online], [retrieved on Feb. 28, 2021], Retrieved from the Internet: <URL: https://www.accessdata.fda.gov/drugsatfda_docs/label/2014/021400s017lbl.pdf>.

Viagra (sildenafil citrate) Prescribing Information, (Pfizer) Mar. 2014, [online], [retrieved on Feb. 28, 2021], Retrieved from the Internet: <URL: https://www.accessdata.fda.gov/drugsatfda_docs/label/2014/20895s039s042lbl.pdf>.

Bell et al., Prescribing patterns and costs associated with erectile dysfunction drugs in England: a time trend analysis. BJGP Open—Research, 8 pgs (2021).

Both et al., Analysis of licensed over-the-counter (OTC) antibiotics in the European Union and Norway. Euro Surveill (2015).

Chang et al., Prescription to over-the-counter switches in the United States. Journal of Research in Pharmacy Practice. (2016).

Ferris et al., Over-the-Counter Antifungal Drug Misuse Associated With Patient-Diagnosed Vulvovaginal Candidiasis. Antifungal Drug Misuse. Obstetrics & Gynecology. vol. 99, No. 3, (2002) The American College of Obstetricians and Gynecologists.

GoDaddy.com—WHOIS Database, "cialisoverthecounterusa.com" (5 pgs) (2021).

Gov.Uk, Guidance—Medicines: reclassify your product. https://www.gov.uk/guidance/mediciries-reclassify-your-product#prescription-only-medicine-pom-to-pharmacy-p-medicine 11 pgs (2021).

Pharmacyinfocus.com: pharmacyinfocus.co.uk/viagra-connect-sildenafil-granted-reclassification-uk-mhra-non-prescription-pharmacysupplied-treatment-erectile-dysfunction-men-aged-18. Viagra Connect (sildenafil) granted reclassification by the UK MHRA. (Nov. 28, 2017), 3 pgs.

Ruiz, M., Risk of self-medication practices. Current Drug Safety, 5(4):315, 27 pgs (2010).

Sharlip, I., Is There a Space to Improve the Treatment of Erectile Dysfunction in the Next Years? Difference of Opinion. Vol. 41 (5): 832-834, Sep.- Oct. 2015, 3 pgs.

Stomberg et al., Utilization effects of Rx-OTC switches and implications for future switches. Health. vol. 5, No. 10, 1667-1680 (2013).

Yuen and Chong, Rx-to-OTC Switch—An Overview and its Implications to Public Health. Pharmacy Education & Practice. vol. 25, No. 4 (2018).

| | |
|---|---|
| Reassessment module | 254 |
| First filter category class | 214-2 |
| Erectile dysfunction filter | 216-7 |
| Vasodilator filter | 216-8 |
| Guanylate cyclase stimulator filter | 216-9 |
| PDE$_5$ inhibitor filter | 216-10 |
| Sexual intercourse filter | 216-11 |
| Priapism filter | 216-12 |
| Sensory deterioration filter | 216-13 |
| ⋮ | |
| Filter W | 222-W |
| Second filter category class | 220-2 |
| Heart problem filter | 222-14 |
| Blood pressure filter | 222-15 |
| Stroke filter | 222-16 |
| Liver disease filter | 222-17 |
| Kidney disease filter | 222-18 |
| Retinitis pigmentosa filter | 222-19 |
| Stomach ulcer filter | 222-20 |
| Bleeding problem filter | 222-21 |
| Genital abnormality filter | 222-22 |
| Blood cell disorder filter | 222-23 |
| Drug interaction filter | 222-24 |
| ⋮ | |
| Filter Z | 222-Z |
| Adverse event module | 242 |

(402) A computer system for qualifying a human subject for over-the-counter delivery of a cGMP-specific phosphodiesterase 5 (PDE$_5$) inhibitor pharmaceutical composition for treating erectile dysfunction. The computer system comprises one or more processors and a memory. The memory comprises non-transitory instructions which, when executed by the one or more processor, perform a method.

(404) The PDE$_5$ inhibitor pharmaceutical composition has a structure of structure (I).

(406) The PDE$_5$ inhibitor pharmaceutical composition includes tadalafil or a pharmaceutically acceptable salt thereof.

(408) The dihydropyridine-type calcium channel blocker pharmaceutical composition includes vardenafil.

(410) Conduct a first survey of the subject thereby obtaining a first plurality of survey results.

(412) The first plurality of survey results comprise a gender of the subject, an age of the subject, an erectile dysfunction status of the subject, whether the subject is taking a nitrate or nitrite vasodilator composition, whether the subject is taking a guanylate cyclase stimulator medication, whether the subject is taking a PDE$_5$ inhibitor composition, whether the subject has ever had a heart problem, a blood pressure status of the subject, whether the subject has ever had a stroke, whether the subject has a liver problem, a kidney function status of the subject, whether the subject has retinitis pigmentosa, whether the subject has experienced vision loss, whether the subject has ever had a stomach ulcer, whether the subject has a bleeding disorder, a genital status of the subject, whether the subject has ever experienced priapism, whether the subject has a blood cell disorder, and whether the subject is taking a medication that interaction with the PDE$_5$ inhibitor pharmaceutical composition.

(414) Run all or a portion of the first plurality of survey results against a first plurality of filters of a first category class. When a respective filter in the first plurality of filters is fired, the subject is deemed not qualified for delivery of the PDE$_5$ inhibitor pharmaceutical composition and the method is terminated without delivery of the PDE$_5$ inhibitor pharmaceutical composition to the subject.

(416) The first plurality of filters comprises a gender filter that is fired when the first plurality of survey results indicates that the subject is female.

(418) The first plurality of filters comprises an age filter.

(420) The age filter is fired when the first plurality of survey results indicates that the subject is less than eighteen years old.

(422) The first plurality of filters comprises a first erectile dysfunction filter that is fired at least when the first plurality of survey results indicates that the subject does not have erectile dysfunction.

(424) The first plurality of filters comprises a first vasodilator filter that is fired at least when the first plurality of survey results indicates that the subject is taking a vasodilator composition comprising a nitrate or a nitrite.

(426) The vasodilator composition, which is capable of firing the first vasodilator filter, includes a compound selected from the group consisting of nitroglycerin, amyl nitrate, amyl nitrite, and butyl nitrate.

(430) The first plurality of filters comprises a first guanylate cyclase stimulator filter that is fired at least when the first plurality of survey results indicates that the subject is taking a guanylate cyclase stimulator mediation.

(428) The first plurality of filters comprises a first PDE$_5$ inhibitor filter that is fired at least when the first plurality of survey results indicates that the subject is taking a PDE$_5$ inhibitor composition.

Fig. 4B

(432) Run all or a portion of the first plurality of survey results against a second plurality of filters of a second category class. When a respective filter in the second plurality of filters is fired, the subject is provided with a warning corresponding to the respective filter.

(434) The second plurality of filters comprises a first heart problem filter that is fired at least when the first plurality of survey results indicates that the subject has had a heart problem.

(436) The heart problem, which is capable of firing the first heart problem filter, is selected from the group consisting of a heart attack, arrhythmia, angina, chest pain, narrowing of the aortic valve, and heart failure.

(438) The second plurality of filters comprises a first blood pressure filter that this fired at least when the first plurality of survey results indicates that the subject has either low blood pressure, or uncontrolled high blood pressure.

(440) The second plurality of filters comprises a first stroke filter that is fired at least when the first plurality of survey results indicates that the subject has had a stroke.

(442) The second plurality of filters comprises a first liver disease filter that is fired at least when the first plurality of survey results indicates that the subject has a liver problem.

(444) The second plurality of filters comprises a first kidney disease filter that is fired at least when the first plurality of survey results indicates that the subject has a kidney problem.

(446) The second plurality of filters comprises a first retinitis pigmentosa filter that is fired at least when the first plurality of survey results indicates that the subject has retinitis pigmentosa.

(448) The second plurality of filters comprises a first vision deterioration filter that is fired at least when the first plurality of survey results indicates that the subject has had severe vision loss.

(450) The second plurality of filters comprises a first stomach ulcer filter that is fired at least when the first plurality of survey results indicates that the subject has had a stomach ulcer.

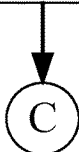

Fig. 4C

*(432 continued)*

*(452)* The second plurality of filters comprises a first bleeding problem filter that is fired at least when the first plurality of survey results indicates that the subject has a bleeding disorder.

*(454)* The second plurality of filters comprises a first genital abnormality filter that is fired at least when the first plurality of survey results indicates that the subject has an abnormal penile shape.

*(456)* The second plurality of filters comprises a first priapism filter that is fired at least when the first plurality of survey results indicates that the subject has experienced priapism.

*(458)* The second plurality of filters comprises a first blood cell disorder filter that is fired at least when the first plurality of survey results indicates that the subject has a blood cell disorder selected from the group consisting of sickle cell anemia, multiple myeloma, and leukemia.

*(460)* The second plurality of filters comprises a first drug interaction filter that is fired at least when the first plurality of survey results indicates that the subject is taking a medication that interacts with the cGMP-specific phosphodiesterase 5 ($PDE_5$) inhibitor pharmaceutical composition.

*(462)* The first drug interaction filter is fired when the first plurality of survey results indicates that the subject is taking a medication selected from the group consisting of an alpha blocker, an HIV protease inhibitor, an antifungal medication, an antibiotic, a blood pressure medication, and an erectile dysfunction medication.

*(464)* The warning corresponding to a respective filter in the second plurality of filters comprises a prompt for the subject to indicate whether they have discussed the risk factor underlying the respective filter in the second plurality of filters that was fired with a health care provider. Acknowledgement is obtained from the subject when the subject indicates that they have discussed the risk factor underlying the respective filter in the second plurality of filters that was fired with a health care provider.

*(466)* Obtain acknowledgment from the subject for the warning issued to the subject by any filter in the second plurality of filters.

Fig. 4D

(468) Proceed with a fulfillment process when no filter in the first plurality of filters has been fired and the subject has acknowledged each warning associated with each filter in the second plurality of filters that was fired.

(470) The fulfillment process comprises storing an indication in a subject profile of an initial order for the $PDE_5$ inhibitor pharmaceutical composition, communicating an over the counter drug facts label for the $PDE_5$ inhibitor pharmaceutical composition to the subject, and authorizing, upon confirmation from the subject that the over the counter drug facts label has been received and read, provision of the $PDE_5$ inhibitor pharmaceutical composition to the subject.

(472) Upon confirmation from the subject that the over the counter drug facts label has been received and read, the subject is authorized for provision of a dosage of from 2.5 mg to 10 mg of tadalafil no more than once per day.

(474) Upon confirmation from the subject that the over the counter drug facts label has been received and read, the subject is authorized for provision of a dosage of 5 mg of tadalafil no more than once per day.

(476) The fulfillment process further comprises storing a destination associated with the subject in the subject profile.

(478) The fulfillment process further comprises coordinating shipping of the $PDE_5$ inhibitor pharmaceutical composition to a physical address associated with the subject.

Fig. 4E

(486) Run all or a portion of the second plurality of survey results against a third plurality of filters of the first category class. When a respective filter in the third plurality of filters is fired, the subject is deemed not qualified for the PDE$_5$ inhibitor pharmaceutical composition and the re-fulfillment process is terminated without delivery of the PDE$_5$ inhibitor pharmaceutical composition to the subject.

(488) The third plurality of filters comprises a second erectile dysfunction filter that is fired at least when the second plurality of survey results indicates that the subject does not have erectile dysfunction.

(490) The third plurality of filters comprises a second vasodilator filter that is fired at least when the second plurality of survey results indicates that the subject is taking a vasodilator composition comprising a nitrate or a nitrile.

(492) The third plurality of filters comprises a second guanylate cyclase stimulator filter that is fired at least when the second plurality of survey results indicates that the subject is taking a guanylate cyclase stimulator mediation.

(494) The third plurality of filters comprises a second PDE$_5$ inhibitor filter that is fired at least when the second plurality of survey results indicates that the subject is taking a PDE$_5$ inhibitor composition.

(496) The third plurality of filters comprises a sexual intercourse filter that is fired at least when the second plurality of survey results indicates that the subject has experienced a symptom of heart problems during sexual intercourse since receiving their last provision of the PDE$_5$ inhibitor pharmaceutical composition.

(498) The third plurality of filters comprises a second priapism filter that is fired at least when the second plurality of survey results indicates that the subject has had priapism since receiving their last provision of the PDE$_5$ inhibitor pharmaceutical composition.

(500) The third plurality of filters comprises a sensory deterioration filter that is fired at least when the second plurality of survey results indicates that the subject has experienced a sudden vision loss or sudden hearing loss since receiving their last provision of the PDE$_5$ inhibitor pharmaceutical composition.

Fig. 4G

*(512)* Proceed with the re-fulfillment process when the re-fulfillment process is not already terminated by the firing of a filter in the third plurality of filters and the subject has acknowledged each warning associated with each filter in the fourth plurality of filters that was fired.

*(514)* The re-fulfillment process further comprises storing an indication in the subject profile of a re-order for the $PDE_5$ inhibitor pharmaceutical composition, communicating the over the counter drug facts label for the $PDE_5$ inhibitor pharmaceutical composition to the subject, and authorizing, upon confirmation from the subject that the over the counter drug facts label has been received and read, a re-order provision of the $PDE_5$ inhibitor pharmaceutical composition to the subject.

Are you taking recreational drugs called "poppers" such as amyl nitrate, amyl nitrite, and butyl nitrite?

552

Some recreational drugs called "poppers" such as amyl nitrate, amyl nitrite, and butyl nitrite are have adverse effects when taking with $PDE_5$ inhibitors.

Please consult with your doctor before taking $PDE_5$ inhibitor OTC.

Do you taking medicines called guanylate cyclase stimulators which include riociquat, a medicine that treats pulmonary arterial hypertension and chronic thromboembolic pulmonary hypertension? ⟵ 554

Have you ever had severe vision loss, including a condition called NAION? ⟵ 556

558

Are you taking any of the following:

Alpha blockers such as terazosin, tamsulosin, etc.    Yes   No

Medicines to treat high blood pressure                Yes   No

HIV protease inhibitors such as ritonavir             Yes   No

Oral antifungals such as ketoconazole or itraconazole Yes   No

Antibiotics such as clarithromycin, telithromycin, and the like   Yes   No

Medicines to treat erectile dysfunction               Yes   No

PDE$_5$ inhibitor OTC may not be right for you. Based on your answers, it is important to talk to your doctor about potential risks of taking PDE$_5$ inhibitor OTC. It may be helpful to have your summary of answers when talking to your doctor.

Has your doctor said it is OK for you to take PDE$_5$ inhibitor OTC?

Yes | No, View/Print Summary

METHODS FOR TREATING ERECTILE DYSFUNCTION WITH A CGMP-SPECIFIC PHOSPHODIESTERASE 5 INHIBITOR PHARMACEUTICAL COMPOSITION

CROSS REFERENCE TO RELATED APPLICATIONS

This application claims priority to U.S. Provisional Patent Application Ser. No. 62/685,230, filed Jun. 14, 2018, which is hereby incorporated by reference in its entirety.

TECHNICAL FIELD

The present disclosure relates generally to methods for treating erectile dysfunction by administering an over-the-counter cGMP-specific phosphodiesterase 5 inhibitor pharmaceutical composition to a subject in need thereof, who has been qualified for over-the-counter access to the composition.

BACKGROUND

The prevalence of erectile dysfunction is growing worldwide. For example, it was estimated that the number of global diagnoses of erectile dysfunction will approximately double from 152 million patients in 1995 to 322 million patients by 2025. Ayta I A et al, BJU Int. 84(1):50-6 (1999). Moreover, erectile dysfunction is vastly undertreated. For instance, analysis of data from a population of 6.2 million patients with a known diagnosis of erectile dysfunction, showed that approximately 75% of these patients went untreated. Frederick L R, et al., J Sex Med. 11(10):2546-53 (2014).

Fortunately, erectile dysfunction can be managed, for example, using a cGMP-specific phosphodiesterase 5 ($PDE_5$) inhibitors, which are well established prescription pharmaceuticals used to treat erectile dysfunction. For instance, the efficacy of tadalafil, which was first approved in the U.S. for the treatment erectile dysfunction in 2011, has been demonstrated in at least five double-blind, placebo-controlled, randomized studies (Rashid A., 2005, "The Efficacy and Safety of PDE5 Inhibitors," Clin Cornerstone, 7(1), p 47). However, access to $PDE_5$ inhibitors is restricted by the requirement for a prescription. Unfortunately, long-term trends demonstrate many people avoid prescription medications, including $PDE_5$ inhibitors.

One approach to making $PDE_5$ inhibitors more accessible is to make them available without a prescription, e.g., over the counter ("OTC"). There are a variety of health benefits derived from switching a drug from prescription to OTC including generating wider availably to therapies, providing a greater number of therapeutic approaches, providing direct and rapid access to treatments, providing patients with an active role in their own health care, and allowing patients to become self-reliant in preventing and relieving minor symptoms or conditions (World Health Organization, 2000, "Guidelines for the Regulatory Assessment of Medicinal Products for use in Self-Medication," Print). Given the large number of individuals with erectile dysfunction, providing access to OTC $PDE_5$ inhibitors could provide significant societal health benefits.

However, switching distribution of a pharmaceutical from prescription-only to OTC creates a significant risk that the patient population will be unable to appropriately self-select themselves for safe use of the pharmaceutical use and then self-medicate using the drug in a responsible manner. The manifestations embodied within these concerns include incorrect self-diagnosis, incorrect drug-qualification, unrecognized drug-drug interactions (DDI), unanticipated adverse drug reactions and/or side-effects, improper dosing and/or administration, masking of a disease, addiction, inappropriate drug dependency, substance abuse, and patient delay in seeking necessary medical attention. Ruiz et al., Current Drug Safety, 5(4):315 (2010).

Because $PDE_5$ inhibitors cause adverse effects in certain patients, the population receiving the drug should be carefully selected and monitored. In order to ensure the safety of OTC distribution of $PDE_5$ inhibitors, prospective patients must effectively self-select themselves for the drug. Recent studies, however, found that many prospective patients do not pay consistent attention to guidelines printed on the packaging of OTC drugs, to ensure safe and responsible use. PR Newswire Association, "Americans Should Pay More Attention to Over-the-Counter (OTC) medicine Labels According to New Survey," October 15 (2015) (citing McNeil Consumer Healthcare research). According to these studies, 40% of prospective patients consider the directions as just guidelines and 80% of patients do not re-read the label of an OTC medicine they have used before. Even more troubling, only 58% of men surveyed found it very important to pay attention to restrictions on an OTC label.

Currently, there are two regulatory pathways for legal marketing of an OTC drug in the United States. In the first pathway, marketing occurs in compliance with an OTC drug monograph, that sets regulatory standards for non-prescription drugs that are not covered by human drug applications, e.g., a New Drug Application (NDA) or Abbreviated New Drug Application (ANDA). An OTC monograph is created as a result of a three phase OTC drug review by the FDA. In phase I of the review, an advisory review panel determines whether ingredients in the proposed OTC composition could be generally recognized as safe and effective for use in self-treatment. In the second pathway, marketing occurs under the authority of an approved product-specific new drug application (NDA), or an abbreviated new drug application (ANDA). In order to support an over-the-counter label for a drug for which regulatory approval is being sought through an NDA, a consumer research study is required to assess the consumer's ability to select and deselect themselves as appropriate users of the drug, based on the proposed labeling for the drug. Oliver, A., Regulatory Rapporteur, 10(3):4-9 (2013), which is incorporated by reference herein.

However, attempts at switching distribution of drugs having potentially far-reaching benefits for societal health, from prescription-only to an OTC model, have repeatedly failed, in large part due to concerns over inappropriate patient selection and medication. Possibly the best documented cases relate to statins used to treat high cholesterol.

For instance, Merck has had at least three applications for sale of over the counter lovastatin rejected by the FDA, in 2000, 2005, and 2007. In 2005, their proposal to permit over the counter sales of lovastatin was rejected by an expert advisory panel at the FDA in 2005. The panel was concerned by a marketing study performed to support the proposal in which approximately one third of 3316 customers who were offered the drug over the counter decided they would purchase the drug. After reviewing the data, the panel concluded that 45% of the purchases would have been inappropriate for a variety of reasons, including the age of the subject, the subject's lack of knowledge about their condition, and contraindications associated with their condition. Dyer O., BMJ, 330(7484):164 (2005). In 2007, the board again concluded that the ability of consumers to appropriately self-select and to adequately comply with chronic MEVACOR® therapy without the intervention of a physician had not been demonstrated. Division of Metabolic and Endocrine Drug Products, 2005, "NDA 21-213 Non-prescription MEVACOR® 20 mg Joint Advisory Committee Meeting."

Similarly, Pfizer announced in 2011 its intention to switch LIPITOR® from prescription-only to OTC status. Sett OTC bulletin, 16 Nov. 2011, page 7. However, they abandoned their attempt in 2014 when a phase 3 "actual use" trial, intended to simulate the OTC use of LIPITOR® (atorvastatin calcium) 10 mg, failed to meet its primary objectives on the basis that patient compliance with the direction to check their low-density lipoprotein cholesterol (LDL-C) level and, after checking their LDL-C level, take appropriate action based on their test results was unsatisfactory. Pfizer Inc., "Pfizer Reports Second-Quarter 2015 Results," (2015).

In fact, in the nearly two decades since Bristol-Myers Squibb and Merck & Co first failed in their attempts to switch PRAVACHOL® and lovastatin, respectively, to OTC, a statin has never been granted OTC status in the United States. This is despite that nearly ⅙th of the adult population in the U.S. is eligible for cholesterol-lowering medications, under the current guidelines, but are not taking anything.

The information disclosed in this Background section is only for enhancement of understanding of the general background of the invention and should not be taken as an acknowledgment or any form of suggestion that this information forms the prior art already known to a person skilled in the art.

SUMMARY

Given the above background, what is needed in the art are systems and methods for qualifying a human subject for delivery of a cGMP-specific phosphodiesterase 5 ($PDE_5$) inhibitor pharmaceutical composition over-the-counter for treating erectile dysfunction.

The present disclosure addresses the need in the art for systems and methods configured for qualifying a human subject for over-the-counter delivery of a cGMP-specific phosphodiesterase 5 ($PDE_5$) inhibitor pharmaceutical composition (e.g., tadalafil) for treating erectile dysfunction. In the present disclosure, systems and methods are provided for over-the-counter delivery of a $PDE_5$ inhibitor pharmaceutical composition to a subject. Survey results from the subject are run against a first plurality of filters. When a filter in the first plurality is fired, the subject is deemed not qualified for delivery of the $PDE_5$ inhibitor pharmaceutical composition. The survey results are also run against a second plurality of filters. When a respective filter in the second plurality is fired, the subject is provided with a corresponding warning. The method proceeds to a fulfillment process when no filter in the first plurality is fired and the subject has acknowledged each warning associated with each fired filter in the second plurality of filters. The fulfillment process stores the composition order, communicates a drug facts label for the $PDE_5$ inhibitor pharmaceutical composition to the subject, and authorizes, upon subject confirmation that the label has been read, provision of $PDE_5$ inhibitor pharmaceutical composition to the subject.

Accordingly, one aspect of the present disclosure provides a method for qualifying a subject for over-the-counter delivery of a $PDE_5$ inhibitor pharmaceutical composition in order to treat erectile dysfunction of the subject. The method includes conducting a first survey of the subject in order to obtain a variety of survey results. In some embodiments, the survey results indicate one or more of: a gender of the subject, an age of the subject, an erectile dysfunction status of the subject, whether the subject is taking a nitrate or nitrite vasodilator composition, whether the subject is taking a guanylate cyclase stimulator medication, whether the subject is taking a $PDE_5$ inhibitor composition, whether the subject has ever had a heart problem, a blood pressure status of the subject, whether the subject has ever had a stroke, whether the subject has a liver problem, a kidney function status of the subject, whether the subject has retinitis pigmentosa, whether the subject has developed vision loss, whether the subject has ever had a stomach ulcer, whether the subject has a bleeding disorder, a genital status of the subject, whether the subject has ever experienced priapism, whether the subject has a blood cell disorder, and whether the subject is taking a medication that interacts (e.g., a pharmacokinetic interaction and/or a pharmacodynamic interaction) with the $PDE_5$ inhibitor pharmaceutical composition.

The method also includes running all or a portion of the survey results against a first plurality of filters of a first category class, corresponding to contraindications associated with the $PDE_5$ inhibitor pharmaceutical composition. When a respective filter in the first plurality of filters is fired, the subject is deemed not qualified for delivery of the $PDE_5$ inhibitor pharmaceutical composition, and the method is then terminated accordingly without delivery of the $PDE_5$ inhibitor pharmaceutical composition to the subject. In some embodiments, the first plurality of filters includes one or more of a gender filter, an age filter, an erectile dysfunction filter, a vasodilator filter, a guanylate cyclase stimulator filter, and a $PDE_5$ inhibitor filter.

The method also includes running all or a portion of the survey results against a second plurality of filters of a second category class, corresponding to risk factors associated with the $PDE_5$ inhibitor pharmaceutical composition. When a respective filter in the second plurality of filters is fired, the subject is provided with a warning corresponding to the respective filter. In some embodiments, the second plurality of filters includes one or more of a first heart problem filter, a first blood pressure filter, a first stroke filter, a first liver disease filter, a first kidney disease filter, a first retinitis pigmentosa filter, a first stomach ulcer filter, a first bleeding problem filter, a first genital abnormality filter, a first priapism filter, a first blood cell disorder, and a first drug interaction filter. However, unlike filters in the first plurality of filters, filters in the second plurality of filters do not automatically terminate the process without delivery of the $PDE_5$ inhibitor pharmaceutical composition to the subject.

The method continues by obtaining acknowledgment from the subject for the warning issued to the subject by any filter in the second plurality of filters.

The method continues by proceeding with a fulfillment process when no filter in the first plurality of filters has been fired and the subject has acknowledged each warning associated with each filter in the second plurality of filters that was fired.

In some embodiments, the fulfillment process includes storing an indication in a subject profile of an initial order for the $PDE_5$ inhibitor pharmaceutical composition, communicating an over-the-counter drug label for the $PDE_5$ inhibitor pharmaceutical composition, and authorizing, upon confirmation from the subject that the over-the-counter drug label has been received and read, provision of the $PDE_5$ inhibitor pharmaceutical composition to the subject.

In some embodiments, the PDE$_5$ inhibitor pharmaceutical composition has the structure:

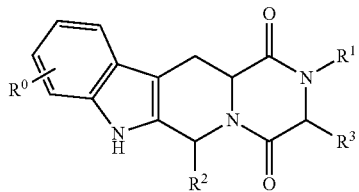

where,

R$^0$ represents hydrogen, halogen or C$_{1-6}$ alkyl;

R$^1$ represents hydrogen, C$_{1-6}$ alkyl, C$_{2-6}$ alkenyl, C$_{2-6}$ alkynyl, haloC$_{1-6}$ alkyl, C$_{3-8}$ cycloalkyl, C$_{3-8}$ cycloalkyl-C$_{1-3}$ alkyl, arylC$_{1-3}$ alkyl or heteroarylC$_{1-3}$ alkyl;

R$^2$ represents an optionally substituted mono-cyclic aromatic ring selected from benzene, thiophene, furan and pyridine or an optionally substituted bicyclic ring

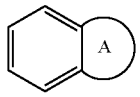

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and R$^3$ represents hydrogen or C1-3 alkyl, or R$^1$ and R$^3$ together represent a 3- or 4-membered alkyl or alkenyl chain, or a pharmaceutically acceptable salt thereof.

In some embodiments, the PDE$_5$ inhibitor pharmaceutical composition includes tadalafil or a pharmaceutically acceptable salt thereof. In some embodiments, the PDE$_5$ inhibitor composition includes vardenafil.

In one aspect, the present disclosure provides a method for qualifying a subject (e.g., a subject who was previously qualified to receive a provision of the PDE$_5$ inhibitor pharmaceutical composition) for a re-order of the PDE$_5$ inhibitor pharmaceutical composition (e.g., which is optionally performed in conjunction with a method for qualifying the subject for a first order of the PDE$_5$ inhibitor pharmaceutical composition). The method includes a re-fulfillment procedure that includes conducting a second survey of the subject in order to obtain a second plurality of survey results. In some embodiments, the second plurality of survey results indicate one or more of: an erectile dysfunction status of the subject, whether the subject has started to take a nitrate or nitrite vasodilator composition since receiving their last provision of the PDE$_5$ inhibitor pharmaceutical composition, whether the subject has started to take a guanylate cyclase stimulator medication since receiving their last provision of the PDE$_5$ inhibitor pharmaceutical composition, whether the subject has started to take a PDE$_5$ inhibitor composition since receiving their last provision of the PDE$_5$ inhibitor pharmaceutical composition, whether the subject has developed symptoms of heart problems during sexual intercourse since receiving their last provision of the PDE$_5$ inhibitor pharmaceutical composition, whether the subject has experienced priapism since receiving their last provision of the PDE$_5$ inhibitor pharmaceutical composition, whether the subject has developed hearing or vision loss since receiving their last provision of the PDE$_5$ inhibitor pharmaceutical composition, whether the subject has developed a symptom of heart problems since receiving their last provision of the PDE$_5$ inhibitor pharmaceutical composition, a blood pressure status of the subject, whether the subject has had a stroke since receiving their last provision of the PDE$_5$ inhibitor pharmaceutical composition, whether the subject has developed a liver problem since receiving their last provision of the PDE$_5$ inhibitor pharmaceutical composition, a kidney function status of the subject, whether the subject has developed retinitis pigmentosa since receiving their last provision of the PDE$_5$ inhibitor pharmaceutical composition, whether the subject has developed a stomach ulcer since receiving their last provision of the PDE$_5$ inhibitor pharmaceutical composition, whether the subject has developed a bleeding disorder since receiving their last provision of the PDE$_5$ inhibitor pharmaceutical composition, whether the subject has developed an abnormal genital shape since receiving their last provision of the PDE$_5$ inhibitor pharmaceutical composition, whether the subject has developed a blood cell disorder since receiving their last provision of the PDE$_5$ inhibitor pharmaceutical composition, and whether the subject has started taking a medication that interacts with the PDE$_5$ inhibitor pharmaceutical composition since receiving their last provision of the PDE$_5$ inhibitor pharmaceutical composition.

The method also includes running all or a portion of the second plurality of survey results against a third plurality of filters of the first category class, corresponding to contraindications associated with the PDE$_5$ inhibitor pharmaceutical composition. When a respective filter in the third plurality of filters is fired, the subject is deemed not qualified for the PDE$_5$ inhibitor pharmaceutical composition and, the re-fulfillment process is terminated without delivery of the PDE$_5$ inhibitor pharmaceutical composition to the subject. In some embodiments, the third plurality of filters includes an erectile dysfunction filter, a vasodilator filter, a guanylate cyclase stimulator filter, a PDE$_5$ inhibitor filter, a sexual intercourse filter, a priapism filter, and a sensory deterioration filter.

The method also includes running all or a portion of the second plurality of survey results against a fourth plurality of filters of the second category class, corresponding to risk factors associated with the PDE$_5$ inhibitor pharmaceutical composition. When a respective filter in the fourth plurality of filters is fired the subject is provided with a warning corresponding to the respective filter. In some embodiments, the fourth plurality of filters includes one or more of: a heart problem filter, a blood pressure filter, a stroke filter, a liver disease filter, a kidney disease filter, a retinitis pigmentosa filter, a stomach ulcer filter, a bleeding problem filter, a genital abnormality filter, a blood cell disorder, and a drug interaction filter.

The method continues by obtaining acknowledgment from the subject for the warning issued to the subject by any filter in the fourth plurality of filters. When the re-fulfillment process is not already terminated by the firing of a filter in the third plurality of filters and the subject has acknowledged each warning associated with each filter in the fourth plurality of filters that was fired, the method continues with a re-fulfillment procedure.

In some embodiments, the method includes storing an indication in the subject profile of a re-order for the PDE$_5$ inhibitor pharmaceutical composition, communicating an over-the-counter drug facts label for the PDE$_5$ inhibitor pharmaceutical composition to the subject, and authorizing, upon confirmation from the subject that the over-the-counter drug facts label has been received and read, a re-order provision of the PDE$_5$ inhibitor pharmaceutical composition to the subject.

BRIEF DESCRIPTION OF THE DRAWINGS

FIGS. 3A, 3B, and 3C collectively illustrate an example device associated with a human subject for qualifying the human subject for over-the-counter delivery of a PDE$_5$ inhibitor pharmaceutical composition to treat erectile dysfunction, in accordance with an embodiment of the present disclosure, where it will be appreciated that the example device of FIGS. 3A through 3C works in conjunction with the device of FIG. 2 to perform the methods illustrated in FIGS. 4 through 8 in some embodiments by, for instance providing the device of FIG. 2 with survey results and/or the results of firing filters of the present disclosure against such survey results but that, in alternative embodiments, the device of FIG. 2 performs all the methods of the present disclosure and the device of FIGS. 3A through 3C is not used. In still further alternative embodiments, the device of FIGS. 3A through 3C performs the methods of the present disclosure and the device of FIG. 2 is not used.

FIGS. 4A, 4B, 4C, 4D, 4E, 4F, 4G, 4H, and 4I collectively provide a flow chart of processes for qualifying a human subject for over-the-counter delivery of a PDE$_5$ inhibitor pharmaceutical composition to treat erectile dysfunction, where elements in dashed boxes are optional, in accordance with various embodiments of the present disclosure.

FIGS. 5A, 5B, 5C, 5D, and 5E illustrate example survey questions for obtaining survey results, in accordance with an embodiment of the present disclosure.

Figure 1:
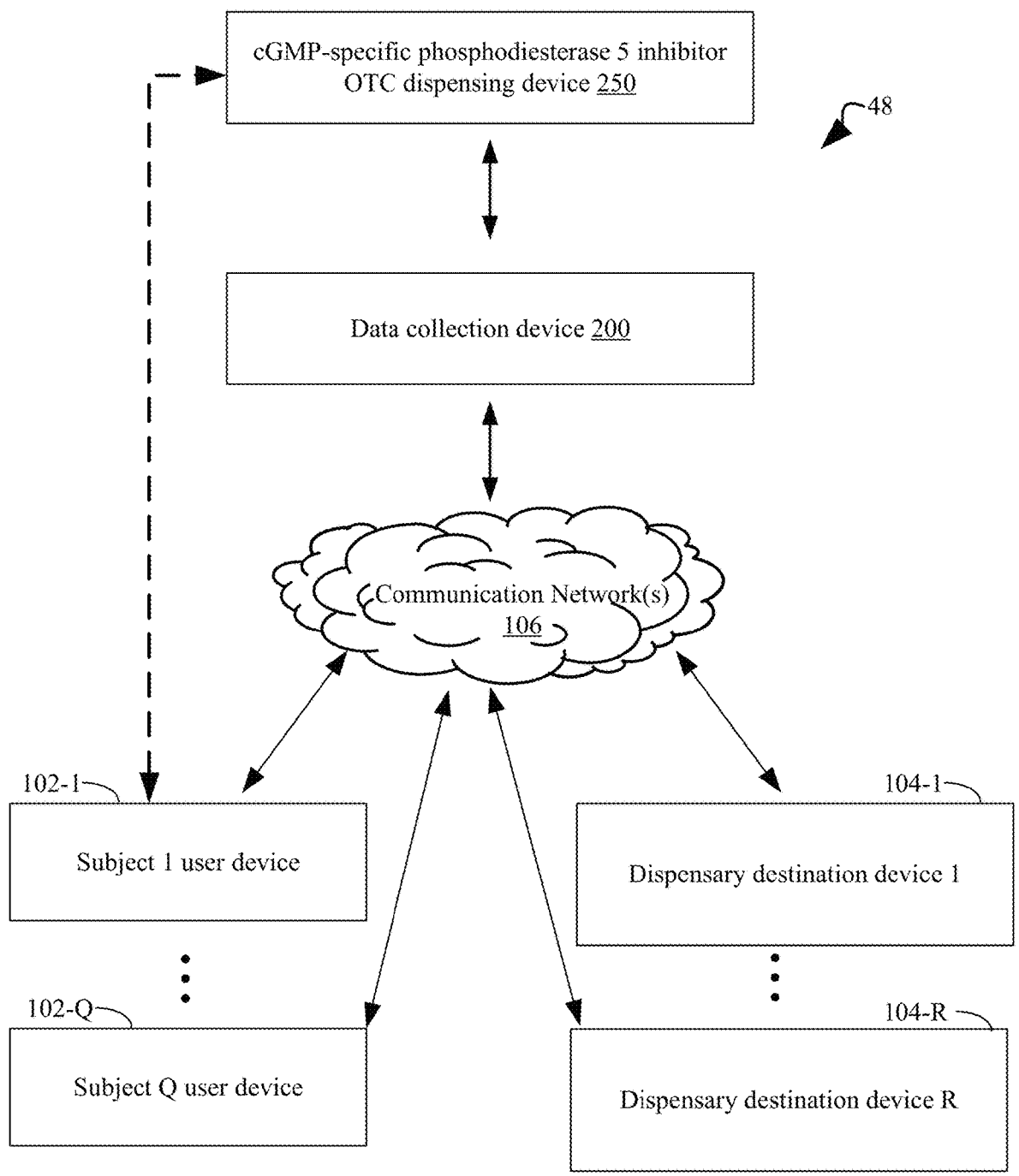
FIG. 1 illustrates an exemplary system topology that includes a PDE$_5$ inhibitor pharmaceutical composition over-the-counter (OTC) dispensing device for qualifying a human subject for over-the-counter delivery of a PDE$_5$ inhibitor pharmaceutical composition to treat erectile dysfunction, a data collection device for collecting subject data, one or more user devices associated with human subjects, and one or more dispensary destinations for distributing the PDE$_5$ inhibitor pharmaceutical composition over-the-counter, where the above-identified components are interconnected, optionally through a communications network, in accordance with an embodiment of the present disclosure.

In the figures, reference numbers refer to the same or equivalent parts of the present invention throughout the several figures of the drawing.

DETAILED DESCRIPTION

Erectile dysfunction is a growing health problem, in the United States and worldwide. Although erectile dysfunction can be effectively treated and/or prevented using established pharmaceutical compositions, access to these drugs is hindered by to the requirement for a prescription, as many individuals do not have adequate access and/or avoid the healthcare system for a variety of reasons. Accordingly, many people are not managing their erectile dysfunction or conditions related to erectile dysfunction appropriately. While over-the-counter alternatives to these prescription pharmaceuticals would increase access to these compositions, thereby improving population management of erectile dysfunction around the world, patients often have difficulty self-selecting themselves for an appropriate over-the-counter medication. Because inappropriate use of these drugs can result in ineffective treatment and/or serious side-effects, better methods for selecting for, and treating patients with, other-the-counter erectile dysfunction medications are needed. The present disclosure provides, among other aspects, methods, systems, and computer readable media that solve these problems.

Reference will now be made in detail to implementations, examples of which are illustrated in the accompanying drawings. In the following detailed description of implementations, numerous specific details are set forth in order to provide a thorough understanding of the present invention. However, it will be apparent to one of ordinary skill in the art that the present invention may be practiced without these specific details.

It will also be understood that, although the terms first, second, etc. may be used herein to describe various elements, these elements should not be limited by these terms. These terms are only used to distinguish one element from another. For example, a first filter could be termed a second filter, and, similarly, a second filter could be termed a first filter, without departing from the scope of the present disclosure. The first filter and the second filter are both filters, but they are not the same filter.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "over-the-counter" means to provide by retail purchase, subject to the constraints disclosed herein, but without a prescription or license from a physician or medical practitioner.

As used herein, the term "pharmaceutical compound" refers to any physical state of a material. Pharmaceutical compounds include capsules, tablets, liquids, topical formulations, and inhaled formulations.

As used herein, the term "contraindication" refers to a condition that makes a treatment, e.g., over-the-counter use of a cGMP-specific phosphodiesterase 5 ($PDE_5$) inhibitor pharmaceutical composition, inadvisable. Contraindications include physical characteristics of a subject, e.g., is not a male or has a liver disease, and contemporaneous drug use, e.g., $PDE_5$ inhibitor pharmaceutical composition use. In the present context, identification of a contraindication fires a filter of a first category class, which prevents authorizing provision of a $PDE_5$ inhibitor pharmaceutical composition, in accordance with some implementations of the methods, systems, and software disclosed herein.

As used herein, the term "risk factor" refers to a condition that makes a treatment, e.g., over-the-counter use of a $PDE_5$ inhibitor pharmaceutical composition, possibly inadvisable. Risk factors include physical characteristics of a subject, e.g., a blood pressure reading, and contemporaneous drug use, e.g., use of a vasodilator medication. In the present context, identification of a risk factor fires a filter of a second category class, which prevents authorizing provision of a $PDE_5$ inhibitor pharmaceutical composition without confirmation that the subject has discussed the risk factor with a medical professional, in accordance with some implementations of the methods, systems, and software disclosed herein.

As used herein, "drug interactions," e.g., with a $PDE_5$ inhibitor, include pharmacokinetic drug interactions and pharmacodynamics drug interactions. Generally, a pharmacokinetic drug interaction is an interaction between two drugs (e.g., a $PDE_5$ inhibitor and a second drug) that result in alterations in the absorption, transport, distribution, metabolism, and/or excretion of either drug. Generally, a pharmacokinetic drug interaction is an interaction between two drugs (e.g., a $PDE_5$ inhibitor and a second drug) that result in a direct change in the effect or either drug. For a more comprehensive summary of pharmacokinetic drug interactions and pharmacodynamics drug interactions, see, Cascorbi, I, Dtsch Arztebl Int., 109(33-34):546-55 (2012), the content of which is hereby incorporated by reference.

In the context of the present disclosure, classification of a condition as either a contraindication or a risk factor is specific to a particular identity and dose of a $PDE_5$ inhibitor pharmaceutical composition being authorized for over-the-counter use. Classification of a particular condition, e.g., contemporaneous $PDE_5$ inhibitor pharmaceutical composition use, may vary between different $PDE_5$ inhibitor pharmaceutical compositions (e.g., it may be classified as a contraindication for a first $PDE_5$ inhibitor, a risk factor for a second $PDE_5$ inhibitor, and/or neither for a third $PDE_5$ inhibitor). Likewise, a particular condition may be classified as a contraindication for use of a particular $PDE_5$ inhibitor at a first over-the-counter dosage, classified as a risk factor for the same particular $PDE_5$ inhibitor at a second (e.g., lower) over-the-counter dosage, and/or classified as neither for the same particular $PDE_5$ inhibitor at a third (e.g., lowest) over-the-counter dosage.

As used herein, whether a subject "has developed" a condition since receiving their last provision of a $PDE_5$ inhibitor refers to both conditions that are new to the subject, i.e., a condition that the subject did not have at the time they received their last provision of the $PDE_5$, and conditions that have been newly diagnosed, regardless of whether the condition existed when the subject received their last provision of the $PDE_5$ inhibitor, i.e., a condition that the subject was not aware of when they received their last provision of the $PDE_5$ inhibitor.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (e.g. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10,\ 12-13}$ linoeyl chain.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl substituent groups (or rings) that contain from one to four heteroatoms selected from N, O, S, Si and B, wherein the nitrogen and sulfur atoms are optionally oxidized, and the nitrogen atom(s) are optionally quaternized. An exemplary heteroaryl group is a six-membered azine, e.g., pyridinyl, diazinyl and triazinyl. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes aryl, heteroaryl and heteroarene rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl, and "heteroaryl") are meant to optionally include both substituted and unsubstituted forms of the indicated species. Exemplary substituents for these species are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', —NR'R", —SR', halogen, —SiR'R"R'", —OC(O)R', —C(O)R', —CONR'R", —OC(O)NR'R", —NR"C(O)R', —NR'—C(O)NR"R'", —NR"C(O)$_2$R', —NR— C(NR'R"R'")=NR"", NR C(NR'R")=NR'", —S(O)R', —S(O)$_2$R', —S(O)$_2$NR'R", NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). These terms encompass groups considered exemplary "alkyl group substituents," which are components of exemplary "substituted alkyl" and "substituted heteroalkyl" moieties.

Similar to the substituents described for the alkyl radical, substituents for the aryl heteroaryl and heteroarene groups are generically referred to as "aryl group substituents." The substituents are selected from, for example: groups attached to the heteroaryl or heteroarene nucleus through carbon or a heteroatom (e.g., P, N, O, S, Si, or B) including, without limitation, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O) NR'R", —NR"C(O)R', NR' C(O)NR"R'", —NR"C(O)$_2$R', NR—C(NR'R"R'")=NR"", NR C(NR'R")=NR'", —S(O) R', —S(O)$_2$R', —S(O)$_2$NR'R", NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system. Each of the above-named groups is attached to the heteroarene or heteroaryl nucleus directly or through a heteroatom (e.g., P, N, O, S, Si, or B); and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

As used herein, the term "heteroatom" includes oxygen (O), nitrogen (N), sulfur (S) and silicon (Si), boron (B) and phosphorous (P).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

In one aspect, the present disclosure conducts a survey of a subject to obtain survey results in order to determine if the subject qualifies for an over-the-counter (OTC) $PDE_5$ inhibitor pharmaceutical composition for the treatment of erectile dysfunction. The survey results are used as the basis for running filters of a first category class. If the triggering conditions of any of the filters in the first category class are fired, the subject does not qualify for the OTC $PDE_5$ inhibitor pharmaceutical composition. The survey results are also used as the basis for running filters of a second category class. If the triggering conditions of any of the filters in the second category class are fired, the subject is provided with warning messages associated with the respective filters of the second category class that have been fired. If none of the filters in the first category class are fired and the subject successfully addresses the warning messages associated with the respective filters of the second category class that have been fired a fulfillment process is initiated for OTC delivery of the $PDE_5$ inhibitor pharmaceutical composition.

FIG. 1 illustrates an example of an integrated system 48 for conducting one or more surveys of subjects in order to qualifying the subjects for OTC delivery of a $PDE_5$ inhibitor pharmaceutical composition. The integrated system 48 includes one or more connected user devices 102. The user devices 102 are configured for entering survey data and making requests for the $PDE_5$ inhibitor pharmaceutical composition. The system 48 also includes one or more dispensary destination devices 104 that are configured to receive instructions in order to provide the $PDE_5$ inhibitor pharmaceutical composition to qualifying subjects. Furthermore, the system 48 includes a cGMP-specific phosphodiesterase 5 ($PDE_5$) inhibitor pharmaceutical composition over-the-counter (OTC) dispensing device 250 and one or more data collection devices 200 that are configured for collecting subject data.

Throughout the present disclosure, the data collection device 200 and the $PDE_5$ inhibitor pharmaceutical composition OTC dispensing device 250 will be referenced as separate devices solely for purposes of clarity. That is, the disclosed functionality of the data collection device 200 and the disclosed functionality of the $PDE_5$ inhibitor pharmaceutical composition OTC dispensing device 250 are contained in separate devices as illustrated in FIG. 1. However, it will be appreciated that, in fact, in some embodiments, the disclosed functionality of the data collection device 200 and the disclosed functionality of the $PDE_5$ inhibitor pharmaceutical composition OTC dispensing device 250 are contained in a single device.

With the integrated system 48, survey results from the subjects are run against a first plurality of filters (e.g., filter 216-1, filter 216-2, filter 216-3, etc.) When a filter in the first plurality of filters (e.g., filter 216) is fired for a respective subject, the respective subject is deemed not qualified for the $PDE_5$ inhibitor pharmaceutical composition. The survey results are also run against a second plurality of filters (e.g., filter 222-1, filter 222-2, filter 222-6, etc.) When a respective filter in the second plurality is fired for a respective subject, the respective subject is provided with a warning (e.g., filter warning 226) associated with the respective filter. In some embodiments the survey results are run against the first plurality of filters and the second plurality of filters concurrently. In some embodiments the survey results are run against the first plurality of filters and then against the second plurality of filters. The method enabled by the integrated system 48 proceeds to a fulfillment process when no filter in the first plurality fires and the subject has acknowledged, or otherwise successfully addressed, each warning associated with each filter in the second plurality of filters that fired. As part of the fulfillment process, the composition order is stored (e.g., in a user profile 234 associated with the subject to receive the drug), a drug facts label (e.g., drug facts label 230) for the $PDE_5$ inhibitor is communicated to the qualifying subject. Upon subject confirmation that the label has been read, authorization is granted to dispense the $PDE_5$ inhibitor.

Referring to FIG. 1, the $PDE_5$ inhibitor pharmaceutical composition OTC dispensing device 250 qualifies a subject for over-the-counter delivery of a $PDE_5$ inhibitor pharmaceutical composition to treat erectile dysfunction. To accomplish this, the data collection device 200, which is in electrical communication with the $PDE_5$ inhibitor pharmaceutical composition OTC dispensing device 250, receives survey results originating from one or more user devices 102 associated with corresponding subjects. In some embodiments, the data collection device 200 receives such survey results directly from the user devices 102. For instance, in some embodiments the data collection device 200 receives this data wirelessly through radio-frequency signals. In some embodiments, such signals are in accordance with an 802.11 (Wi-Fi), Bluetooth, or ZigBee standard. In some embodiments, the data collection device 200 receives such data directly, analyzes the data, and passes the analyzed data to the $PDE_5$ inhibitor pharmaceutical composition OTC dispensing device 250.

In some embodiments, the data collection device 200 and/or the $PDE_5$ inhibitor pharmaceutical composition OTC dispensing device 250 is not proximate to the subject and/or does not have wireless capabilities or such wireless capabilities are not used for the purpose of acquiring survey results. In some embodiments, a communication network 106 may be used to survey questions (e.g., survey questions 208, 212) from the $PDE_5$ inhibitor pharmaceutical composition OTC dispensing device 250 to user devices 102 and the answers to such survey questions from the user devices 102 to the data collection device 200 and/or the $PDE_5$ inhibitor pharmaceutical composition OTC dispensing device 250. Further, in some embodiments the communication network 106 is used to communicate authorization to dispense the $PDE_5$ inhibitor survey questions from the $PDE_5$ inhibitor pharmaceutical composition OTC dispensing device 250 to dispensary destination devices 104.

Examples of networks 106 include the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 48 are possible. For instance, rather than relying on a communications network 106, the one or more user devices 102 and the one or more dispensary destination devices 104 may communicate directly to the data collection device 200 and/or the $PDE_5$ inhibitor pharmaceutical composition OTC dispensing device 250. Further, the data collection device 200 and/or the $PDE_5$ inhibitor pharmaceutical composition OTC dispensing device 250 may constitute a portable electronic device, a server computer, or in fact constitute several computers that are linked together in a network, be a virtual machine in a cloud computing context, be a container in a cloud computer context, or a combination thereof. As such, the exemplary topology shown in FIG. 1 merely serves to describe the features of an embodiment of the present disclosure in a manner that will be readily understood to one of skill in the art.

Figure 2:
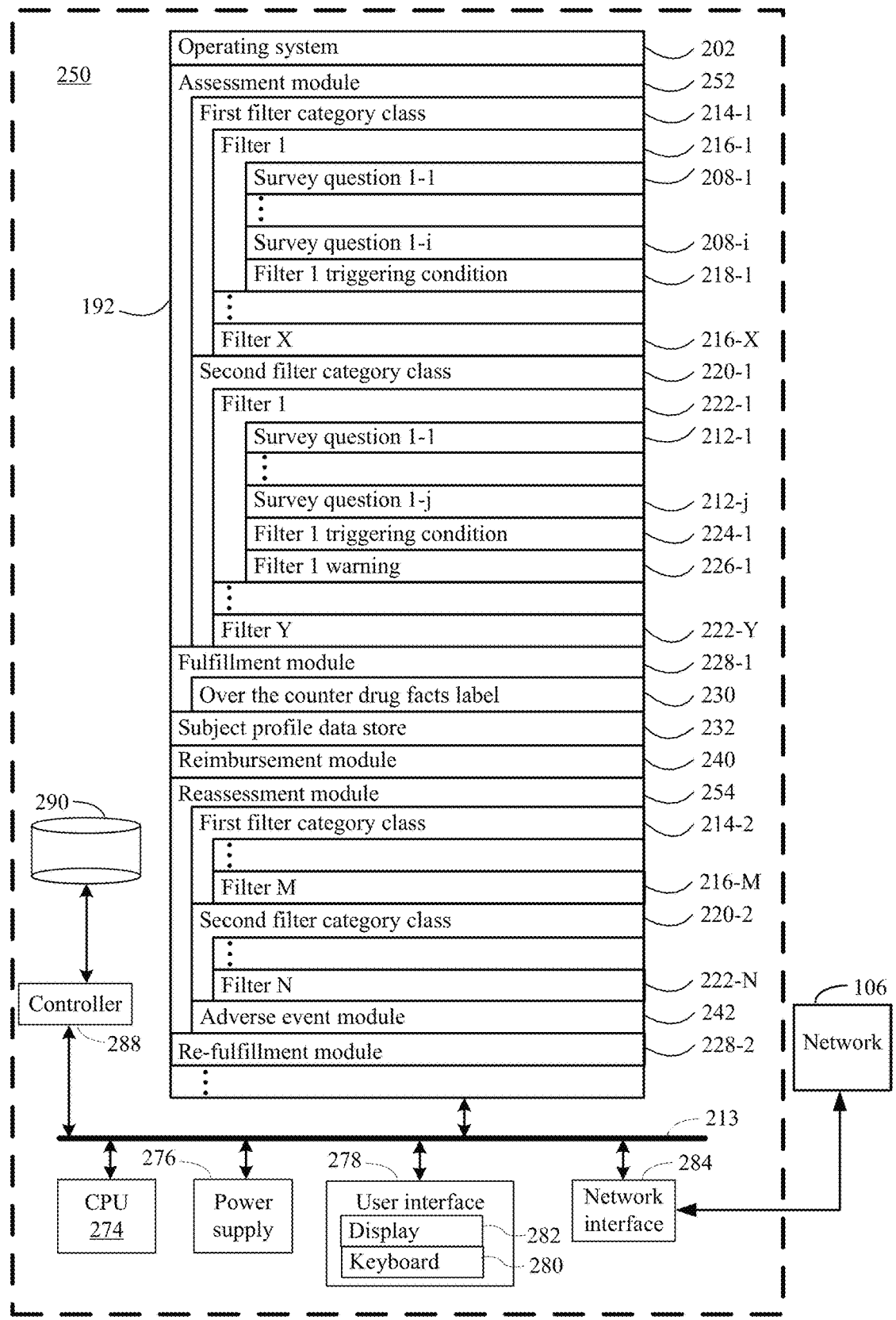
FIG. 2 illustrates an example device for qualifying a human subject for delivery of a PDE$_5$ inhibitor pharmaceutical composition over-the-counter to treat erectile dysfunction in accordance with various embodiments of the present disclosure.

Turning to FIG. 2 with the foregoing in mind, an exemplary $PDE_5$ inhibitor pharmaceutical composition OTC dispensing device 250 configured for determining whether a subject is qualified for OTC delivery of a $PDE_5$ inhibitor is depicted. Referring to FIG. 2, in typical embodiments, the $PDE_5$ inhibitor pharmaceutical composition OTC dispensing device 250 comprises one or more computers. For purposes of illustration in FIG. 2, the $PDE_5$ inhibitor pharmaceutical composition OTC dispensing device 250 is represented as a single computer that includes all of the functionality for qualifying a human subject for over-the-counter delivery of a $PDE_5$ inhibitor pharmaceutical composition to treat erectile dysfunction. However, the present disclosure is not limited thereto. In some embodiments, the functionality for qualifying a human subject for over-the-counter delivery of a $PDE_5$ inhibitor pharmaceutical composition to treat erectile dysfunction is spread across any number of networked computers and/or resides on each of several networked computers, is hosted on one or more virtual machines at a remote location accessible across the communications network 106, and/or is hosted on one or more containers at a remote location accessible across the communications network 106. One of skill in the art will appreciate that any of a wide array of different computer topologies are used for the application and all such topologies are within the scope of the present disclosure.

The $PDE_5$ inhibitor pharmaceutical composition OTC dispensing device 250 of FIG. 2 is configured to conduct a first survey (e.g., using assessment module 252 to perform an initial qualification of the subject for provision of a $PDE_5$ inhibitor pharmaceutical composition) and/or a second survey (e.g., using reassessment module 254 to perform a re-qualification of the subject for provision of a $PDE_5$ inhibitor pharmaceutical composition). The first survey (e.g., the assessment) comprises a variety of questions 208, 212 associated with filters 216, 222 within a plurality of filters of the first filter category class 214-1 and a plurality of filters in the second filter category class 220-1, respectively. Answers to the questions in the first survey received by the device are run against filters of a first category class 214-1 and filters of a second category class 220-1 within the first and second pluralities of filters 216, 222, respectively. Similarly, the second survey (e.g., the reassessment) also comprises a variety of questions associated with filters 216, 222 within a plurality of filters of a first category class 214-2 and a plurality of filters of a second category class 220-2, respectively. Answers to the questions in the second survey received by the device are run against filters of a first category class 214-2 and filters of a second category class 220-2, e.g., within the first and second pluralities of filters, respectively. Filters 216 of the first filter category class 214 are configured to terminate the qualification process when fired. Filters 222 of the second filter category class 220 are configured to provide the subject with a warning associated with a corresponding survey question. In other words, the device of FIG. 2 is configured to accumulate results from a survey (e.g., survey questions 208 and survey questions 212) and run the results against corresponding filters (e.g., filters 216 and filters 222, respectively) in order to determine if a subject is qualified for OTC delivery of a $PDE_5$ inhibitor pharmaceutical composition.

In the present disclosure, a plurality of filters refers to a series, or set, or filters in either the first filter category class or the second category class. For instance, in some embodiments, a plurality of filters of the first filter category class 214 can comprise any subset of filters 216 of the first filter category class. As an example, in some embodiments a plurality of filters of the first category class comprises filters 216-1, 216-2, 216-3, . . . , 216-i, or any combination thereof. Similarly, a plurality of filters of the second filter category class 220 can comprise any set of filters 222 of the second filter category class. Moreover, in some embodiments a plurality of filters of the second category class comprises filters 222-1, 222-2, 222-3, . . . , 222-i, or any combination thereof.

Continuing to refer to FIG. 2, in some embodiments, the dispensing device 250 comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the $PDE_5$ inhibitor pharmaceutical composition OTC dispensing device 250 but that can be electronically accessed by the $PDE_5$ inhibitor pharmaceutical composition OTC dispensing device 250 over an Internet, intranet, or other form of network or electronic cable (illustrated as element 106 in FIG. 2) using network interface 284.

In some embodiments, the memory 192 of the PDE$_5$ inhibitor pharmaceutical composition OTC dispensing device 250 stores one or more of:
- an operating system 202 that includes procedures for handling various basic system services;
- an assessment module 252 for qualifying a subject for an initial over-the-counter delivery of a PDE$_5$ inhibitor pharmaceutical composition to treat erectile dysfunction, by communicating survey questions, obtaining results therefrom, and applying the results to qualifying filters, the assessment module including:
  - a first filter category class 214-1, including filters 216 (e.g., a first plurality of filters), each respective filter 216 in the first filter category class 214-1 associated with one or more survey questions 208 and one or more triggering conditions 218;
  - a second filter category class 220-1, including filters 222 (e.g., a second plurality of filters), each respective filter 222 in the second filter category class 220-1 associated with one or more survey questions 208, triggering conditions 224, and warnings 226;
- a fulfillment module 228-1 for executing a fulfillment process when no filter 216 in the first filter category class 214-1 has been fired for a subject and the subject has acknowledged each warning 226 associated with each filter 222 in the second filter category class 220-1 that was fired as a result of answers by the subject to the survey questions 208, where the fulfillment process includes communicating an over-the-counter drug facts label 230 for the PDE$_5$ inhibitor pharmaceutical composition to the subject and receiving confirmation from the subject that the over-the-counter drug facts label has been received and read;
- a reassessment module 254 for qualifying a subject for a subsequent over-the-counter delivery of a PDE$_5$ inhibitor pharmaceutical composition to treat erectile dysfunction, by communicating survey questions, obtaining results therefrom, and applying the results to qualifying filters, the assessment module including:
  - a first filter category class 214-2, including filters 216 (e.g., a third plurality of filters), each respective filter 216 in the first filter category class 214-2 associated with one or more survey questions 208 and one or more triggering conditions 218;
  - a second filter category class 220-2, including filters 222 (e.g., a second plurality of filters), each respective filter 222 in the second filter category class 220-2 associated with one or more survey questions 208, triggering conditions 224, and warnings 226;
- a re-fulfillment module 228-2 for executing a re-fulfillment process when no filter 216 in the first filter category class 214-2 has been fired for a subject and the subject has acknowledged each warning 226 associated with each filter 222-2 in the second filter category class 220 that was fired as a result of answers by the subject to the survey questions 212, where the fulfillment process includes communicating an over-the-counter drug facts label 230 for the PDE$_5$ inhibitor pharmaceutical composition to the subject and receiving confirmation from the subject that the over-the-counter drug facts label has been received and read;
- a subject profile data store 232 comprising a user profile 234 for each of a plurality of subjects, each respective user profile 234 including information (e.g., shipping information, billing information, biometric information, etc.) about a corresponding subject in the plurality of subjects, an initial order date and destination 236, and any re-order date and the destination 238 for the PDE$_5$ inhibitor pharmaceutical composition made by the corresponding subject using the PDE$_5$ inhibitor pharmaceutical composition OTC dispensing device 250;
- an adverse event module 242 for identifying and aggregating records of adverse events associated with a plurality of subjects, e.g., corresponding to the firing of a filter 216 in the first filter category class 214-2 during a re-fulfillment process;
- a reimbursement module 240 for determining eligibility and/or communicating an insurance claim associated with delivery of the PDE$_5$ inhibitor, e.g., based on insurance information stored in a respective user profile 234.

In some embodiments, the assessment module 252, reassessment module 254, and/or fulfillment module 228 are accessible within any browser (e.g., phone, tablet, laptop/desktop, or smartwatch). In some embodiments, the assessment module 252, reassessment module 254, and/or fulfillment module 228 run on native device frameworks, and is available for download onto a user device 102 running an operating system 202 such as Android, iOS, or WINDOWS.

In some implementations, one or more of the above identified data elements or modules (e.g., assessment module 252, fulfillment module 228-1, etc.) of the PDE$_5$ inhibitor pharmaceutical composition OTC dispensing device 250 for qualifying a human subject for over-the-counter delivery of a PDE$_5$ inhibitor pharmaceutical composition to treat erectile dysfunction are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a PDE$_5$ inhibitor pharmaceutical composition OTC dispensing device 250 for qualifying a human subject for over-the-counter delivery of a PDE$_5$ inhibitor pharmaceutical composition to treat erectile dysfunction is a smart phone (e.g., an iPhone, Blackberry, etc.), a laptop, a tablet computer, a desktop computer, a smart watch, or another form of electronic device (e.g., a gaming console). In some embodiments, the PDE$_5$ inhibitor pharmaceutical composition OTC dispensing device 250 is not mobile. In some embodiments, the PDE$_5$ inhibitor pharmaceutical composition OTC dispensing device 250 is mobile.

In some embodiments, the PDE$_5$ inhibitor pharmaceutical composition OTC dispensing device 250 is not a smart phone but rather is a tablet computer, desktop computer, emergency vehicle computer, or other form or wired or wireless networked device. In the interest of brevity and clarity, only a few of the possible components of the PDE$_5$ inhibitor pharmaceutical composition OTC dispensing device 250 are shown in FIG. 2 in order to better emphasize the additional software modules that are installed on the PDE$_5$ inhibitor pharmaceutical composition OTC dispensing device 250.

Figure 3A:
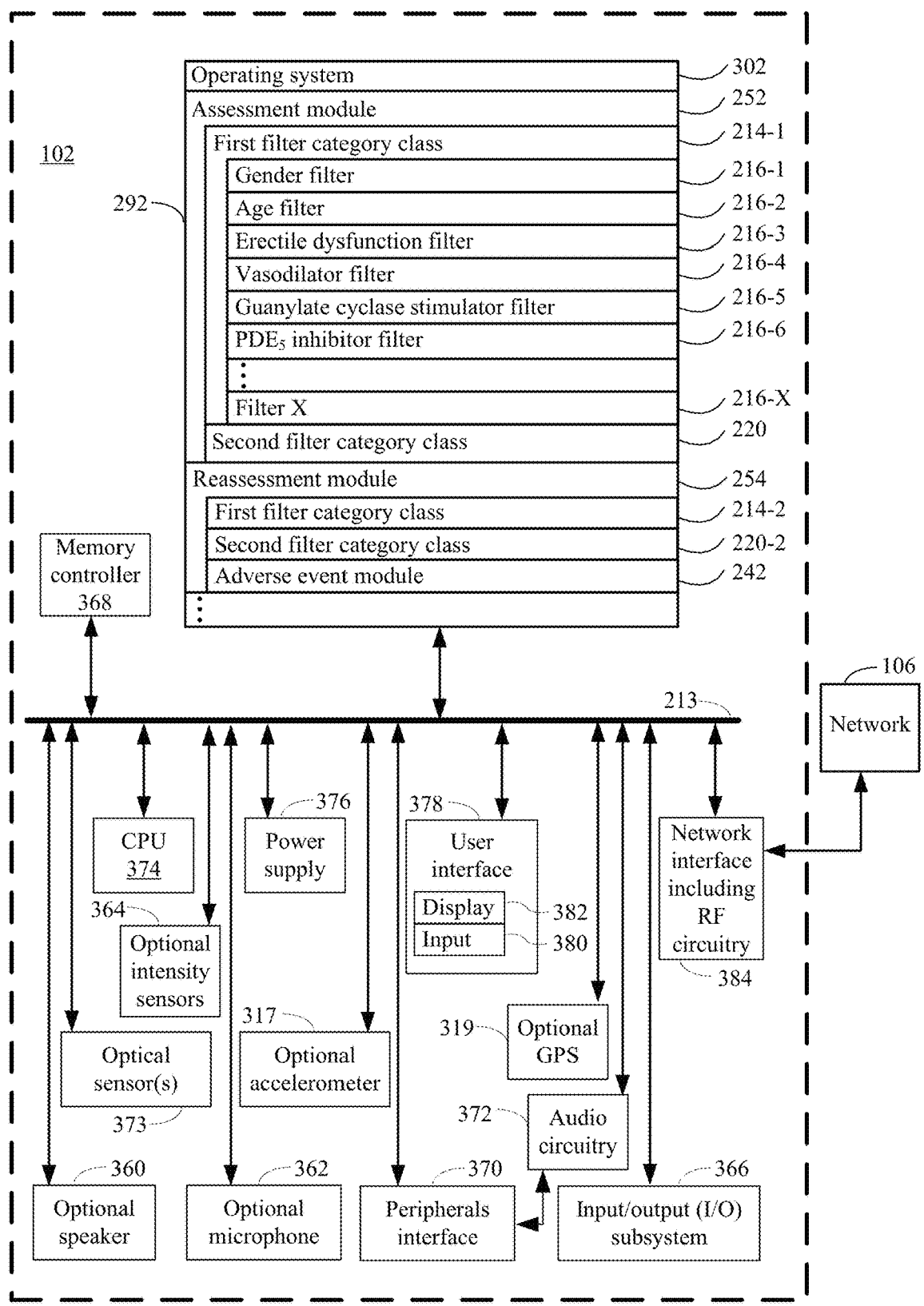
Figure 3B:
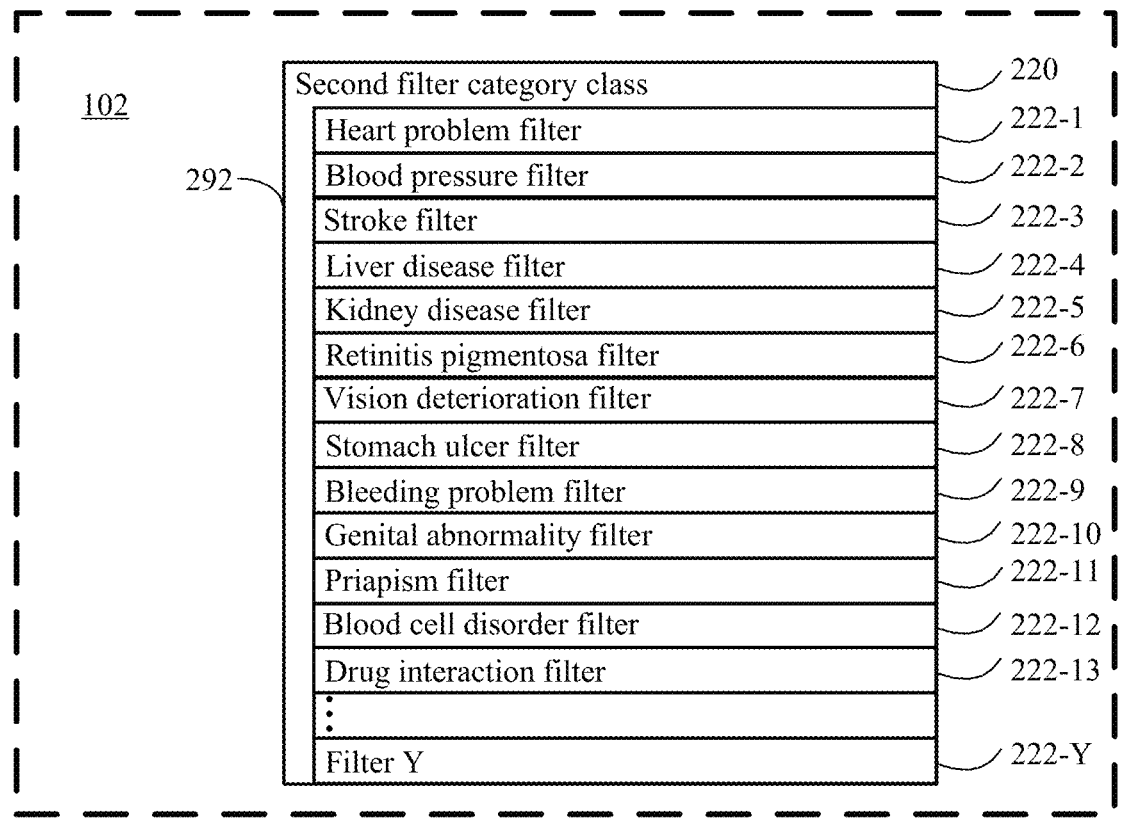

FIG. 3 provides a description of a user device 102 that can be used with the present disclosure. The user device 102 illustrated in FIG. 3 has one or more processing units (CPU's) 374, peripherals interface 370, memory controller 368, a network or other communications interface 384, a memory 392 (e.g., random access memory), a user interface 378, the user interface 378 including a display 382 and input 380 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the user device 102 (e.g., a touch-sensitive surface such as a touch-sensitive display system 382 of the user device 102), an optional input/output (I/O) subsystem 366, one or more optional optical sensors 373, one or more communication busses 313 for interconnecting the aforementioned components, and a power supply 376 for powering the aforementioned components.

In some embodiments, the input 380 is a touch-sensitive display, such as a touch-sensitive surface. In some embodiments, the user interface 378 includes one or more soft keyboard embodiments. The soft keyboard embodiments may include standard (e.g., QWERTY) and/or non-standard configurations of symbols on the displayed icons.

The user device 102 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the user device 102 and/or for determining an amount of physical exertion by the subject.

It should be appreciated that the user device 102 illustrated in FIG. 3 is only one example of a multifunction device that may be used for performing a survey (e.g., first survey 206) in order to qualify for over-the-counter delivery of a $PDE_5$ inhibitor pharmaceutical composition to treat erectile dysfunction, and that the user device 102 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 392 of the user device 102 illustrated in FIG. 3 optionally includes high-speed random access memory and optionally also includes non-volatile memory, such as one or more magnetic disk storage devices, flash memory devices, or other non-volatile solid-state memory devices. Access to memory 392 by other components of the $PDE_5$ inhibitor pharmaceutical composition OTC dispensing device 250, such as CPU(s) 374 is, optionally, controlled by the memory controller 368. In some embodiments, the memory 392 of the user device 102 illustrated in FIG. 3 optionally includes:
- an operating system 302 that includes procedures for handling various basic system services;
- the assessment module 252 described above in conjunction with the $PDE_5$ inhibitor composition OTC dispensing device 250;
- the first category class 214 described above in conjunction with the $PDE_5$ inhibitor pharmaceutical composition OTC dispensing device 250 further comprising a gender filter 216-1, an age filter 216-2, a first erectile dysfunction filter 216-3, a first vasodilator filter 216-4, a first guanylate cyclase filter 216-5, and a $PDE_5$ inhibitor filter 216-6; and
- the second category class 220 described above in conjunction with the $PDE_5$ inhibitor pharmaceutical composition OTC dispensing device 250 comprising a first heart disease filter 222-1, a first blood pressure filter 222-2, a first stroke filter 222-3, a first liver disease filter 222-4, a first kidney disease filter 222-5, a first retinitis pigmentosa filter 222-6, a first vision deterioration filter 222-7, a stomach ulcer filter 222-8, a first bleeding problem filter 222-9, a first genital abnormality filter 222-10, a first priapism filter 222-11, a first blood cell disorder filter 222-12, and a first drug interaction filter 222-13.

In some embodiments, the optional accelerometer 317, optional GPS 319, and/or magnetometer (not shown) of the user device 102 or such components are used to recommend to qualifying subjects one or more suitable destinations for delivery of the $PDE_5$ inhibitor pharmaceutical composition over-the-counter. In some embodiments, the GPS 319 is used to determine if a subject is geographically restricted for OTC delivery of the $PDE_5$ inhibitor pharmaceutical composition. Geographical restrictions include a subject residing outside of delivery or shipping regions, marketing restrictions, and/or government regulations.

The peripherals interface 370 can be used to couple input and output peripherals of the device to CPU(s) 374 and memory 392. The one or more processors 374 run or execute various software programs and/or sets of instructions stored in memory 392, such as the survey module 204, to perform various functions for the user device 102 and to process data.

In some embodiments, the peripherals interface 370, CPU(s) 374, and memory controller 368 are, optionally, implemented on a single chip. In some other embodiments, they are implemented on separate chips.

RF (radio frequency) circuitry of network interface 384 receives and sends RF signals, also called electromagnetic signals. In some embodiments, the survey module 204, survey questions 208/212, answers to survey questions 208/212, and/or the over-the-counter drug facts label 230 are communicated to the subject device 102 using this RF circuitry. In some embodiments, the RF circuitry 384 converts electrical signals to/from electromagnetic signals and communicates with communications networks and other communications devices and/or the data collection device 200 and/or the $PDE_5$ inhibitor pharmaceutical composition OTC dispensing device 250 via the electromagnetic signals. The RF circuitry 384 optionally includes well-known circuitry for performing these functions, including an antenna system, an RF transceiver, one or more amplifiers, a tuner, one or more oscillators, a digital signal processor, a CODEC chipset, a subscriber identity module (SIM) card, memory, and so forth. RF circuitry 384 optionally communicates with the communication network 106. In some embodiments, the circuitry 384 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the user device 102. The audio circuitry 372 receives audio data from the peripherals interface 370, converts the audio data to electrical signals, and transmits the electrical signals to the speaker 360. The speaker 360 converts the electrical signals to human-audible sound waves. In some embodiments, the speaker 260 converts the electrical signals to human-inaudible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 392 and/or the RF circuitry 384 by the peripherals interface 370.

In some embodiments, the power supply 376 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the user device 102 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the user device 102, opposite the display 382 on the front of the user device 102, so that the input 380 is enabled for use as a viewfinder for still and/or video image acquisition. In some embodiments, another optical sensor 373 is located on the front of the user device 102 so that the subject's image is obtained (e.g., to verify the health, condition, or identity of the subject as part of qualifying the subject for over-the-counter delivery of a $PDE_5$ inhibitor pharmaceutical composition to treat erectile dysfunction), to help diagnose a subject's condition remotely, or to acquire visual physiological measurements of the subject, etc.).

As illustrated in FIG. 3, the user device 102 preferably comprises an operating system 302 that includes procedures for handling various basic system services. The operating system 302 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the user device 102 is a smart phone or a smart watch. In other embodiments, the user device 102 is not a smart phone or a smart watch but rather is a tablet computer, a desktop computer, an emergency vehicle computer, or other form or wired or wireless networked device. In the interest of brevity and clarity, only a few of the possible components of the user device 102 are shown in FIG. 3 in order to better emphasize the additional software modules that are installed on the user device 102.

While the system 48 disclosed in FIG. 1 can work standalone, in some embodiments it can also be linked with electronic medical record systems to exchange information in any way.

Now that details of a system 48 for qualifying a human subject for over-the-counter delivery of a $PDE_5$ inhibitor pharmaceutical composition to treat erectile dysfunction have been disclosed, details regarding a method (400), including processes and features to be performed by the system, in accordance with an embodiment of the present disclosure, are disclosed with reference to FIGS. 4A through 4I. In some embodiments, such processes and features of the system are carried out by the assessment module 252, reassessment module 254, fulfillment module 228-1, and/or re-fulfillment module 228-2 illustrated in FIGS. 2 and 3. In some embodiments, the assessment module 252, reassessment module 254, fulfillment module 228-1, and/or reassessment module 228-2 are a single software module. In the flow chart, elements in dashed boxes are considered to be optional.

Blocks 402-408.

Referring to block 402 of FIG. 4A, a goal of the present disclosure is to qualify subjects for over-the-counter delivery of a $PDE_5$ inhibitor pharmaceutical composition to treat erectile dysfunction using a computer system such as a $PDE_5$ inhibitor pharmaceutical composition OTC dispensing device 250. The $PDE_5$ inhibitor pharmaceutical composition OTC dispensing device (e.g., device 250) comprises one or more processors (e.g., processor 274) and a memory (e.g., memory 192 and/or 290). The memory stores non-transitory instructions that, when executed by the one or more processors, perform a method.

Referring to block 404, in some embodiments the $PDE_5$ inhibitor pharmaceutical composition has the structure:

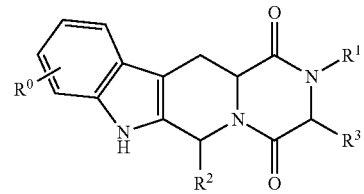

where, $R^0$ represents hydrogen, halogen or $C_{1-6}$ alkyl;

$R^1$ represents hydrogen, $C_{1-6}$ alkyl, $C_{2-6}$ alkenyl, $C_{2-6}$ alkynyl, halo$C_{1-6}$ alkyl, $C_{3-8}$ cycloalkyl, $C_{3-8}$ cycloalkyl-$C_{1-3}$ alkyl, aryl$C_{1-3}$ alkyl or heteroaryl$C_{1-3}$ alkyl;

$R^2$ represents an optionally substituted mono-cyclic aromatic ring selected from benzene, thiophene, furan and pyridine or an optionally substituted bicyclic ring

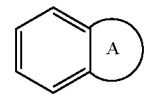

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and $R^3$ represents hydrogen or $C_{1-3}$ alkyl, or $R^1$ and $R^3$ together represent a 3- or 4-membered alkyl or alkenyl chain, or a pharmaceutically acceptable salt thereof.

Referring to blocks 406 and 408, in some embodiments the $PDE_5$ inhibitor pharmaceutical composition includes tadalafil. In some embodiments, the $PDE_5$ inhibitor includes a pharmaceutically acceptable salt of tadalafil.

In some embodiments, the $PDE_5$ inhibitor pharmaceutical composition includes vardenafil. These, and other, $PDE_5$ inhibitor compositions are described, for example, in Corbin, et al., "Pharmacology of Phosphodiesterase-5 Inhibitors," International Journal of Clinical Practice (2002), the content of which is hereby incorporated by reference.

In some embodiments, the $PDE_5$ inhibitor pharmaceutical composition includes any compound disclosed in U.S. Pat. No. 6,469,012, entitled "Pyrazolopyrimidinones for the Treatment of Impotence," which is hereby incorporated by reference. In some embodiments, the $PDE_5$ inhibitor pharmaceutical composition includes any compound disclosed in U.S. Pat. No. 5,250,534, entitled "Pyrazolopyrimidinone Antianginal Agents," which is hereby incorporated by reference. In some embodiments, the $PDE_5$ inhibitor pharmaceutical composition includes any compound disclosed in U.S. Pat. No. 6,140,329, entitled "Use of cGMP-Phosphodiesterase Inhibitors in Methods and Compositions to Treat Impotence," which is hereby incorporated by reference.

In some embodiments, the $PDE_5$ inhibitor pharmaceutical composition includes any compound disclosed in U.S. Pat. No. 6,566,360, entitled "2-phenyl Substituted Imidatriazinones as Phosphodiesterase Inhibitors," which is hereby incorporated by reference. In some embodiments, the $PDE_5$ inhibitor pharmaceutical composition includes any compound disclosed in U.S. Pat. No. 7,122,540, entitled "2-phenyl Substituted Imidatriazinones as Phosphodiesterase Inhibitors," which is hereby incorporated by reference.

In some embodiments, in response to receiving a first request from a user to be qualified for provision of a PDE5 inhibitor pharmaceutical composition, the system creates a corresponding subject profile, e.g., containing biographic information about the subject, e.g., one or more of a subject name, date of birth, residence, delivery address, social security number, medical record number, insurance information, user name, identification password, etc. In some embodiments, the system registers a subject that has not previously received an over-the-counter provision of a PDE5 inhibitor pharmaceutical composition as a new user of the PDE5 inhibitor pharmaceutical composition, and the device will perform an initial assessment method for qualifying the subject for a provision of the PDE5 inhibitor pharmaceutical composition, e.g., regardless of whether the subject previously received a provision of a PDE5 inhibitor pharmaceutical composition via prescription.

In some embodiments, the system registers a subject that has previously received a provision of a PDE5 inhibitor pharmaceutical composition via prescription as a previous user of the $PDE_5$ inhibitor pharmaceutical composition, and the device will perform a reassessment method for re-qualifying the subject for a provision of the PDE5 inhibitor pharmaceutical composition.

In some embodiments, where the subject previously received a provision of a different PDE5 inhibitor pharmaceutical composition via prescription, the system will perform a modified method for qualifying the subject for provision of the PDE5 inhibitor pharmaceutical composition that accounts for differences in the contraindications and risk factors of the two PDE5 inhibitor pharmaceutical compositions. For example, in response to receiving a request to qualify a user that previously received a provision of a pharmaceutical composition containing vardenafil via prescription, for an over-the-counter provision of sildenafil, the system performs a modified method for re-qualifying (e.g., a reassessment) the subject for the PDE5 inhibitor pharmaceutical composition that includes a survey question and corresponding filter relating to whether the subject has had a recent heart surgery (e.g., regardless of whether a reassessment for a pharmaceutical composition containing sildenafil would normally consider a subject's history of surgery), because that factor would not have been considered when the subject received the prescription for the composition containing vardenafil.

In some embodiments, in response to receiving a second or subsequent request from a user to be qualified for provision of a PDE5 inhibitor pharmaceutical composition, the system registers the subject as a returning customer, e.g., when the subject has previously received an over-the-counter provision of the PDE5 inhibitor and a corresponding subject profile 232 already exists for the subject.

Figure 7A:
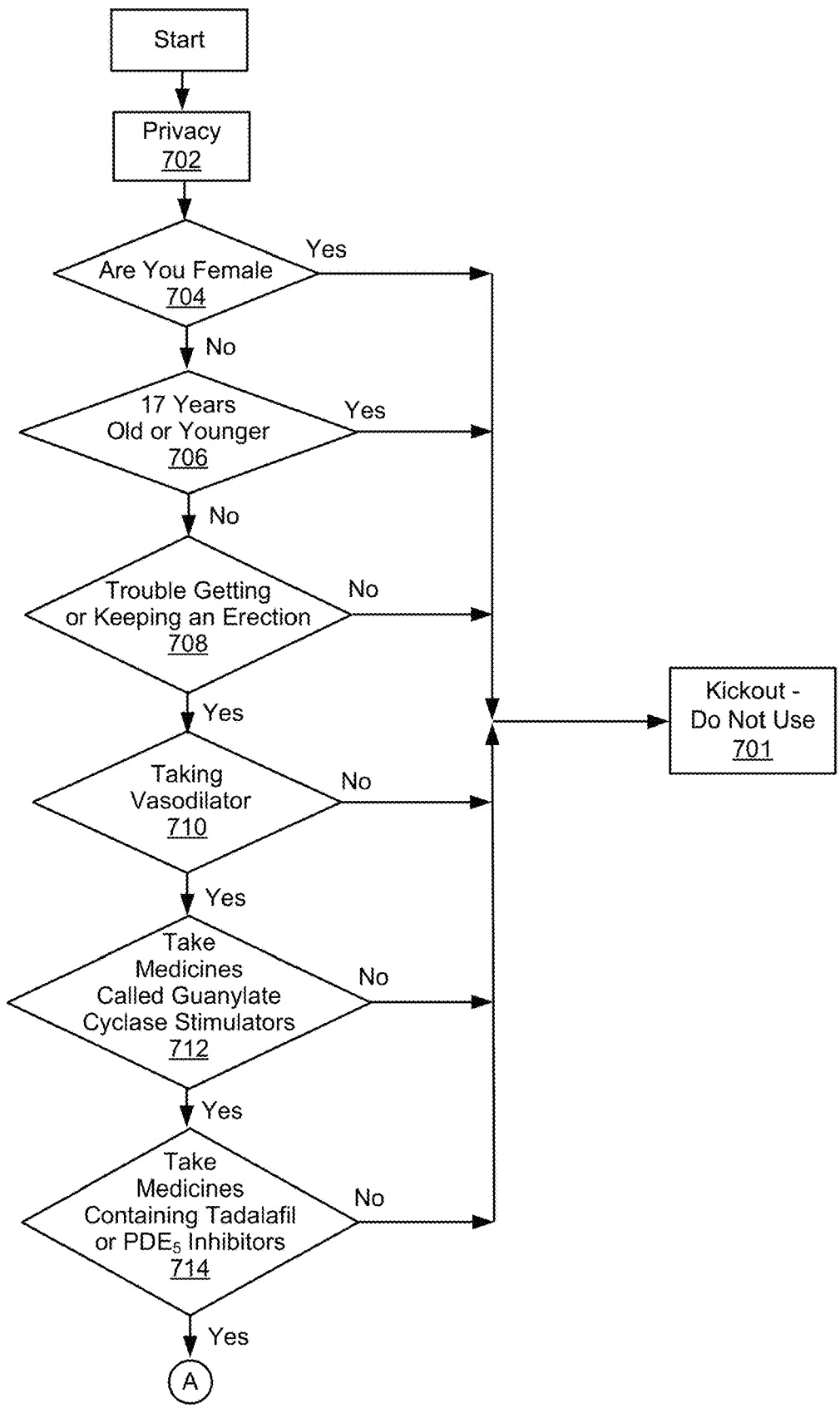
FIGS. 7A, 7B, 7C, and 7D collectively illustrate an example method for qualifying a subject for an over-the-counter provision of a PDE$_5$ inhibitor pharmaceutical composition in accordance with an embodiment of the present disclosure.

In some embodiments, prior to proceeding with the qualification or re-qualification method, the device prompts (702, 704) the user to confirm that they have adequate privacy to provide sensitive medical information (e.g., prompt 704 in FIG. 7A) and/or that they are in possession of medical information required to complete the qualification process (e.g., prompt 702 to confirm that they have knowledge of the required medical information required to completed the survey.

Blocks 410-412.

Referring to block 410 of FIG. 4A, the method includes conducting a first survey of the subject thereby obtaining a first plurality of survey results (e.g., to survey questions 208, 212 (e.g., one or more of the survey questions set forth in Table 1). In some embodiments, the device transmits one or more survey questions to the user, prompting a response, and then receives a response to the one or more survey questions back from the subject. In some embodiments, the first survey results include, or at least indicate, some or all of the subject characteristics listed in Table 1. For example, in some embodiments, the first plurality of survey results includes, or at least indicates, 2, 3, 4, 5, 6, 7, 8, 9, 10, 11, 12, 13, 14, 15, 16, 17, 18, or all 19 of the characteristics listed in Table 1. In one embodiment, the first survey questions 208, 212 and results include all of characteristics 1-19 as provided in Table 1.

Referring to block 412, e.g., as illustrated in FIG. 7, in some embodiments the first survey results indicate a gender of the subject (e.g., responsive to a survey 208, such as question 550, e.g., that is associated with and/or applied to (704) a gender filter 216-1 of a first category class 214-1), an age of the subject (e.g., responsive to a survey question 208 that is associated with and/or applied to (706) an age filter 216-2 of a first category class), an erectile dysfunction status of the subject (e.g., responsive to a survey question 208 that is associated with and/or applied to (708) an erectile dysfunction filter 216-3 of a first category class), whether the subject is taking a nitrate or nitrite vasodilator composition (e.g., responsive to a survey question 208 that is associated with and/or applied to (710) a vasodilator filter 216-4 of a first category class), whether the subject is taking a guanylate cyclase stimulator medication (e.g., responsive to a survey question 208 that is associated with and/or applied to (712) a guanylate cyclase stimulator filter 216-5 of a first category class), whether the subject is taking a $PDE_5$ inhibitor composition (e.g., responsive to a survey question 208 that is associated with and/or applied to (714) a $PDE_5$ inhibitor filter 216-6 of a first category class), whether the subject has ever had a heart problem (e.g., hospitalization for angina pectoris, coronary revascularization, myocardial infarction, cardiovascular death, resuscitated cardiac arrest, hospitalization for heart failure, stroke/TIA, or peripheral vascular disease) (e.g., responsive to a survey question 208 that is associated with and/or applied to (716) a heart problem filter 222-1 of a second category class 220-1), a blood pressure status of the subject (e.g., responsive to a survey question 208 that is associated with and/or applied to (718,720) a blood pressure filter 222-2 of a second category class), whether the subject has ever had a stroke (e.g., responsive to a survey question 208 that is associated with and/or applied to (722) a stroke filter 222-3 of a second filter class category), whether the subject has a liver problem (e.g., responsive to a survey question 208 that is associated with and/or applied to (724) a liver disease filter 222-4 of a second category class), a kidney function status of the subject (e.g., responsive to a survey question 208 that is associated with and/or applied to (726) a kidney disease filter 222-5 of a second category class), whether the subject has retinitis pigmentosa (e.g., responsive to a survey question 208 that is associated with and/or applied to (728) a retinitis pigmentosa filter 222-6 of a second category class), whether the subject has developed vision loss (e.g., responsive to a survey question 208 that is associated with and/or applied to (730) a vision deterioration filter 222-7 of a second category class), whether the subject has ever had a stomach ulcer (e.g., responsive to a survey question 208 that is associated with and/or applied to (732) a stomach ulcer filter 222-8 of a second category class), whether the subject has a bleeding disorder (e.g., responsive to a survey question 208 that is associated with and/or applied to (734) a bleeding problem filter 222-9 of a second category class), a genital status of the subject (e.g., responsive to a survey question 208 that is associated with and/or applied to (736) a genital abnormality filter 222-10 of a second category class), whether the subject has ever experienced priapism (e.g., responsive to a survey question 208 that is associated with and/or applied to (738) a priapism filter 222-11 of a second category class), whether the subject has a blood cell disorder (e.g., responsive to a survey question 208 that is associated with and/or applied to (740) a blood cell disorder filter 222-12 of a second category class), and whether the subject is taking a medication that interacts with the $PDE_5$ inhibitor pharmaceutical composition (e.g., responsive to a survey question 208 that is associated with and/or applied to (742-752) a drug interaction filter 222-13 of a second category class).

In some embodiments, the first survey includes questions that elicit responses providing or indicating some or all of the characteristics listed in Table 1. In some embodiments, the survey includes questions corresponding to each of the survey results required for the methods described herein. In other embodiments, the survey includes questions corresponding to only a subset of the survey results required for the methods described herein. In some embodiments, other survey results required for the methods described herein are acquired through other means (e.g., upon registration/subscription for a service associated with qualifying the subject for over-the-counter medication, from a healthcare provider, from a prior survey, from a database associated with a pharmacy, from an electronic health record associated with the subject, from the subject profile data store 232, etc.) For example, in some embodiments, the subject provides a personal medical identification associated with an insurer, a hospital, or other healthcare provider and information about the subject required for the methods described herein, e.g., one or more survey results, is acquired from a preexisting database associated with the personal medical identification (e.g., a last cholesterol or blood pressure measurement determined for the subject).

TABLE 1

Example subject characteristics for qualifying a subject for an over-the-counter provision of a $PDE_5$ inhibitor pharmaceutical composition

| Result | Example Characteristics |
|---|---|
| 1 | a gender of the subject |
| 2 | an age of the subject |
| 3 | an erectile dysfunction status of the subject |
| 4 | whether the subject is taking a nitrate or nitrite vasodilator composition |

TABLE 1-continued

Example subject characteristics for qualifying a subject for an over-the-counter provision of a $PDE_5$ inhibitor pharmaceutical composition

| Result | Example Characteristics |
|---|---|
| 5 | whether the subject is taking a guanylate cyclase stimulator medication |
| 6 | whether the subject is taking a $PDE_5$ inhibitor composition |
| 7 | whether the subject has ever had a heart problem, |
| 8 | a blood pressure status of the subject |
| 9 | whether the subject has ever had a stroke |
| 10 | whether the subject has a liver problem |
| 11 | a kidney function status of the subject |
| 12 | whether the subject has retinitis pigmentosa |
| 13 | whether the subject has developed vision loss or hearing loss |
| 14 | whether the subject has ever had a stomach ulcer |
| 15 | whether the subject has a bleeding disorder |
| 16 | a genital status of the subject |
| 17 | whether the subject has ever experienced priapism |
| 18 | whether the subject has a blood cell disorder |
| 19 | whether the subject is taking a medication that interacts with the $PDE_5$ inhibitor pharmaceutical composition |

It is contemplated that, in some embodiments, any one or more of the survey questions 208, 212 provided in Table 1 will not be included in the first survey (e.g., will not be used for the assessment. For example, in some embodiments, a characteristic associated with a particular survey questions will be informative when qualifying a subject for one particular $PDE_5$ inhibitor but not for another $PDE_5$ inhibitor.

Accordingly, it is contemplated that the first survey questions 208 include any subset of survey results provided in Table 1. For brevity, all possible combinations of survey questions 208, 212 eliciting the characteristics provided in Table 1 are not specifically delineated here. However, the skilled artisan will easily be able to envision any particular subset of the survey questions 208, 212 that elicit the characteristics provided in Table 1. Likewise, the skilled artisan may know of other survey questions, eliciting informative subject characteristics not provided in Table 1, that may be combined with any subset of survey questions that elicit subject characteristics provided in Table 1 to form the first survey questions used in the methods described herein.

In some embodiments, the first and/or second survey is conducted by transmitting a plurality of questions to the subject, e.g., some or all of the survey questions, and receiving answers to the plurality of survey questions before applying any of the answers to respective filters. For example, with reference to the workflow in FIG. 7, the device transmits questions relating to all of the filters of the first category class, all of the filters of the second category class, or all of the filters in the workflow (e.g., as a virtual survey where all of the questions are displayed in a single user interface, or as a series of questions displayed in consecutive user interfaces). After receiving answers to all of the survey questions, the device then applies the answers to all of the filters (e.g., sequentially or concurrently) to determine whether the subject is qualified to receive provision of the $PDE_5$ inhibitor pharmaceutical composition. In alternative embodiments, the device transmits questions relating to just those filters of the first category class for which it could not obtain answers to the questions from an electronic database associated with the subject, such as electronic health record of the subject, and just those filters of the second category class it could not obtain answers to the questions from an electronic database associated with the subject (e.g., as a virtual survey where such unanswered questions are displayed in a single user interface, or as a series of questions displayed in consecutive user interfaces). After receiving answers to all of the survey questions, the device then applies the answers to all of the filters (e.g., sequentially or concurrently) to determine whether the subject is qualified to receive provision of the $PDE_5$ inhibitor pharmaceutical composition.

Figures 5A, 5B:
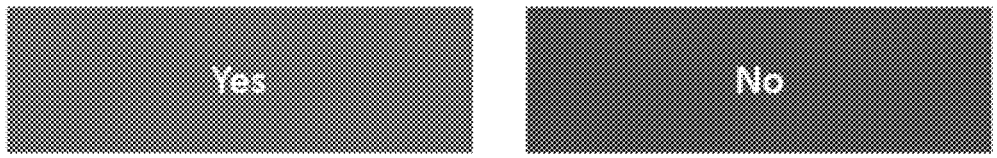
Figure 5C:
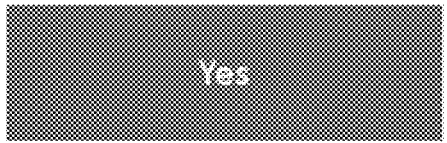
Figure 5C:
Figure 5D:
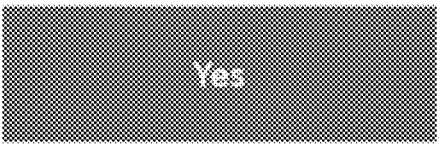
Figure 5D:
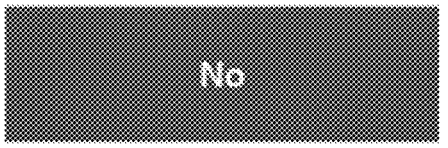
Figure 7B:
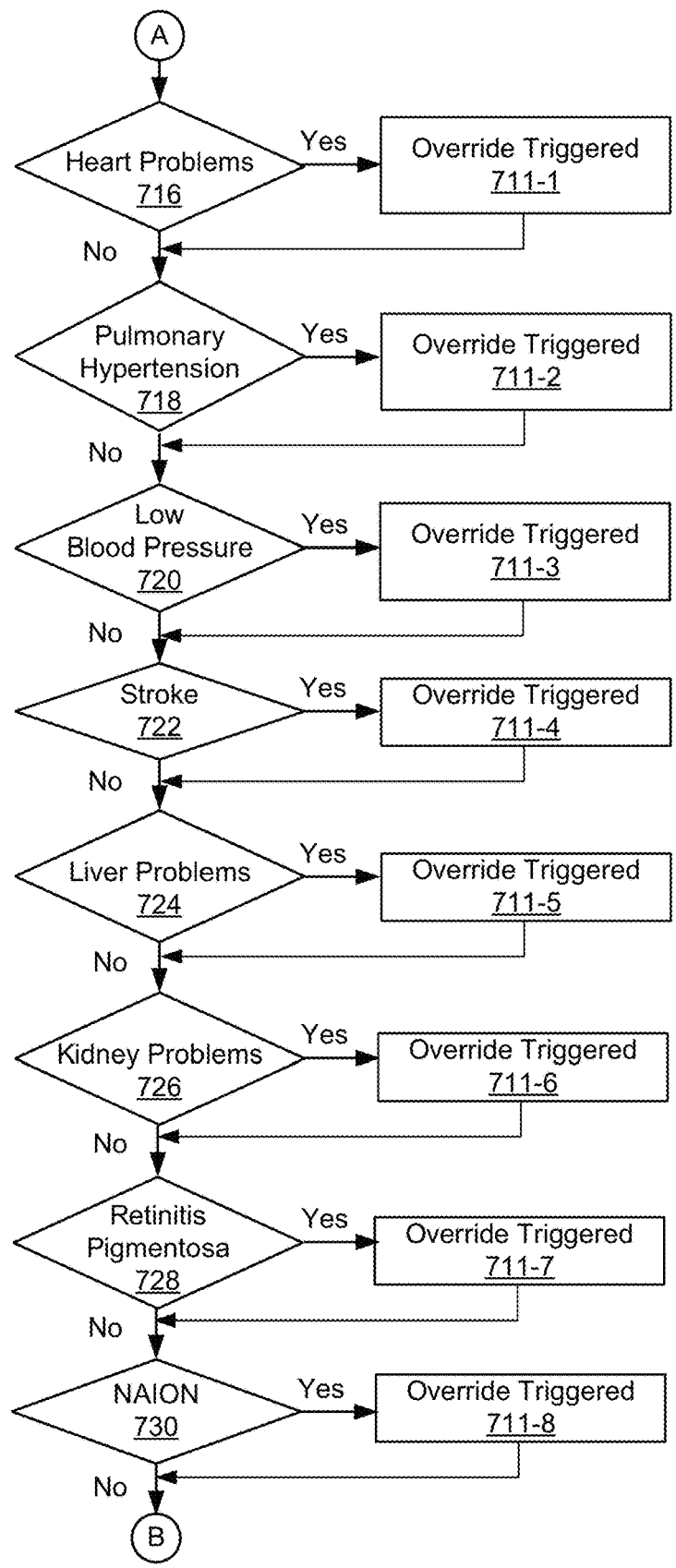
Figure 7C:
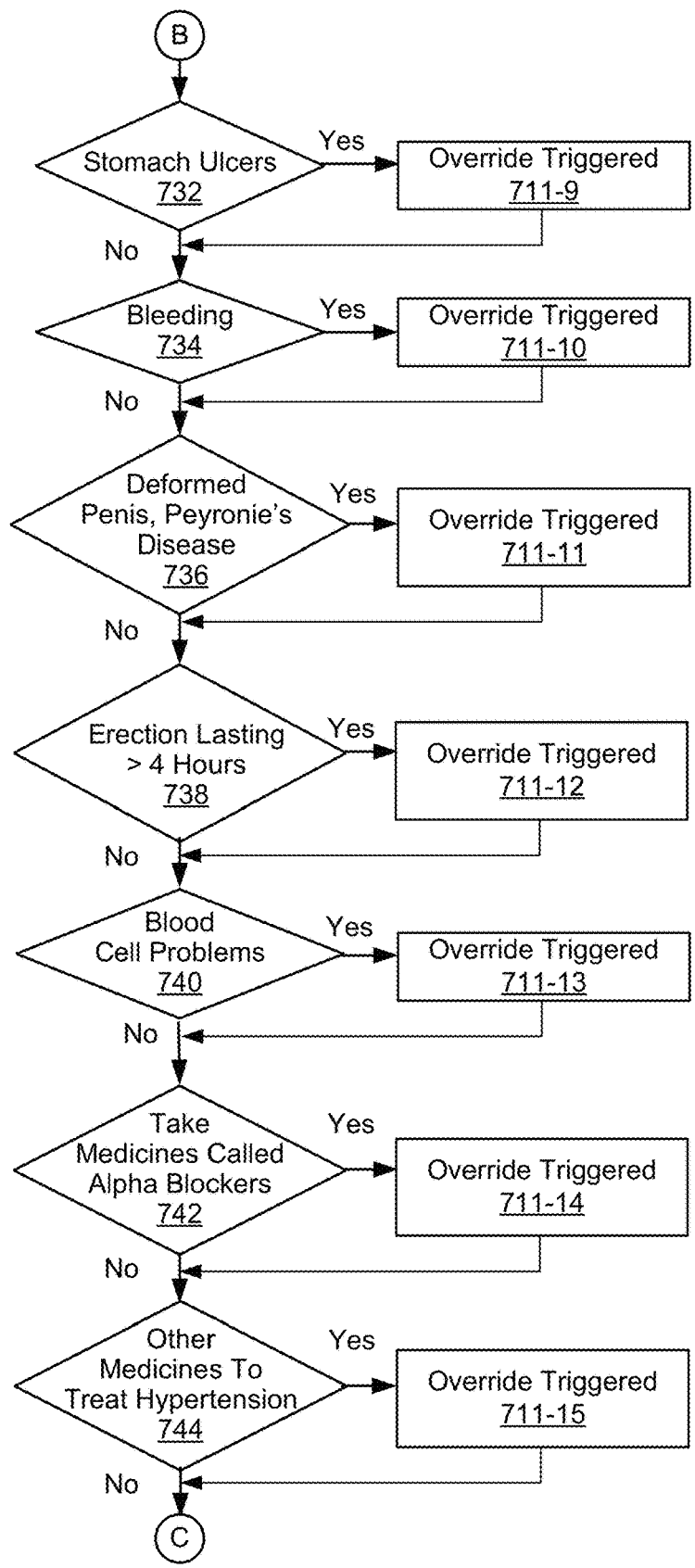

In some embodiments, the first and/or second survey is conducted in a serial fashion, e.g., by transmitting a first question or a first group of survey questions (e.g., associated with a single filter) to the subject, receiving an answer to the single survey question or small group of survey questions, and applying the answer or answers to a filter, prior to transmitting a second question or second group of questions to the subject. For example, with reference to the workflow in FIG. 7, in some embodiments the device transmits a first question to the subject, relating to the gender of the subject. After receiving the answer to the survey question, the device applies the answer to a gender filter (704). If the gender filter is fired (e.g., in response to a non-"male" answer), the device terminates (795-1) the process, and optionally provides the user with a message relating to why they are being denied a provision of the $PDE_5$ inhibitor pharmaceutical composition (e.g., as illustrated in FIG. 5B, message 552, advising the subject that taking the $PDE_5$ inhibitor pharmaceutical composition creates a risk when co-administered with other drugs), a suggestion for following-up with a medical professional (e.g., as illustrated in FIGS. 7B and 7C, when the survey answers indicate that the subject has experienced priapism (738), the device terminates the process (795-2) and advises that the subject seek immediate medical attention), and/or a suggestion to make a lifestyle change, to treat their erectile dysfunction.

Blocks 414-430.

Referring to block 418 of FIG. 4B, all or a portion of the first survey results are run against a first plurality of filters of a first category class 214. As previously described, the first plurality of filters includes a subset of filters 216 of the first filter category class 214. When a respective filter in the first plurality of filters is fired (e.g., when a survey result indicates that a triggering condition 218 has been met), the subject is deemed not qualified for delivery of the $PDE_5$ inhibitor pharmaceutical composition and the method is terminated without delivery of the $PDE_5$ inhibitor pharmaceutical composition.

In some embodiments, e.g., when the method is terminated without delivery of the $PDE_5$ inhibitor pharmaceutical composition, the subject is prevented from attempting to requalify for the $PDE_5$ inhibitor for a predetermined period of time (e.g., the subject is locked out). In some embodiments, the subject is prevented from attempting to requalify for the $PDE_5$ inhibitor after a predetermined number of qualification attempts. In some embodiments, the subject is prevented from attempting to requalify for the $PDE_5$ inhibitor after a failing to verify a communication (e.g., failing to verify a text message sent to the subject). This prevents the subject from abusing the systems and methods of the present disclosure.

Referring to blocks 416-430, specific filters 216 in the first plurality of filters and their exemplary triggering conditions 218 that cause the corresponding filter to fire are detailed.

In some embodiments, the first plurality of filters of the first category class 214 includes some or all of the filters 216 listed in Table 2. For example, in some embodiments, the first plurality of filters results includes 2, 3, 4, 5, or all 6 of the filters listed in Table 2.

TABLE 2

Example filters for contraindications associated with qualifying a subject for an over-the-counter provision of a $PDE_5$ inhibitor pharmaceutical composition

| Filter | Example Criteria |
|---|---|
| 1a | a gender filter |
| 2a | an age filter |
| 3a | an erectile dysfunction filter |
| 4a | a vasodilator filter |
| 5a | a guanylate cyclase filter |
| 6a | a $PDE_5$ inhibitor filter |

It is contemplated that, in some embodiments, any one or more of the filters 216 provided in Table 2 will not be included in the first plurality of filters. For example, in some embodiments, a characteristic associated with a particular survey result will be informative when qualifying a subject for one particular $PDE_5$ inhibitor but not for another $PDE_5$ inhibitor.

Accordingly, it is contemplated that the first plurality of filters includes any sub-set of filters 216 provided in Table 2. Likewise, the skilled artisan may know of other filters 216, not provided in Table 2, which may be combined with any subset of the filters 216 provided in Table 2 to form the first plurality of filters results used in the methods described herein. For brevity, all possible combinations of the filters 216 provided in Table 2 are not specifically delineated here.

Referring to block 416, in some embodiments the first plurality of filters includes a gender filter (e.g., gender filter 216-1 in FIG. 3 and/or filter 1a in Table 2). In some embodiments, the gender filter is configured to be fired when the first plurality of survey results indicates that the subject is female. In some embodiments, the gender filter is configured to be fired when the first plurality of survey results indicates that the subject is not male (e.g., the subject is female, the subject does not input a gender, the subject is transgender). If the gender filter is fired, the subject is not permitted to obtain the $PDE_5$ inhibitor pharmaceutical composition over-the-counter (e.g., the method is terminated without authorizing provision of the $PDE_5$ inhibitor pharmaceutical composition to the subject).

Referring to blocks 418-420, in some embodiments the first plurality of filters includes an age filter (e.g., age filter 216-2 in FIG. 3 and/or filter 2a in Table 2). In some embodiments, the age filter is fired when the first plurality of survey results indicates that the subject has not yet reach an age of maturity, e.g., is less than eighteen years old. If the age filter is fired, the subject is not permitted to obtain the $PDE_5$ inhibitor pharmaceutical composition over-the-counter (e.g., the method is terminated without authorizing provision of the $PDE_5$ inhibitor pharmaceutical composition to the subject).

Referring to block 422, in some embodiments the first plurality of filters includes an erectile dysfunction filter (e.g., erectile dysfunction filter 216-3 in FIG. 3 and/or filter 3a in Table 2). The erectile dysfunction filter is configured to be fired at least when the first plurality of survey results indicates that the subject does not have erectile dysfunction. If the erectile dysfunction filter is fired, the subject is not permitted to obtain the $PDE_5$ inhibitor pharmaceutical composition over-the-counter (e.g., the method is terminated without authorizing provision of the $PDE_5$ inhibitor pharmaceutical composition to the subject).

Referring to blocks 424-426, in some embodiments the first plurality of filters includes a vasodilator filter (e.g., vasodilator filter 216-4 in FIG. 3 and/or filter 4a in Table 2).

In some embodiments, the vasodilator filter is fired when the first plurality of survey results indicates that the subject is taking a vasodilator composition including a nitrate or a nitrite. In some embodiments, the vasodilator composition, which is capable of firing the first vasodilator filter, includes a compound selected from the group consisting of nitroglycerin, amyl nitrate, amyl nitrite, and butyl nitrate (block 426). In some embodiments, nitrate vasodilators are associated with the recreational drugs known as "popper(s)," which are nitric oxide donors. In some embodiments, the vasodilator filter is fired when the first plurality of survey results indicates that the subject is taking a drug known as "poppers". If the vasodilator filter is fired, the subject is not permitted to obtain the $PDE_5$ inhibitor pharmaceutical composition over-the-counter (e.g., the method is terminated without authorizing provision of the $PDE_5$ inhibitor pharmaceutical composition to the subject).

Referring to block 438, in some embodiments the first plurality of filters includes a guanylate cyclase stimulator filter (e.g., guanylate cyclase stimulator filter 216-5 in FIG. 3 and/or filter 5a in Table 2). The guanylate cyclase stimulator filter is configured to be fired at least when the first plurality of survey results indicates that the subject is taking a guanylate cyclase stimulator. In some embodiments, guanylate cyclase stimulators which are capable of firing the guanylate cyclase stimulator filter include riociquat and other medications that treat pulmonary arterial hypertension and/or chronic thromboembolic pulmonary hypertension. If the guanylate cyclase stimulator filter is fired, the subject is not permitted to obtain the $PDE_5$ inhibitor pharmaceutical composition over-the-counter (e.g., the method is terminated without authorizing provision of the $PDE_5$ inhibitor pharmaceutical composition to the subject).

Referring to block 430, in some embodiments the first plurality of filters includes a $PDE_5$ inhibitor filter (e.g., $PDE_5$ inhibitor filter 216-6 in FIG. 3 and/or filter 6a in Table 2). The $PDE_5$ inhibitor filter is configured to be fired at least when the first plurality of survey results indicates that the subject is taking a $PDE_5$ inhibitor. If the $PDE_5$ inhibitor filter is fired, the subject is not permitted to obtain the $PDE_5$ inhibitor pharmaceutical composition over-the-counter (e.g., the method is terminated without authorizing provision of the $PDE_5$ inhibitor pharmaceutical composition to the subject).

Figure 7D:
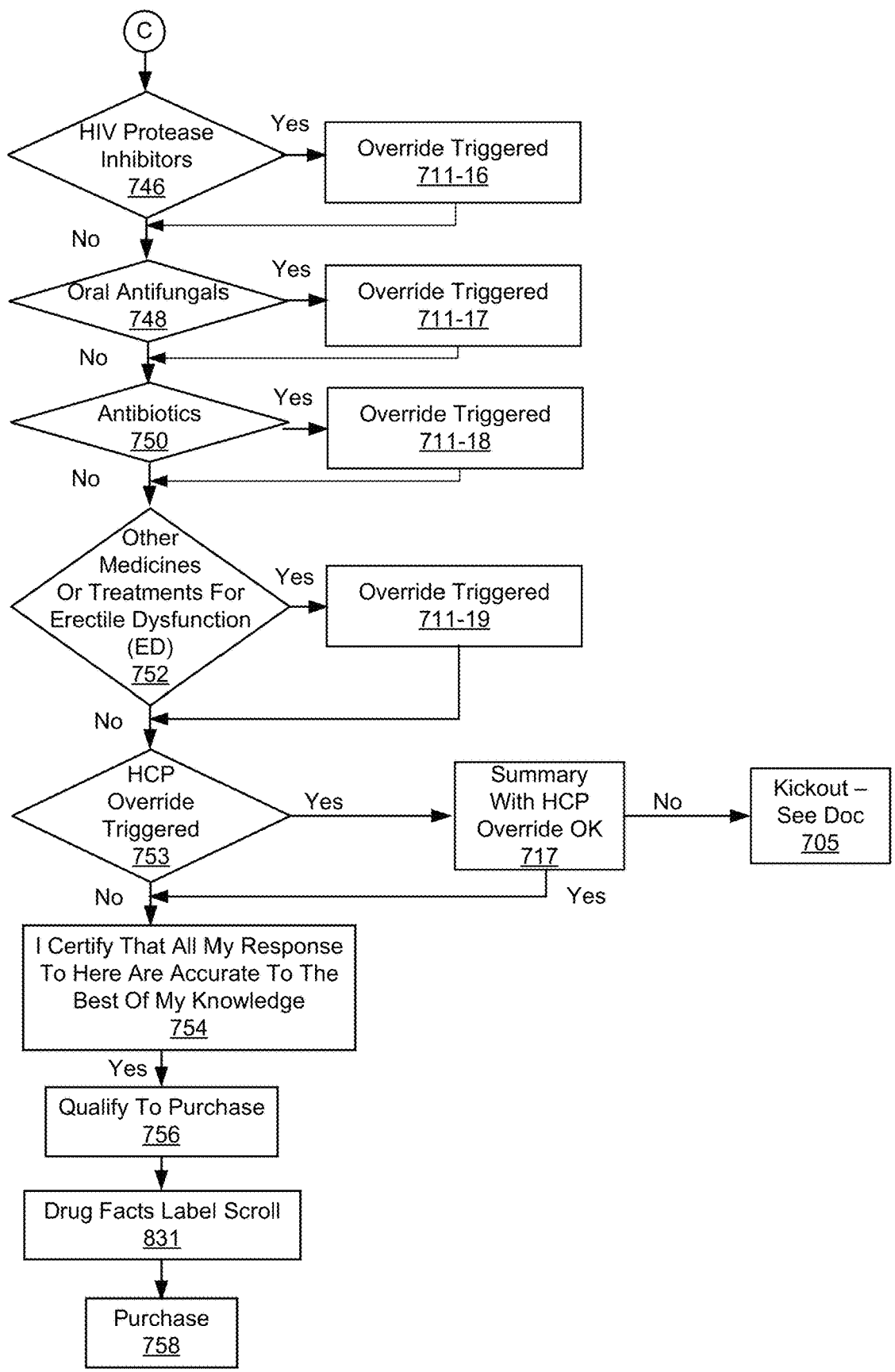

Referring to block 432 of FIG. 4C, the method also includes running all or a portion of the first survey results against a second plurality of filters of a second category class 220. When a respective filter in the second plurality of filters is fired, the subject is provided with a warning 226 corresponding to the respective filter (e.g., filter warning 226-4 corresponds to filter 222-4). In some embodiments, the warning 226 is provided as a next step, e.g., prior to applying survey results to any subsequent filters, after the corresponding filter is fired. For example, with respect to FIG. 7C, in some embodiments, e.g., when the priapism filter is triggered at 738, the device would provide the subject with a warning prior to proceeding to the blood cell disorder filter at 740, e.g., requiring the subject confirm they have discussed their history of priapism with a health care provider, e.g., and the healthcare provider still recommends taking a $PDE_5$ inhibitor pharmaceutical composition in order to proceed with the qualification. In some embodiments the warning 226 is provided after applying survey results to all subsequent filters. For example, as illustrated in FIGS. 7C and 7D, in some embodiments, e.g., when the priapism filter is triggered at 738, the device would proceed to the blood cell disorder filter at 740 prior to transmitting a warning to the subject, and then transmit all warnings corresponding to filters of the second category class, at 754, after survey results have been applied to all subsequent filters.

In some embodiments, the second plurality of filters 222 of the second category class 220 includes some or all of the filters listed in Table 3. For example, in some embodiments, the first plurality of filters results includes 2, 3, 4, 5, 6, 7, 8, 9, 10, 11, 12, or all 13 of the filters listed in Table 3. In one embodiment, the first plurality of filters includes all of filters 1-13 as provided in Table 3.

TABLE 3

Example filters for risk factors associated with qualifying a subject for an over-the-counter provision of a $PDE_5$ inhibitor pharmaceutical composition

| Filter | Example Criteria |
|---|---|
| 1a | a heart problem filter |
| 2a | a blood pressure filter |
| 3a | a stroke filter |
| 4a | a liver disease filter |
| 5a | a kidney disease filter |
| 6a | a retinitis pigmentosa filter |
| 7a | a vision deterioration filter |
| 8a | a stomach ulcer filter |
| 9a | a bleeding problem filter |
| 10a | a genital abnormality filter |
| 11a | a priapism filter |
| 12a | a blood cell disorder filter |
| 13a | a drug interaction filter |

Referring to blocks 434 and 436, in some embodiments, the second plurality of filters includes a heart problem filter (e.g., heart problem filter 222-1 in FIG. 3 and/or filter 1a in Table 3). The heart problem filter is configured to be fired at least when the first plurality of survey results indicate that the subject has had a heart problem. In some embodiments, heart problems that are capable of triggering the first heart filter include a heart attack, a heart failure, irregular heartbeats, arrhythmia, angina, chest pain, and/or narrowing of the aortic valve (block 436). In some embodiments, heart problems that are capable of triggering the first heart filter include palpitations, tachycardia, angina pectoris, myocardial infarction, and/or ventricular tachyarrhythmia. When the heart problem filter is fired, the device transmits a warning corresponding to the heart problem filter, and requires the user to acknowledge the warning before authorizing a provision of the $PDE_5$ inhibitor pharmaceutical composition.

Referring to block 438, in some embodiments, the second plurality of filters includes a blood pressure filter (e.g., blood pressure filter 222-2 in FIG. 3 and/or filter 2a in Table 3). The blood pressure filter is configured to be fired at least when the first plurality of survey results indicates that the subject has either low blood pressure, or uncontrolled high blood pressure. In some embodiments, the blood pressure filter is configured to be fired at least when the first plurality of survey results indicates that the subject has pulmonary hypertension. In some embodiments, the low pressure, which is capable of firing the blood pressure filter, is a blood pressure less than 90/50 mm Hg. In some embodiments, the low pressure, which is capable of firing the blood pressure filter, is a blood pressure greater than 170/110 mm Hg. In some embodiments, blood pressure cutoffs, or ranges, defining when the blood pressure filter is fired or when the blood pressure filter is not fired are determined according to a set of healthcare guidelines, which may change over time, and/or vary on a jurisdiction-by-jurisdiction basis. For example, in the United States, the American College of Cardiology and the American Heart Association collaborated to provide guidance on management of high blood pressure. Whelton P K, et al., J Am Coll Cardiol., S0735-1097(17)41519-1 (2017), the contents of which are hereby expressly incorporated by reference. These guidelines change over time as medical research and advances in treatment better inform management of high and low blood pressure. When the blood pressure filter is fired, the device transmits a warning corresponding to the blood pressure filter, and requires the user to acknowledge the warning before authorizing a provision of the $PDE_5$ inhibitor pharmaceutical composition.

Referring to block 440, in some embodiments, the second plurality of filters includes a stroke filter (e.g., stroke filter 222-3 in FIG. 3 and/or filter 3a in Table 3). The stroke filter is configured to be fired at least when the first plurality of survey results indicates that the subject has had a stroke. When the stroke filter is fired, the device transmits a warning corresponding to the stroke filter, and requires the user to acknowledge the warning before authorizing a provision of the $PDE_5$ inhibitor pharmaceutical composition.

Referring to block 442, in some embodiments, the second plurality of filters includes a liver disease filter (e.g., liver disease filter 222-4 in FIG. 3 and/or filter 4a in Table 3). In some embodiments, liver problems that are capable of triggering the first liver disease filter include impaired hepatic function, acute liver failure, and cholestasis. When the liver disease filter is fired, the device transmits a warning corresponding to the liver disease filter, and requires the user to acknowledge the warning before authorizing a provision of the $PDE_5$ inhibitor pharmaceutical composition.

Referring to block 444, in some embodiments, the second plurality of filters includes a kidney disease filter (e.g., kidney disease filter 222-5 in FIG. 3 and/or filter 5a in Table 3). The kidney disease filter is configured to be fired at least when the first plurality of survey results indicates that the subject has a kidney problem. In some embodiments, symptoms of kidney problems which are capable of firing the kidney function filter include nausea, loss of appetite, and/or fatigue. When the kidney disease filter is fired, the device transmits a warning corresponding to the kidney disease filter, and requires the user to acknowledge the warning before authorizing a provision of the $PDE_5$ inhibitor pharmaceutical composition.

Referring to block 446, in some embodiments, the second plurality of filters includes a retinitis pigmentosa filter (e.g., retinitis pigmentosa filter 222-6 in FIG. 3 and/or filter 6a in Table 3). The retinitis pigmentosa filter is configured to be fired at least when the first plurality of survey results indicates that the subject has retinitis pigmentosa. When the retinitis pigmentosa filter is fired, the device transmits a warning corresponding to the retinitis pigmentosa filter, and requires the user to acknowledge the warning before authorizing a provision of the $PDE_5$ inhibitor pharmaceutical composition.

Referring to block 448, in some embodiments, the second plurality of filters includes a vision deterioration filter (e.g., vision deterioration filter 222-7 in FIG. 3 and/or filter 7a in Table 3). The vision deterioration filter is configured to be fired at least when the first plurality of survey results indicates that the subject has had severe vision loss. In some embodiments, severe vision loss includes a non-arteritic anterior ischemic optic neuropath (NAION). In some embodiments, severe vision loss includes visual disturbances, ocular hyperemia, visual color distortions, eye pain, eye discomfort, photophobia, an increase in intraocular pressure, and/or conjunctivitis. When the vision deterioration filter is fired, the device transmits a warning corresponding to the vision deterioration filter, and requires the user to acknowledge the warning before authorizing a provision of the $PDE_5$ inhibitor pharmaceutical composition.

Referring to block 450, in some embodiments, the second plurality of filters includes a stomach ulcer filter (e.g., stomach ulcer filter 222-8 in FIG. 3 and/or filter 8a in Table 3). The stomach ulcer filter is configured to be fired at least when the first plurality of survey results indicates that the subject has had a stomach ulcer. When the stomach ulcer filter is fired, the device transmits a warning corresponding to the stomach ulcer filter, and requires the user to acknowledge the warning before authorizing a provision of the $PDE_5$ inhibitor pharmaceutical composition.

Referring to block 452, in some embodiments, the second plurality of filters includes a bleeding problem filter (e.g., bleeding problem filter 222-9 in FIG. 3 and/or filter 9a in Table 3). The bleeding problem filter is configured to be fired at least when the first plurality of survey results indicates that the subject has a bleeding disorder. In some embodiments, bleeding disorders include significant active peptic ulceration. When the bleeding problem filter is fired, the device transmits a warning corresponding to the bleeding problem filter, and requires the user to acknowledge the warning before authorizing a provision of the $PDE_5$ inhibitor pharmaceutical composition.

Referring to block 454, in some embodiments, the second plurality of filters includes a genital abnormality filter (e.g., genital abnormality filter 222-10 in FIG. 3 and/or filter 10a in Table 3). The genital abnormality filter is configured to be fired at least when the first plurality of survey results indicates that the subject has an abnormal penile shape. In some embodiments, a condition which is capable of firing the genital abnormality filter includes angulation, cavernosal fibrosis, or Peyronie's disease. When the genital abnormality filter is fired, the device transmits a warning corresponding to the genital abnormality filter, and requires the user to acknowledge the warning before authorizing a provision of the $PDE_5$ inhibitor pharmaceutical composition.

Referring to block 456 of FIG. 4D, in some embodiments, the second plurality of filters includes a priapism filter (e.g., priapism filter 222-11 in FIG. 3 and/or filter 11a in Table 3). The priapism filter is configured to be fired at least when the first plurality of survey results indicates that the subject has developed, or experienced, priapism (e.g., an erection that lasted for four hours or more). When the priapism filter is fired, the device transmits a warning corresponding to the priapism filter, and requires the user to acknowledge the warning before authorizing a provision of the $PDE_5$ inhibitor pharmaceutical composition.

Referring to block 458, in some embodiments, the second plurality of filters includes a blood cell disorder filter (e.g., blood cell disorder filter 222-12 in FIG. 3 and/or filter 12a in Table 3). The blood cell disorder filter is configured to be fired at least when the first plurality of survey results indicates that the subject has had a blood cell disorder. In some embodiments, blood cell disorders include sickle cell anemia, multiple myeloma, and leukemia. When the blood cell disorder filter is fired, the device transmits a warning corresponding to the blood cell disorder filter, and requires the user to acknowledge the warning before authorizing a provision of the $PDE_5$ inhibitor pharmaceutical composition.

Referring to blocks 460 and 462, in some embodiments, the second plurality of filters includes a drug interaction filter (e.g., drug interaction filter 222-13 in FIG. 3 and/or filter 13a in Table 3). The drug interaction filter is configured to be fired at least when the first plurality of survey results indicates that the subject indicates that the subject is taking a medication that interacts (e.g., a pharmacokinetic interaction and/or a pharmacodynamic interaction) with the $PDE_5$ inhibitor pharmaceutical composition. In some embodiments, the drug interaction filter is fired when the first plurality of survey results indicates that the subject is taking a medication selected from the group consisting of an alpha blocker (e.g., terazosin, tamsulosin, doxazosin mesylate, prazosin HCl, alfuzosin, dutasteride and tamsulosin HCl, and silodosin), an HIV protease inhibitor (e.g., ritonavir), an antifungal medication (e.g., ketoconazole and itraconazole), an antibiotic (e.g., clarithromycin, telithromycin, and erythromycin), a blood pressure medication (e.g., a medication to treat hypertension), and an erectile dysfunction medication (block 462). When the drug interaction filter is fired, the device transmits a warning corresponding to the drug interaction filter, and requires the user to acknowledge the warning before authorizing a provision of the $PDE_5$ inhibitor pharmaceutical composition.

The identity of drugs that are capable of triggering the drug interaction filter vary from one $PDE_5$ inhibitor to another $PDE_5$ inhibitor. The skilled artisan will know of drugs that interact with one $PDE_5$ inhibitor but not another. Inclusion of a drug within the drug interaction filter is dependent upon the identity and/or the dosage of the $PDE_5$ inhibitor pharmaceutical composition being authorized for over-the-counter use.

In some implementations, a drug that interacts with a $PDE_5$ inhibitor pharmaceutical composition is included within a filter 216 in the first filter category class 214, rather than within drug interaction filter 222 of the second filter category class 220. For example, according to some implementations, a particular drug included in drug-interaction filter 222 (e.g., as a risk factor) for a first $PDE_5$ inhibitor pharmaceutical composition, but included in a filter in the first plurality of filters (e.g., as a contraindication) for a second $PDE_5$ inhibitor pharmaceutical composition. However, a person skilled in the art will know whether to include a certain drug within drug interaction filter 222 or as a separate filter 216 in the first plurality of filters, based on the severity and risk of the drug interaction with the particular identity and dosage of the $PDE_5$ inhibitor being authorized for over-the-counter use.

It is contemplated that, in some embodiments, any one or more of the filters provided in Table 3 will not be included in the second plurality of filters. For example, in some embodiments, a characteristic associated with a particular survey result will be informative when qualifying a subject for one particular PDE5 inhibitor pharmaceutical composition but not for another $PDE_5$ inhibitor pharmaceutical composition. Accordingly, it is contemplated that the second plurality of filters includes any sub-set of filters provided in Table 3. Likewise, the skilled artisan may know of other filters, not provided in Table 3, that may be combined with any subset of the filters provided in Table 3 to form the second plurality of filters results used in the methods described herein.

Contraindications and risk factors described in the present disclosure are non-exhaustive. The skilled artisan may know of other contraindications for a particular the $PDE_5$ inhibitor pharmaceutical composition and/or treat risk factors as contraindications dependent upon the intended use of the $PDE_5$ inhibitor pharmaceutical composition. In some embodiments, contraindications for use of a prescription-strength pharmaceutical agent are treated only as risk factors, or not at all, when qualifying a subject for a lower-dose OTC use of a PDE5 inhibitor pharmaceutical composition.

Accordingly, it will be appreciated that the survey questions 208, 212, and filters 216, 222 applied to the survey answers thereof, may vary depending upon the $PDE_5$ inhibitor pharmaceutical composition being distributed. This is due to differences in the contraindication profiles of the various the $PDE_5$ inhibitor pharmaceutical compositions, e.g., due to different drug-drug interactions, routes of drug clearance, etc. of the different the $PDE_5$ inhibitor.

Figure 6:
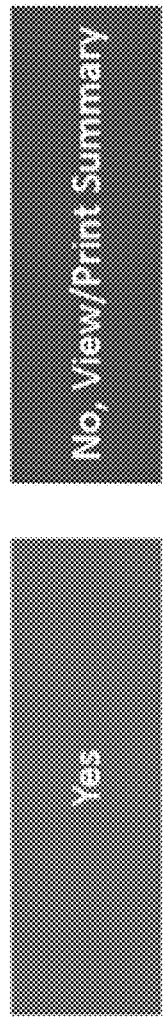
FIG. 6 illustrates feedback from a first survey in accordance with an embodiment of the present disclosure.

Referring to block 464, in some embodiments the warning 226 corresponding to a respective filter 222 in the second plurality of filters includes a prompt for the subject to indicate whether they have discussed the risk factor underlying the respective filter in the second plurality of filters that was fired with a health care practitioner (e.g., a licensed medical practitioner), e.g., and the health care practitioner indicated that the subject should take a $PDE_5$ inhibitor pharmaceutical composition in view of the underlying risk factor. Accordingly, acknowledgement is obtained from the subject when the subject indicates that they have discussed the risk factor underlying the respective filter in the second plurality of filters that was fired with a health care provider. For example, message 602 in FIG. 6 illustrates an example warning that is generic to any fired filters. In some embodiments, the warning is specific to a particular filter (e.g., filter warning 226 in FIG. 2), e.g., communicating to the user why the filter was fired.

In some embodiments, an acknowledgment from the user is verified by the health care practitioner (e.g., the method requires verification in order for authorization of the provision of the $PDE_5$ inhibitor pharmaceutical composition), e.g., in order to verify an accuracy of the survey results of the subject. In some embodiments, e.g., when the acknowledgment is verified by the heath care practitioner, the subject is deemed a trusted subject, such that verification of future results is not required.

Referring to block 466, the method includes obtaining acknowledgment from the subject for any warning 226 issued to the subject by any filter 222 in the second plurality of filters. In some embodiments, acknowledgment from the subject is a written acknowledgement, a verbal acknowledgment, or an electronic acknowledgment such as an electronic signature. If a filter 216 in the first plurality of filters fires, the subject is denied access to the over-the-counter $PDE_5$ inhibitor pharmaceutical composition.

Blocks 468-478.

Referring to block 468 of FIG. 4E, the process control proceeds to the fulfillment process when no filter 216 in the first plurality of filters has been fired and the subject has acknowledged each warning 226 associated with each filter 222 in the second plurality of filters that was fired. In some embodiments, the fulfillment process includes storing an indication in a user profile 234 of an initial order date and/or destination for the $PDE_5$ inhibitor pharmaceutical composition. The initial order date is utilized, for example, to verify at least a refill status of a provision of the $PDE_5$ inhibitor. The initial order date is also utilized, for example, to verify at least an elapsed period of time between an initial order and a future re-order. Such verification is required in order to ensure that certain tests (e.g., blood pressure tests) are taken regularly.

The fulfillment process further includes communicating an over-the-counter drug facts label 230 for the $PDE_5$ inhibitor pharmaceutical composition to the subject. In some embodiments, the drug facts label is communicated to the subject in real-time, e.g., within the same user interface as used for the qualification process. In some embodiments, the over-the-counter drug facts label 230 specifies what the $PDE_5$ inhibitor is for (e.g., to treat erectile dysfunction etc.), what dosage the subject is being authorized to take, and/or and any risks associated with taking $PDE_5$ inhibitor pharmaceutical composition (e.g., drug-drug interactions, pharmacokinetic interactions, adverse reactions, etc.).

In some embodiments, upon confirmation from the subject that the over the counter drug facts label 230 has been received and read, the subject is authorized for provision of a dosage of from 2.5 mg to 20 mg of tadalafil no more than once per day. In some embodiments, upon confirmation from the subject that the over the counter drug facts label 230 has been received and read, the subject is authorized for provision of a dosage of from 2.5 mg to 10 mg of tadalafil no more than once per day (block 472). In some embodiments, upon confirmation from the subject that the over the counter drug facts label 230 has been received and read, the subject is authorized for provision of a dosage of from 5 mg to 20 mg of tadalafil no more than once per day. In some embodiments, upon confirmation from the subject that the over the counter drug facts label 230 has been received and read, the subject is authorized for provision of a dosage of 2.5 mg of tadalafil no more than once per day. In some embodiments, upon confirmation from the subject that the over the counter drug facts label 230 has been received and read, the subject is authorized for provision of a dosage of 5 mg of tadalafil no more than once per day (block 474). In some embodiments, upon confirmation from the subject that the over the counter drug facts label 230 has been received and read, the subject is authorized for provision of a dosage of 10 mg of tadalafil no more than once per day. In some embodiments, upon confirmation from the subject that the over the counter drug facts label 230 has been received and read, the subject is authorized for provision of a dosage of 20 mg of tadalafil no more than once per day.

In some embodiments, upon confirmation from the subject that the over the counter drug facts label 230 has been received and read, the subject is authorized for provision of a dosage of from 2.5 mg to 20 mg of vardenafil no more than once per day. In some embodiments, upon confirmation from the subject that the over the counter drug facts label 230 has been received and read, the subject is authorized for provision of a dosage of from 2.5 mg to 10 mg of vardenafil no more than once per day. In some embodiments, upon confirmation from the subject that the over the counter drug facts label 230 has been received and read, the subject is authorized for provision of a dosage of from 5 mg to 20 mg of vardenafil no more than once per day. In some embodiments, upon confirmation from the subject that the over the counter drug facts label 230 has been received and read, the subject is authorized for provision of a dosage of 2.5 mg of vardenafil no more than once per day. In some embodiments, upon confirmation from the subject that the over the counter drug facts label 230 has been received and read, the subject is authorized for provision of a dosage of 5 mg of vardenafil no more than once per day. In some embodiments, upon confirmation from the subject that the over the counter drug facts label 230 has been received and read, the subject is authorized for provision of a dosage of 10 mg of vardenafil no more than once per day. In some embodiments, upon confirmation from the subject that the over the counter drug facts label 230 has been received and read, the subject is authorized for provision of a dosage of 20 mg of vardenafil no more than once per day.

Referring to blocks 476 and 478, in some embodiments the fulfillment process further includes authorizing provision of the $PDE_5$ inhibitor pharmaceutical composition to the subject. The authorization occurs upon confirmation from the subject that the over-the-counter drug facts label 230 has been received and read by the subject. In some embodiments, this authorization includes a destination associated with the subject. In some embodiments, the destination associated with the subject is stored in the user profile 234 (block 476). In some embodiments, the destination associated with the subject is a physical address including a street address, a Post Office box, a pharmacy associated with the subject, a health care provider associated with the subject, and/or one or more coordinates (e.g., longitude, latitude, elevation). In some embodiments, the provision of the $PDE_5$ inhibitor pharmaceutical composition to the subject comprises shipping the $PDE_5$ inhibitor pharmaceutical composition to the physical address associated with the subject (block 478). In some embodiments, the provision of the $PDE_5$ inhibitor pharmaceutical composition to the subject comprises shipping the $PDE_5$ inhibitor pharmaceutical composition to a pharmacy associated and/or a location associated with a health care provider of the subject and/or an office of a medical practitioner associated with the subject.

Blocks 480-514.

Referring to blocks 480-514 of FIGS. 4F-4I, a re-fulfillment process will be described infra. In some embodiments, the present disclosure provides a method for qualifying a subject for a refill of a $PDE_5$ inhibitor pharmaceutical composition. In some embodiments, the qualification for a refill of the $PDE_5$ inhibitor pharmaceutical composition follows an initial qualification of the subject, as described herein. In some embodiments, the qualification for a refill of the $PDE_5$ inhibitor pharmaceutical composition follows issuance of a prescription to the subject for the $PDE_5$ inhibitor pharmaceutical composition. For example, in some embodiments, a subject who is new to the qualification process is asked whether they previously received a prescription for the $PDE_5$ inhibitor pharmaceutical composition and, if the subject indicates that they have not previously received a prescription, the subject is directed to an initial qualification method and, if the subject indicates that they have previously received a prescription, the subject is directed to the refill qualification method, e.g., as described below.

Figure 4F:
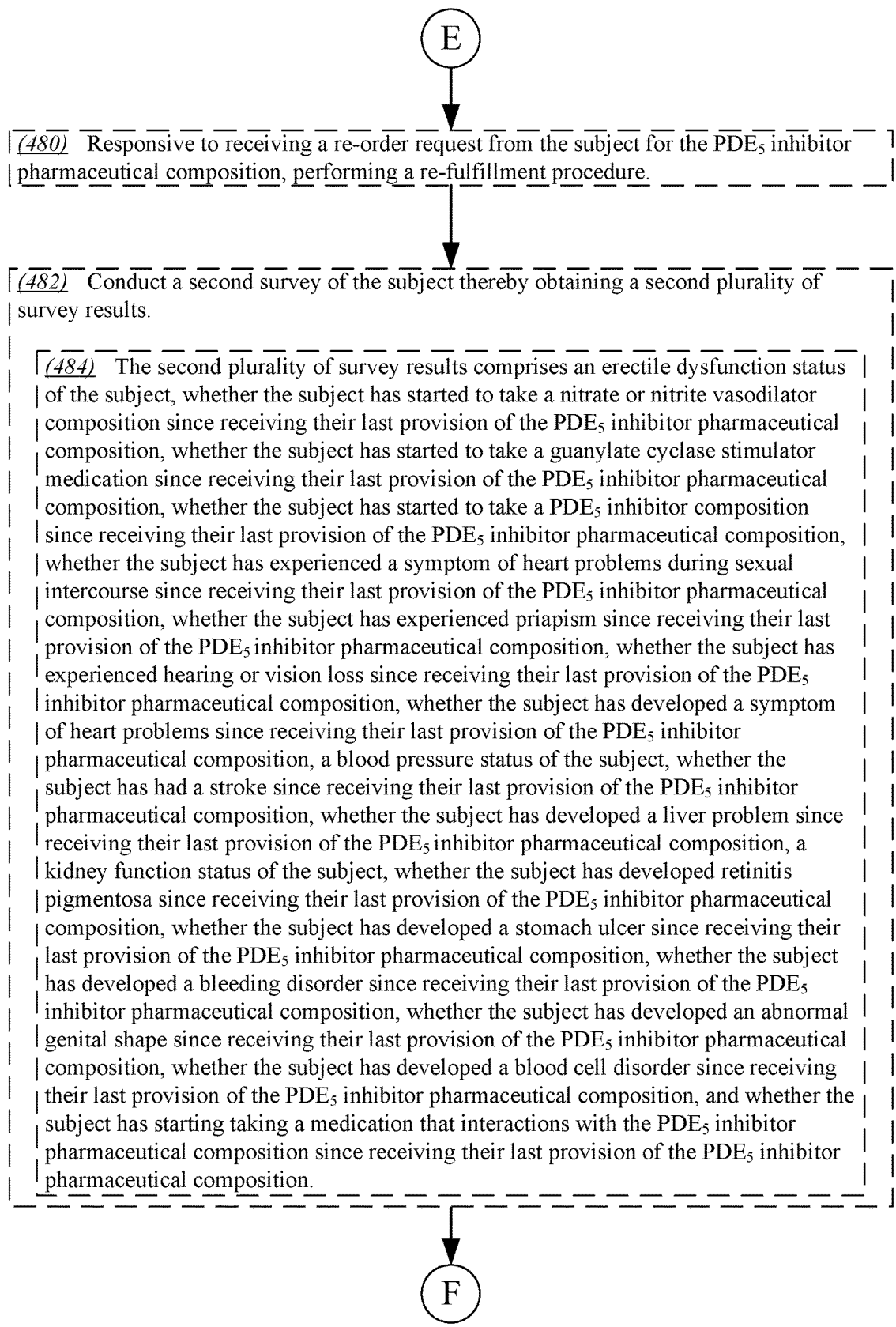

Referring to block 480 of FIG. 4F, in some embodiments a re-fulfillment procedure is performed. The re-fulfillment procedure is responsive to receiving a re-order request from the subject for the $PDE_5$ inhibitor pharmaceutical composition. In some embodiments, a prompt to initiate the re-fulfillment procedure is sent to user device 102 associated with the subject after a predetermined amount of time associated with a duration of dosages previously delivered to the subject (e.g., the user is reminded to fulfill their order of the $PDE_5$ inhibitor pharmaceutical composition just before, or just after, the user is scheduled to run out of a previously delivered provision).

Referring to blocks 482-484, in some embodiments the re-fulfillment procedure includes conducting a second survey of the subject. The second survey is configured to obtain a second plurality of survey results. These results are derived from corresponding survey questions (e.g., the device transmits one or more survey questions to the user, prompting a response, and then receives a response to the one or more survey questions back from the subject). In some embodiments, the second plurality of survey results include, or at least indicate, some or all of the subject characteristics listed in Table 4. For example, in some embodiments, the second plurality of survey results includes, or at least indicates, 1, 2, 3, 4, 5, 6, 7, 8, 9, 10, 11, 12, 13, 14, 15, 16, 17, or all 18 of the characteristic listed in Table 4. In one embodiment, the second survey questions and results include at least characteristics 1-17 as provided in Table 4.

In some embodiments, the second survey results indicate at least one of: an erectile dysfunction status of the subject (e.g., responsive to a survey question that is associated with and/or applied to (804) an erectile dysfunction filter 216-7 of a first category class 214-2), whether the subject has started to take a nitrate or nitrite vasodilator composition since receiving their last provision of the $PDE_5$ inhibitor pharmaceutical composition (e.g., responsive to a survey question that is associated with and/or applied to (806, 808) a vasodilator filter 216-8 of a first category class), whether the subject has started to take a guanylate cyclase stimulator medication since receiving their last provision of the $PDE_5$ inhibitor pharmaceutical composition (e.g., responsive to a survey question that is associated with and/or applied to (810) a guanylate cyclase stimulator filter 216-9 of a first category class), whether the subject has started to take a $PDE_5$ inhibitor composition since receiving their last provision of the $PDE_5$ inhibitor pharmaceutical composition (e.g., responsive to a survey question that is associated with and/or applied to (812) a $PDE_5$ inhibitor filter 216-10 of a first category class), whether the subject has developed symptoms of heart problems during sexual intercourse since receiving their last provision of the $PDE_5$ inhibitor pharmaceutical composition (e.g., responsive to a survey question that is associated with and/or applied to (814) a sexual intercourse filter 216-11 of a first category class), whether the subject has experienced priapism since receiving their last provision of the $PDE_5$ inhibitor pharmaceutical composition (e.g., responsive to a survey question that is associated with and/or applied to (816) a priapism filter 216-12 of a first category class), whether the subject has developed hearing or vision loss since receiving their last provision of the $PDE_5$ inhibitor pharmaceutical composition (e.g., responsive to a survey question that is associated with and/or applied to (818,820) a sensory deterioration filter 216-13 of a first category class), whether the subject has developed a symptom of heart problems since receiving their last provision of the $PDE_5$ inhibitor pharmaceutical composition (e.g., responsive to a survey question that is associated with and/or applied to (822) a heart problem filter 222-14 of a second category class 220-2), a blood pressure status of the subject (e.g., responsive to a survey question that is associated with and/or applied to (824,826) a blood pressure filter 222-15 of a second category class), whether the subject has had a stroke since receiving their last provision of the $PDE_5$ inhibitor pharmaceutical composition (e.g., responsive to a survey question that is associated with and/or applied to (828) a stroke filter 222-16 of a second category class), whether the subject has developed a liver problem since receiving their last provision of the $PDE_5$ inhibitor pharmaceutical composition (e.g., responsive to a survey question that is associated with and/or applied to (830) a liver disease filter 222-17 of a second category class), a kidney function status of the subject (e.g., responsive to a survey question that is associated with and/or applied to (832) a kidney disease filter 222-18 of a second category class), whether the subject has developed retinitis pigmentosa since receiving their last provision of the $PDE_5$ inhibitor pharmaceutical composition (e.g., responsive to a survey question that is associated with and/or applied to (834) a retinitis pigmentosa filter 222-19 of a second category class), whether the subject has developed a stomach ulcer since receiving their last provision of the $PDE_5$ inhibitor pharmaceutical composition (e.g., responsive to a survey question that is associated with and/or applied to (836) a stomach ulcer filter 222-20 of a second category class), whether the subject has developed a bleeding disorder since receiving their last provision of the $PDE_5$ inhibitor pharmaceutical composition (e.g., responsive to a survey question that is associated with and/or applied to (838) a bleeding problem filter 222-21 of a second category class), whether the subject has developed an abnormal genital shape since receiving their last provision of the $PDE_5$ inhibitor pharmaceutical composition (e.g., responsive to a survey question that is associated with and/or applied to (840) a genital abnormality filter 222-22 of a second category class), whether the subject has developed a blood cell disorder since receiving their last provision of the $PDE_5$ inhibitor pharmaceutical composition (e.g., responsive to a survey question that is associated with and/or applied to (842) a blood cell disorder filter 222-23 of a second category class), and whether the subject has started taking a medication that interacts with the $PDE_5$ inhibitor pharmaceutical composition since receiving their last provision of the $PDE_5$ inhibitor pharmaceutical composition (e.g., responsive to a survey question that is associated with and/or applied to (844-854) a drug interaction filter 222-24 of a second category class).

In some embodiments, the second survey includes questions that elicit responses providing some or all of the characteristics listed in Table 4. In some embodiments, the second survey includes questions corresponding to each of the survey results required for the methods described herein. In other embodiments, the second survey includes questions corresponding to only a subset of the survey results required for the methods described herein. In some embodiments, other survey results required for the methods described herein are acquired through other means (e.g., upon registration/subscription for a service associated with qualifying the subject for over-the-counter medication, from a healthcare provider, from a prior survey, from a database associated with a pharmacy, etc.) For example, in some embodiments, the subject provides a personal medical identification associated with an insurer, a hospital, or other healthcare provider and information about the subject required for the methods described herein, e.g., one or more survey results, is acquired from a preexisting database associated with the personal medical identification (e.g., a blood pressure measurement determined for the subject).

TABLE 4

Example characteristics for re-qualifying a subject for an over-the-counter provision of a $PDE_5$ inhibitor pharmaceutical composition.

| Result | Example Characteristics |
|---|---|
| 1 | an erectile dysfunction status of the subject |
| 2 | whether the subject has started to take a nitrate or nitrite vasodilator composition |
| 3 | whether the subject has started to take a guanylate cyclase stimulator medication |
| 4 | whether the subject has started to take a $PDE_5$ inhibitor composition |
| 5 | whether the subject has developed symptoms of heart problems during sexual intercourse |
| 6 | whether the subject has experienced priapism |
| 7 | whether the subject has developed hearing or vision loss |
| 8 | whether the subject has developed a symptom of heart problems |
| 9 | a blood pressure status of the subject |
| 10 | whether the subject has had a stroke |
| 11 | whether the subject has developed a liver problem |

TABLE 4-continued

Example characteristics for re-qualifying a subject for an over-the-counter provision of a PDE$_5$ inhibitor pharmaceutical composition.

| Result | Example Characteristics |
|---|---|
| 12 | a kidney function status of the subject |
| 13 | whether the subject has developed retinitis pigmentosa |
| 14 | whether the subject has developed a stomach ulcer |
| 15 | whether the subject has developed a bleeding disorder |
| 16 | whether the subject has developed an abnormal genital shape |
| 17 | whether the subject has developed a blood cell disorder since |
| 18 | whether the subject has started taking a medication that interacts with the PDE$_5$ |

It is contemplated that, in some embodiments, any one or more of the survey questions provided in Table 4 will not be included in the second survey (e.g., will not be used for the reassessment). For example, in some embodiments, a characteristic associated with a particular survey questions will be informative when qualifying a subject for one particular PDE$_5$ inhibitor but not for another PDE$_5$ inhibitor. For instance, a survey question is queried for tadalafil qualifying surveys but not for vardenafil qualifying surveys. The skilled artisan will recognize that different PDE$_5$ inhibitor carry different risk and drug interaction profiles. Accordingly, survey information required for qualifying a subject for access to one PDE$_5$ inhibitor with a known adverse drug interaction may not be necessary for qualifying the same subject for access to a second PDE$_5$ inhibitor.

Accordingly, it is contemplated that the second survey questions elicit responses to any sub-set of survey results provided in Table 4. For brevity, all possible combinations of the characteristics provided in Table 4 are not specifically delineated here. However, the skilled artisan will easily be able to envision any particular subset of survey questions designed to elicit responses to any subset of characteristics provided in Table 4. Likewise, the skilled artisan may know of other survey questions, not provided in Table 4, that may be combined with any subset of the survey questions provided in Table 4 to form the second survey questions used in the methods described herein.

Referring to block 486 of FIG. 4G, all or a portion the results are run against a third plurality of filters of the first category class. When a respective filter in the third plurality of filters is fired (e.g., when a survey result indicates that a triggering condition 218 has been met), the subject is deemed not qualified for the PDE$_5$ inhibitor pharmaceutical composition and the method is terminated without delivery of the PDE$_5$ inhibitor pharmaceutical composition.

Referring to blocks 488-500, specific filters in the third plurality of filters and their exemplary triggering conditions that cause the corresponding filter to fire are detailed.

In some embodiments, the third plurality of filters of the first category class 214 includes some or all of the filters 216 listed in Table 5. For example, in some embodiments, the first plurality of filters results includes 2, 3, 4, 5, 6, or all 7 of the filters listed in Table 5. In one embodiment, the third plurality of filters includes all of filters 1-7 as provided in Table 5.

TABLE 5

Example filters for contraindications associated with re-qualification of a subject for an over-the-counter provision of a PDE$_5$ inhibitor pharmaceutical composition.

| Filter | Example Criteria |
|---|---|
| 1a | an erectile dysfunction filter |
| 2a | a vasodilator filter |
| 3a | a guanylate filter |
| 4a | a PDE$_5$ inhibitor filter |
| 5a | a sexual intercourse filter |
| 6a | a priapism filter |
| 7a | a sensory deterioration filter |

It is contemplated that, in some embodiments, any one or more of the filters provided in Table 5 will not be included in the third plurality of filters. For example, in some embodiments, a characteristic associated with a particular survey result will be informative when qualifying a subject for one particular PDE$_5$ inhibitor but not for another PDE$_5$ inhibitor. Likewise, the skilled artisan may know of other filters, not provided in Table 5, which may be combined with any subset of the filters provided in Table 5 to form the third plurality of filters results used in the methods described herein. For brevity, all possible combinations of the filters provided in Table 5 are not specifically delineated here.

Referring to block 488, in some embodiments the third plurality of filters includes an erectile dysfunction filter, e.g., as described above in relation to the first survey. In some embodiments, the erectile dysfunction filter is configured to be fired at least when the second plurality of survey results indicates that the subject does not have erectile dysfunction. When the erectile dysfunction filter is fired, the subject is not permitted to obtain the PDE$_5$ inhibitor pharmaceutical composition over-the-counter (e.g., the method is terminated without authorizing re-provision of the PDE$_5$ inhibitor pharmaceutical composition to the subject). In some embodiments, the second plurality of survey results indicates that the subject does not have erectile dysfunction when the survey results indicate that the subject did not have erectile dysfunction since receiving their last provision of the PDE$_5$ inhibitor pharmaceutical composition. For instance, in some embodiments a subject does not have erectile dysfunction but is still recommended to obtain a PDE$_5$ inhibitor composition.

Referring to block 490, in some embodiments the third plurality of filters includes a vasodilator filter, e.g., as described above in relation to the first survey. In some embodiments, the vasodilator filter is configured to be fired at least when the second plurality of survey results indicates that the subject has been taking a vasodilator composition including a nitrate or a nitrite (e.g., nitroglycerin, alkyl nitrite, amyl nitrate, amyl nitrite, butyl nitrite, etc.) When the vasodilator filter is fired, the subject is not permitted to obtain the PDE$_5$ inhibitor pharmaceutical composition over-the-counter (e.g., the method is terminated without authorizing re-provision of the PDE$_5$ inhibitor pharmaceutical composition to the subject). In some embodiments, the second plurality of survey results indicates that the subject is taking a vasodilator composition comprising a nitrate or a nitrite when the survey results indicate that the subject was taking a vasodilator composition comprising a nitrate or a nitrite since receiving their last provision of the PDE$_5$ inhibitor pharmaceutical composition.

Referring to block 492, in some embodiments the third plurality of filters includes a guanylate cyclase stimulator filter, e.g., as described above in relation to the first survey.

In some embodiments, the guanylate cyclase stimulator filter is configured to be fired at least when the second plurality of survey results indicates that the subject is taking a guanylate cyclase stimulator mediation. When the guanylate cyclase stimulator filter is fired, the subject is not permitted to obtain the $PDE_5$ inhibitor pharmaceutical composition over-the-counter (e.g., the method is terminated without authorizing re-provision of the $PDE_5$ inhibitor pharmaceutical composition to the subject). In some embodiments, the second plurality of survey results indicates that the subject is taking a guanylate cyclase stimulator mediation when the survey results indicate that the subject was taking a guanylate cyclase stimulator mediation since receiving their last provision of the $PDE_5$ inhibitor pharmaceutical composition.

Referring to block 494, in some embodiments the third plurality of filters includes a $PDE_5$ inhibitor filter, e.g., as described above in relation to the first survey. In some embodiments, the $PDE_5$ inhibitor filter is configured to be fired at least when the second plurality of survey results indicates that the subject is taking a $PDE_5$ inhibitor composition. When the $PDE_5$ inhibitor filter is fired, the subject is not permitted to obtain the $PDE_5$ inhibitor pharmaceutical composition over-the-counter (e.g., the method is terminated without authorizing re-provision of the $PDE_5$ inhibitor pharmaceutical composition to the subject). In some embodiments, the second plurality of survey results indicates that the subject is taking a $PDE_5$ inhibitor composition when the survey results indicate that the subject is taking a $PDE_5$ inhibitor composition since receiving their last provision of the $PDE_5$ inhibitor pharmaceutical composition.

Referring to block 496, in some embodiments the third plurality of filters includes a sexual intercourse filter. In some embodiments, the sexual intercourse filter is configured to be fired at least when the second plurality of survey results indicates that the subject has developed symptoms of heart problems during sexual intercourse since receiving their last provision of the $PDE_5$ inhibitor pharmaceutical composition. When the sexual intercourse filter is fired, the subject is not permitted to obtain the $PDE_5$ inhibitor pharmaceutical composition over-the-counter (e.g., the method is terminated without authorizing re-provision of the $PDE_5$ inhibitor pharmaceutical composition to the subject). In some embodiments, the second plurality of survey results indicates that the subject has developed symptoms of heart problems during intercourse when the second plurality of survey results indicate that the subject has been diagnosed symptoms of heart problems during intercourse since receiving their last provision of the $PDE_5$ inhibitor pharmaceutical composition. In some embodiments, the second plurality of survey results indicates that the subject has developed symptoms of heart problems during sexual intercourse when the second plurality of survey results indicate that the subject has been diagnosed with symptoms of heart problems during sexual intercourse since receiving their last provision of the $PDE_5$ inhibitor composition. In some embodiments, the second plurality of survey results indicates that the subject has developed symptoms of heart problems during sexual intercourse when the second plurality of survey results indicate that the subject has experienced a symptom (e.g., a new and/or worsening symptom) of heart problems since receiving their last provision of the $PDE_5$ inhibitor composition, e.g., angina pectoris, AV block, migraines, syncope, tachycardia, palpitations, hypotension, postural hypotension, myocardial ischemia, cerebral thrombosis, cardiac arrest, heart failure, abnormal electrocardiogram, and/or cardiomyopathy.

Referring to block 498, in some embodiments the third plurality of filters includes a priapism filter (e.g., as described above in relation to the first survey). In some embodiments, the priapism filter is configured to be fired at least when the second plurality of survey results indicates that the subject has had priapism since receiving their last provision of the $PDE_5$ inhibitor pharmaceutical composition. When the priapism filter is fired, the subject is not permitted to obtain the $PDE_5$ inhibitor pharmaceutical composition over-the-counter (e.g., the method is terminated without authorizing re-provision of the $PDE_5$ inhibitor pharmaceutical composition to the subject). In some embodiments, the second plurality of survey results indicates that the subject has had priapism when the survey results indicate that the subject had priapism since receiving their last provision of the PDE5 inhibitor pharmaceutical composition. In some embodiments, the second plurality of survey results indicates that the subject has experienced priapism when the second plurality of survey results indicate that the subject has been diagnosed with priapism since receiving their last provision of the PDE5 inhibitor composition. In some embodiments, the second plurality of survey results indicates that the subject has experienced priapism when the second plurality of survey results indicate that the subject has experienced a symptom (e.g., a new and/or worsening symptom) of priapism since receiving their last provision of the PDE5 inhibitor composition, e.g., an erection lasting four hours or greater.

Referring to block 500, in some embodiments the third plurality of filters includes a sensory deterioration filter. In some embodiments, the sensory deterioration filter is configured to be fired at least when the second plurality of survey results indicates that the subject has developed sudden vision loss and/or a sudden hearing loss since receiving their last provision of the $PDE_5$ inhibitor pharmaceutical composition. In some embodiments, the second plurality of survey results indicates that the subject has developed sensory deterioration when the second plurality of survey results indicate that the subject has been diagnosed with sensory deterioration since receiving their last provision of the $PDE_5$ inhibitor pharmaceutical composition. In some embodiments, the second plurality of survey results indicates that the subject has developed sensory deterioration when the second plurality of survey results indicate that the subject has experienced (e.g., a new and/or worsening symptom) sensory deterioration since receiving their last provision of the $PDE_5$ inhibitor pharmaceutical composition the sensory deterioration filter is configured to be fired at least when the second plurality of survey results indicates that the subject has developed tinnitus, vertigo, and/or dizziness. When the sensory deterioration filter is fired, the subject is not permitted to obtain the $PDE_5$ inhibitor pharmaceutical composition over-the-counter (e.g., the method is terminated without authorizing re-provision of the $PDE_5$ inhibitor pharmaceutical composition to the subject).

In some embodiments, the device accounts for gaps in the subject's use of the $PDE_5$ inhibitor pharmaceutical composition when determining whether the subject's erectile dysfunction is being effectively managed by administration of the composition (e.g., in some embodiments, where the device determines that the user has been without a provision of the $PDE_5$ pharmaceutical composition for a threshold period of time, the device bypasses the blood pressure filter, or relaxes the requirements of the filter, for example, to a blood pressure level below that of the standard blood pressure levels required to trigger the blood pressure filter).

Figure 4H:
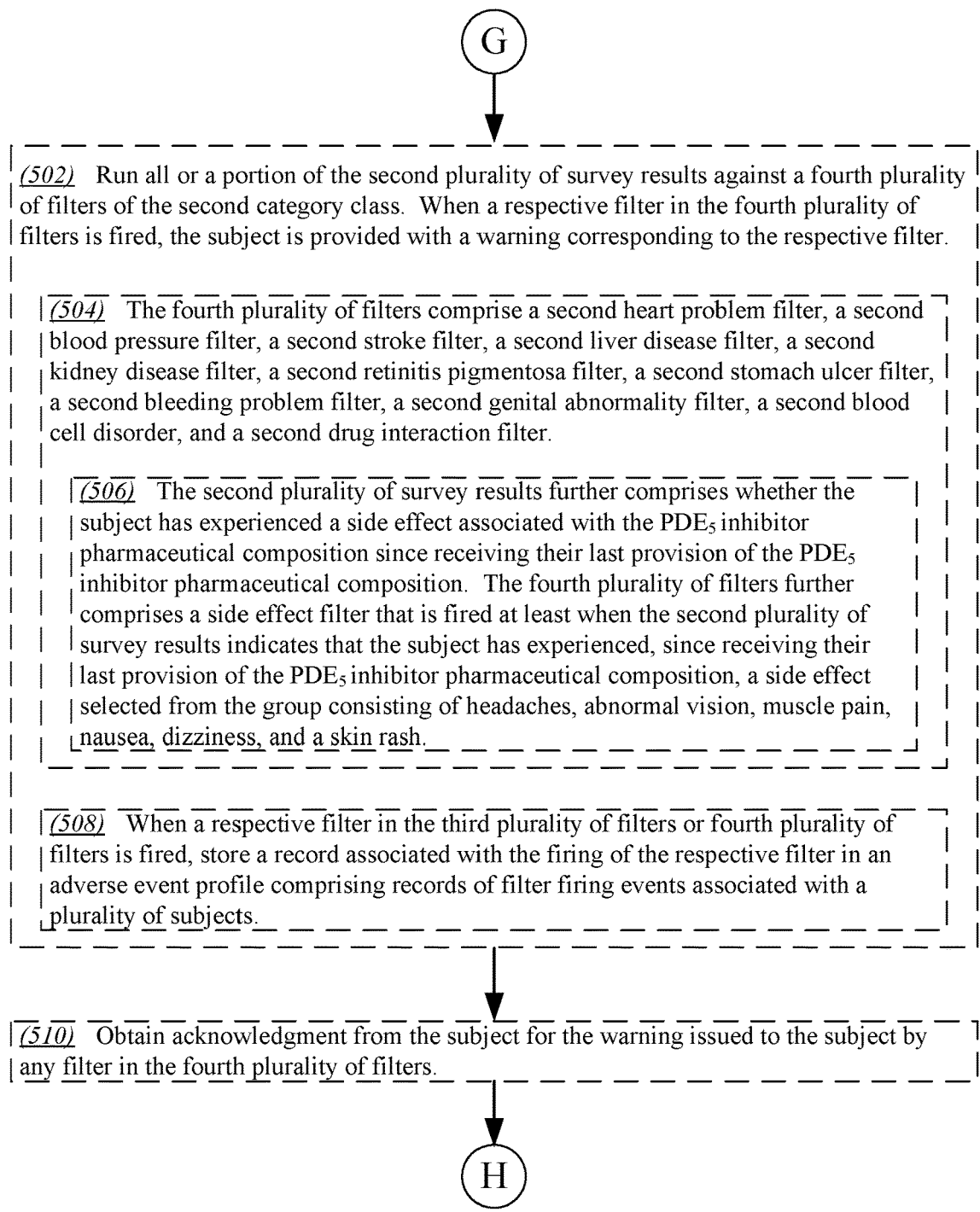
Figure 8A:
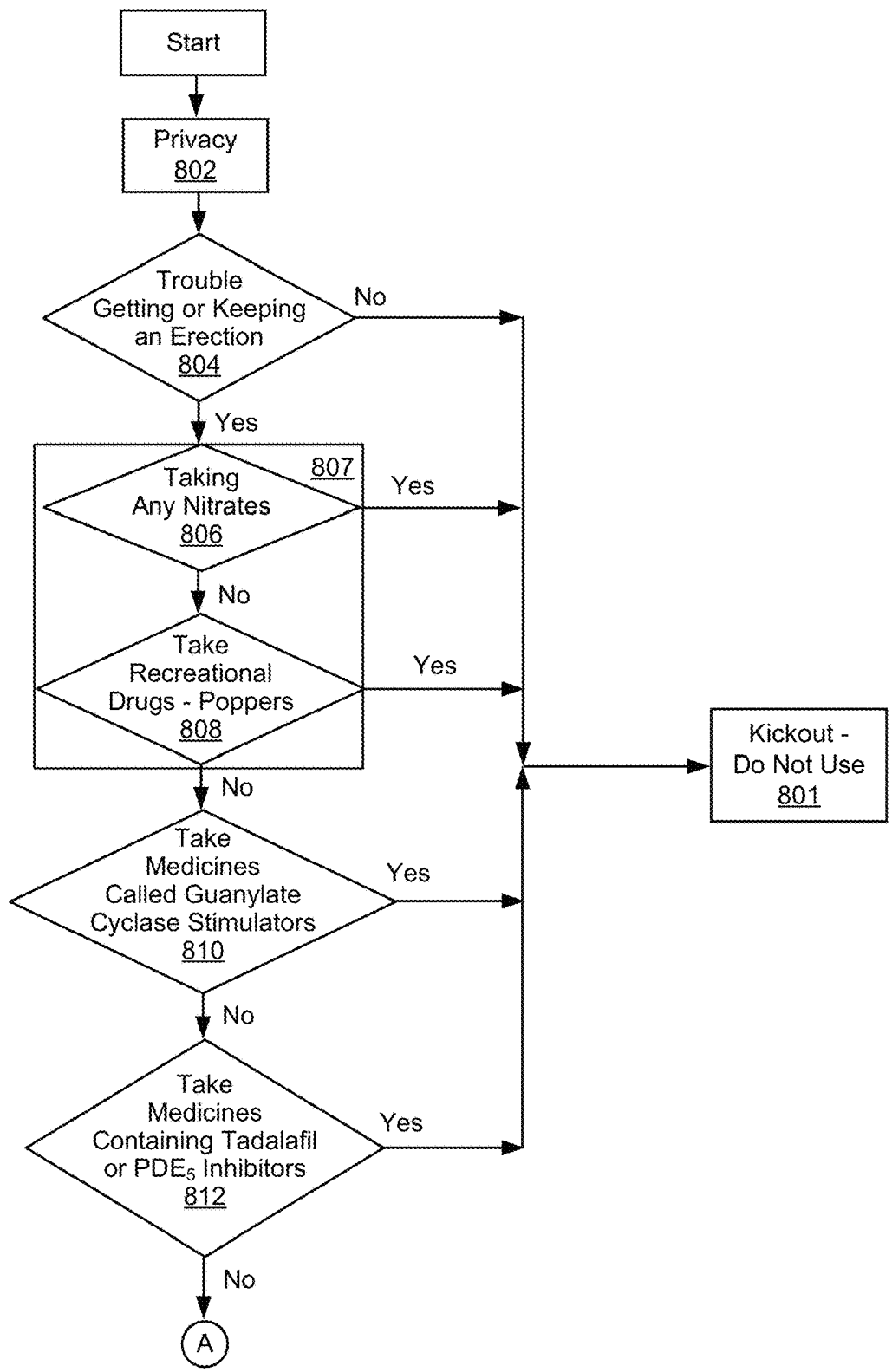
FIGS. 8A, 8B, 8C, 8D, and 8E collectively illustrate an example method for qualifying a subject for a refill of an over-the-counter provision PDE$_5$ inhibitor pharmaceutical composition in accordance with an embodiment of the present disclosure.
Figure 8B:
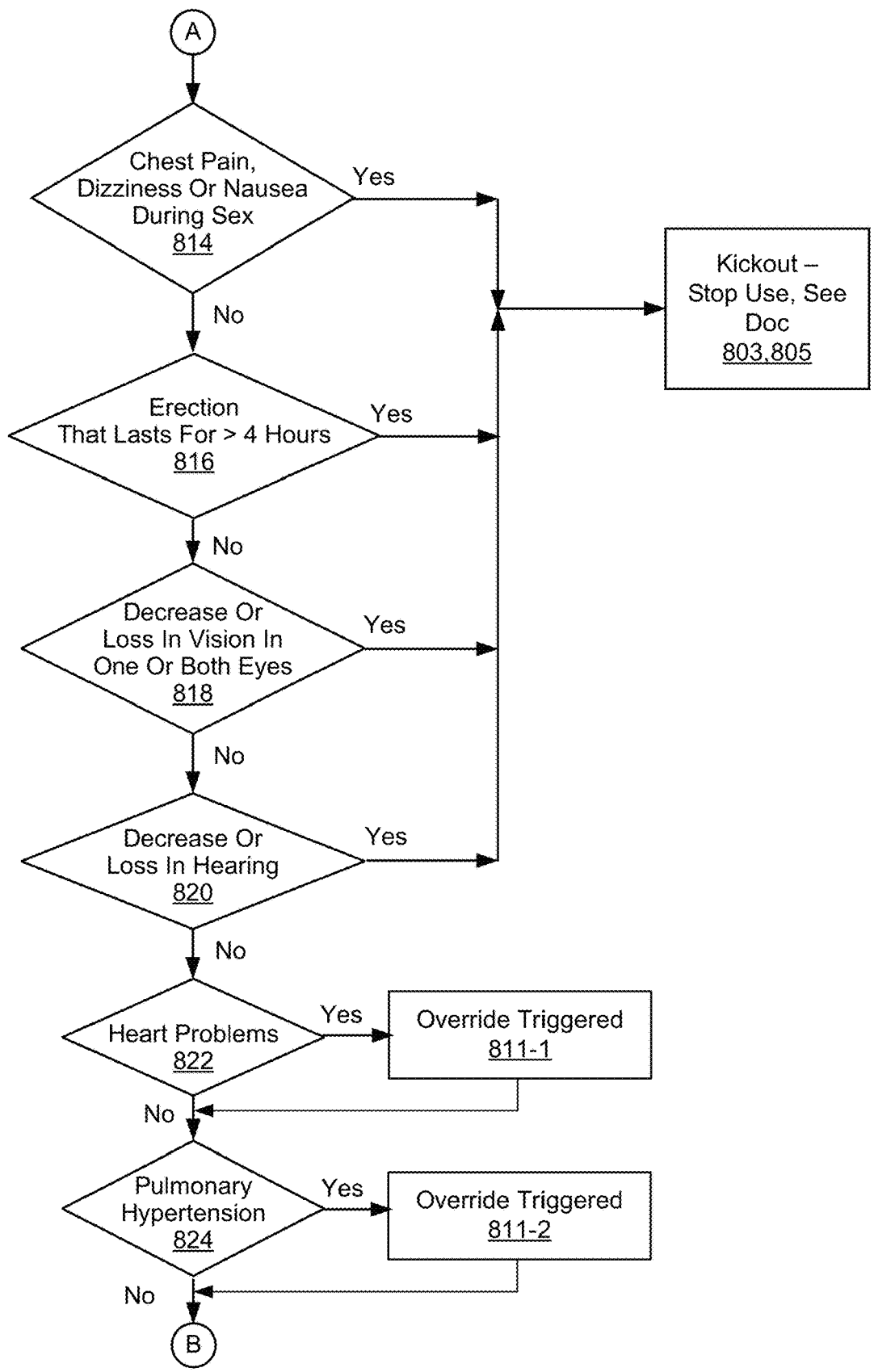
Figure 8C:
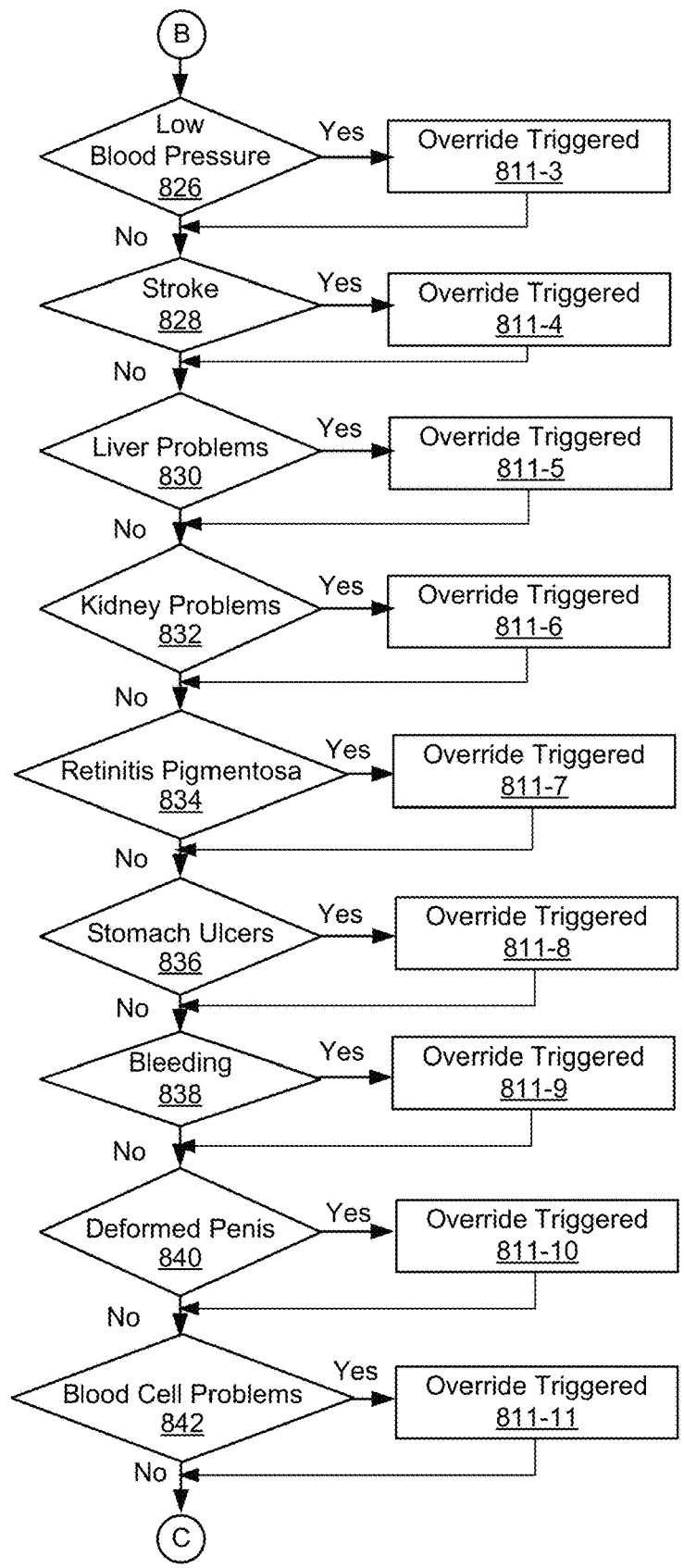
Figure 8D:
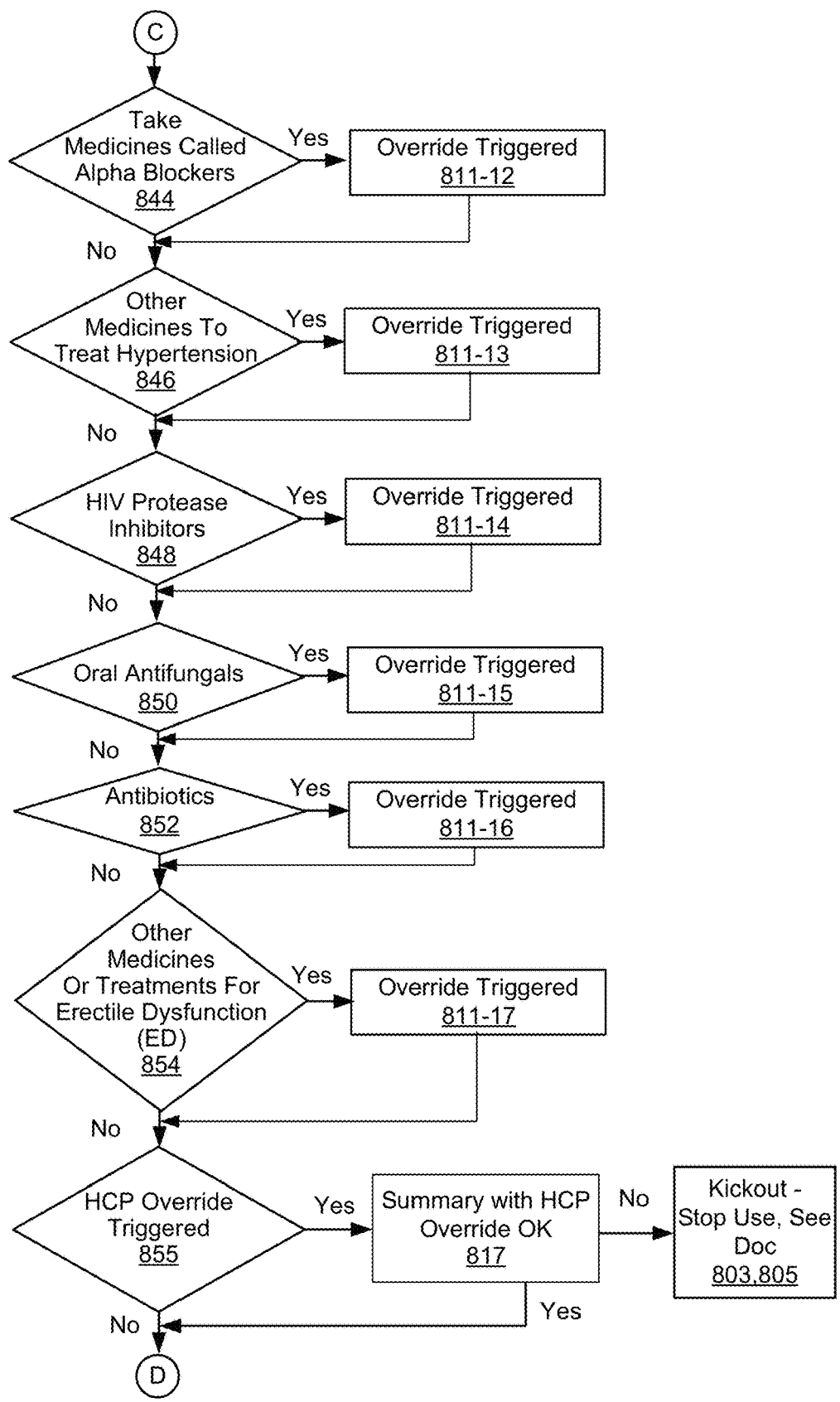
Figure 8E:
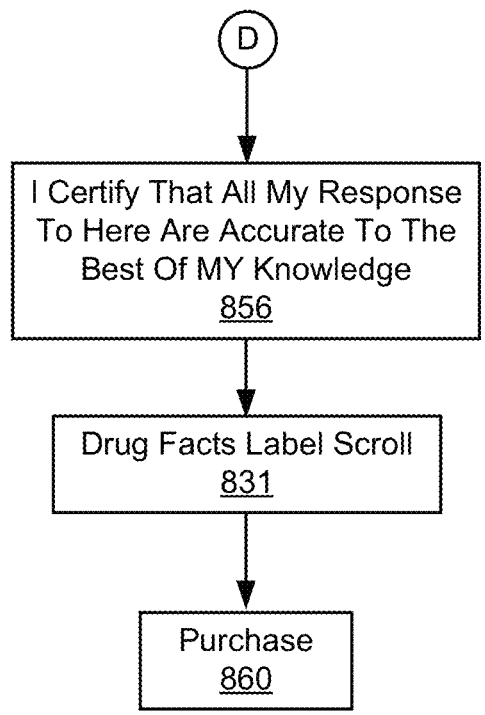

Referring to block 502 of FIG. 4H, the method also includes running all or a portion of the second survey results against a fourth plurality of filters of the second category class 220-2. When a respective filter in the fourth plurality of filters is fired, the subject is provided with a warning corresponding to the respective filter. In some embodiments, the warning is provided as a next step, e.g., prior to applying survey results to any subsequent filters, after the corresponding filter is fired. For example, with respect to FIG. 8A, in some embodiments, e.g., when the erectile dysfunction filter is triggered at 804, the device would provide the subject with a warning prior to proceeding to the vasodilator filter at 804, e.g., requiring the subject confirm they have discussed their erectile dysfunction with a health care provider and the healthcare provider still recommends taking a $PDE_5$ inhibitor pharmaceutical composition. In some embodiments the warning is provided after applying survey results to all subsequent filters. For example, with respect to FIGS. 8A and 8E, in some embodiments, e.g., when the erectile dysfunction filter is triggered at 804, the device would proceed to the vasodilator filter at 806 prior to transmitting a warning to the subject, and then transmit all warnings corresponding to filters of the second category class, at 856, after survey results have been applied to all subsequent filters.

In some embodiments, the fourth plurality of filters of the second category class 220-2 includes some or all of the filters listed in Table 6. For example, in some embodiments, the fourth plurality of filters includes 2, 3, 4, 5, 6, 7, 8, 9, 10, 11 or all 12 of the filters listed in Table 6. In some embodiments, the fourth plurality of filters of the second category class includes at least filters 1-11 as listed in Table 6.

TABLE 6

Example filters for risk factors associated with re-qualifying a subject for an over-the-counter provision of a PDE5 inhibitor pharmaceutical composition

| Filter | Exemplary Criteria |
| --- | --- |
| 1a | a heart problem filter |
| 2a | a blood pressure filter |
| 3a | a stroke filter |
| 4a | a liver disease filter |
| 5a | a kidney disease filter |
| 6a | a retinitis pigmentosa filter |
| 7a | a stomach ulcer filter |
| 8a | a bleeding problem filter |
| 9a | a genital abnormality filter |
| 10a | a blood cell disorder filter |
| 11a | a drug interaction filter |
| 12a | a side effects filter |

It is contemplated that, in some embodiments, any one or more of the filters provided in Table 6 will not be included in the fourth plurality of filters. For example, in some embodiments, a characteristic associated with a particular survey result will be informative when qualifying a subject for one particular $PDE_5$ inhibitor pharmaceutical composition but not for another $PDE_5$ inhibitor pharmaceutical composition. Accordingly, it is contemplated that the fourth plurality of filters includes any sub-set of filters provided in Table 6. Likewise, the skilled artisan may know of other filters, not provided in Table 6, that may be combined with any subset of the filters 222 provided in Table 6 to form the fourth plurality of filters results used in the methods described herein.

Referring to block 504, in some embodiments, the fourth plurality of filters includes a heart problem filter (e.g., heart problem filter 222-14 in FIG. 3 and/or filter 1a in Table 6). The heart problem filter is configured to be fired at least when the second plurality of survey results indicate that the subject has developed a heart problem since receiving their last provision of the $PDE_5$ inhibitor pharmaceutical composition. In some embodiments, the second plurality of survey results indicates that the subject has developed a heart problem when the second plurality of survey results indicate that the subject has been diagnosed with a heart problem since receiving their last provision of the $PDE_5$ inhibitor pharmaceutical composition. In some embodiments, the second plurality of survey results indicates that the subject has developed a heart problem when the second plurality of survey results indicate that the subject has experienced a symptom (e.g., a new and/or worsening symptom) of a heart problem since receiving their last provision of the $PDE_5$ inhibitor pharmaceutical composition, e.g., a heart attack, a heart failure, irregular heartbeats, arrhythmia, angina, chest pain, and/or narrowing of the aortic valve (block 436). When the heart problem filter is fired, the device transmits a warning corresponding to the heart problem filter, and requires the user to acknowledge the warning before authorizing a provision of the $PDE_5$ inhibitor pharmaceutical composition.

Referring to block 504, in some embodiments, the fourth plurality of filters includes a blood pressure filter (e.g., blood pressure filter 222-15 in FIG. 3 and/or filter 2a in Table 3). The blood pressure filter is configured to be fired at least when the second plurality of survey results indicates that the subject has either low blood pressure or uncontrolled high blood pressure. In some embodiments, the blood pressure filter is configured to be fired at least when the second plurality of survey results indicates that the subject has pulmonary hypertension. In some embodiments, the blood pressure filter comprises a first filter that is configured to be fired when the second plurality of survey results indicates that the subject has either low blood pressure or uncontrolled high blood pressure and a second filter that is configured to be fired when the second plurality of survey results indicates that the subject has pulmonary hypertension. In some embodiments, a blood pressure cutoffs defining when the blood pressure filter is fired and when the blood pressure filter is not fired are set according to a set of healthcare guidelines, which may change over time, and/or vary on a jurisdiction-by-jurisdiction basis. For example, in the United States, the American College of Cardiology and the American Heart Association collaborated to provide guidance on management of high blood pressure. Whelton P K, et al., J Am Coll Cardiol., S0735-1097(17)41519-1 (2017), the contents of which are hereby expressly incorporated by reference. These guidelines change over time as medical research and advances in treatment better inform management of high and low blood pressure. When the blood pressure filter is fired, the device transmits a warning corresponding to the blood pressure filter, and requires the user to acknowledge the warning before authorizing a provision of the $PDE_5$ inhibitor pharmaceutical composition. In some embodiments, the second plurality of survey results indicates that the subject has pulmonary hypertension when the second plurality of survey results indicate that the subject had pulmonary hypertension since receiving their last provision of the $PDE_5$ inhibitor pharmaceutical composition. In some embodiments, the second plurality of survey results indicates that the subject has developed pulmonary hypertension when the second plurality of survey results indicate that the subject has been diagnosed with pulmonary hypertension since receiving their last provision of the $PDE_5$ inhibitor composition. In some embodiments, the second plurality of survey results indicates that the subject has developed pulmonary hypertension when the second plurality of survey results indicate that the subject has experienced a symptom (e.g., a new and/or worsening symptom) of pulmonary hypertension since receiving their last provision of the $PDE_5$ inhibitor composition.

Referring to block 504, in some embodiments, the fourth plurality of filters includes a stroke filter (e.g., stroke filter 222-16 in FIG. 3 and/or filter 3a in Table 3). The stroke filter is configured to be fired at least when the second plurality of survey results indicates that the subject has had a stroke. When the stroke filter is fired, the device transmits a warning corresponding to the stroke filter, and requires the user to acknowledge the warning before authorizing a provision of the $PDE_5$ inhibitor pharmaceutical composition. In some embodiments, the second plurality of survey results indicates that the subject has had a stroke when the second plurality of survey results indicate that the subject had a stroke since receiving their last provision of the $PDE_5$ inhibitor pharmaceutical composition.

Referring to block 504, in some embodiments, the fourth plurality of filters includes a liver disease filter. The liver disease filter is configured to be fired at least when the second plurality of survey results indicates that the subject has developed a liver disease or a liver problem since receiving their last provision of the $PDE_5$ inhibitor pharmaceutical composition. In some embodiments, the second plurality of survey results indicates that the subject has developed a liver disease or a liver problem when the second plurality of survey results indicate that the subject has been diagnosed with a liver disease or a liver problem since receiving their last provision of the PDE5 inhibitor pharmaceutical composition. In some embodiments, the second plurality of survey results indicates that the subject has developed a liver disease or a liver problem when the second plurality of survey results indicate that the subject has experienced a symptom (e.g., a new and/or worsening symptom) of a liver disease or a liver problem since receiving their last provision of the PDE5 inhibitor pharmaceutical composition, e.g., impaired hepatic function, acute liver failure, and cholestasis. In some embodiments, the liver disease filter is fired at least when the second plurality of survey results indicates that the subject has had a reduction in liver function since receiving their last provision of the PDE5 inhibitor pharmaceutical composition. When the liver disease filter is fired, the device transmits a warning corresponding to the liver disease filter, and requires the user to acknowledge the warning before authorizing a provision of the $PDE_5$ inhibitor pharmaceutical composition.

Referring to block 504, in some embodiments, the fourth plurality of filters includes a kidney disease filter. The kidney disease filter is configured to be fired at least when the second plurality of survey results indicates that the subject has developed a kidney problem since receiving their last provision of the $PDE_5$ inhibitor pharmaceutical composition. When the kidney disease filter is fired, the device transmits a warning corresponding to the kidney disease filter, and requires the user to acknowledge the warning before authorizing a provision of the $PDE_5$ inhibitor pharmaceutical composition. In some embodiments, the second plurality of survey results indicates that the subject has developed a kidney problem when the second plurality of survey results indicate that the subject has developed a kidney problem since receiving their last provision of the $PDE_5$ inhibitor pharmaceutical composition. In some embodiments, the second plurality of survey results indicates that the subject has developed a kidney problem when the second plurality of survey results indicate that the subject has been diagnosed with a kidney problem since receiving their last provision of the $PDE_5$ inhibitor composition. In some embodiments, the second plurality of survey results indicates that the subject has developed a kidney problem when the second plurality of survey results indicate that the subject has experienced a symptom (e.g., a new and/or worsening symptom) of a kidney problem since receiving their last provision of the $PDE_5$ inhibitor composition e.g., fatigue, high blood pressure, loss of appetite, malaise, and/or water-electrolyte imbalance.

Referring to block 504, in some embodiments, the fourth plurality of filters includes a retinitis pigmentosa filter. The retinitis pigmentosa filter is configured to be fired at least when the second plurality of survey results indicates that the subject has been diagnosed with retinitis pigmentosa since receiving their last provision of the $PDE_5$ inhibitor pharmaceutical composition. When the retinitis pigmentosa filter is fired, the device transmits a warning corresponding to the retinitis pigmentosa filter, and requires the user to acknowledge the warning before authorizing a provision of the $PDE_5$ inhibitor pharmaceutical composition. In some embodiments, the second plurality of survey results indicates that the subject has been diagnosed with retinitis pigmentosa when the second plurality of survey results indicate that the subject was diagnosed with retinitis pigmentosa receiving their last provision of the $PDE_5$ inhibitor pharmaceutical composition.

Referring to block 504, in some embodiments, the fourth plurality of filters includes a stomach ulcer filter. The stomach ulcer filter is configured to be fired at least when the second plurality of survey results indicates that the subject has developed a stomach ulcer since receiving their last provision of the $PDE_5$ inhibitor pharmaceutical composition. When the stomach ulcer filter is fired, the device transmits a warning corresponding to the stomach ulcer filter, and requires the user to acknowledge the warning before authorizing a provision of the $PDE_5$ inhibitor pharmaceutical composition. In some embodiments, the second plurality of survey results indicates that the subject has developed a stomach ulcer when the second plurality of survey results indicate that the subject was diagnosed with a stomach ulcer receiving their last provision of the $PDE_5$ inhibitor pharmaceutical composition.

Referring to block 504, in some embodiments, the fourth plurality of filters includes a bleeding problem filter. The bleeding problem filter is configured to be fired at least when the second plurality of survey results indicates that the subject has developed a bleeding disorder since receiving their last provision of the $PDE_5$ inhibitor pharmaceutical composition. In some embodiments, bleeding disorders indicate significant active peptic ulceration. When the bleeding problem filter is fired, the device transmits a warning corresponding to the bleeding problem filter, and requires the user to acknowledge the warning before authorizing a provision of the $PDE_5$ inhibitor pharmaceutical composition. In some embodiments, the second plurality of survey results indicates that the subject has developed a bleeding disorder when the second plurality of survey results indicate that the subject was diagnosed with a bleeding disorder since receiving their last provision of the $PDE_5$ inhibitor pharmaceutical composition. In some embodiments, the second plurality of survey results indicates that the subject has developed a bleeding problem when the second plurality of survey results indicate that the subject has been diagnosed with a bleeding problem since receiving their last provision of the PDE$_5$ inhibitor composition. In some embodiments, the second plurality of survey results indicates that the subject has developed a bleeding problem when the second plurality of survey results indicate that the subject has experienced a symptom (e.g., a new and/or worsening symptom) of a bleeding problem since receiving their last provision of the PDE$_5$ inhibitor composition e.g., a coagulation problem.

Referring to block 504, in some embodiments, the fourth plurality of filters includes a genital abnormality filter. The genital abnormality filter is configured to be fired at least when the second plurality of survey results indicates that the subject has developed an abnormal penile shape since receiving their last provision of the PDE$_5$ inhibitor pharmaceutical composition. In some embodiments, a condition which is capable of firing the genital abnormality filter includes angulation, cavernosal fibrosis, or Peyronie's disease. When the genital abnormality filter is fired, the device transmits a warning corresponding to the genital abnormality filter, and requires the user to acknowledge the warning before authorizing a provision of the PDE$_5$ inhibitor pharmaceutical composition. In some embodiments, the second plurality of survey results indicates that the subject has developed an abnormal penile shape when the second plurality of survey results indicate that the subject has developed an abnormal penile shape since receiving their last provision of the PDE$_5$ inhibitor pharmaceutical composition.

Referring to block 504, in some embodiments, the fourth plurality of filters includes a blood cell disorder filter. The blood cell disorder filter is configured to be fired at least when the second plurality of survey results indicates that the subject has developed a blood disorder since receiving their last provision of the PDE$_5$ inhibitor pharmaceutical composition. In some embodiments, blood cell disorders include sickle cell anemia, multiple myeloma, and leukemia. When the blood cell disorder filter is fired, the device transmits a warning corresponding to the blood cell disorder filter, and requires the user to acknowledge the warning before authorizing a provision of the PDE$_5$ inhibitor pharmaceutical composition. In some embodiments, the second plurality of survey results indicates that the subject has developed a blood disorder when the second plurality of survey results indicate that the subject has developed a blood disorder since receiving their last provision of the PDE$_5$ inhibitor pharmaceutical composition. In some embodiments, the second plurality of survey results indicates that the subject has developed a blood cell disorder when the second plurality of survey results indicate that the subject has been diagnosed with a blood cell disorder since receiving their last provision of the PDE$_5$ inhibitor composition. In some embodiments, the second plurality of survey results indicates that the subject has developed a blood cell disorder when the second plurality of survey results indicate that the subject has experienced a symptom (e.g., a new and/or worsening symptom) of a blood cell disorder since receiving their last provision of the PDE$_5$ inhibitor composition.

Referring to block 504, in some embodiments, the fourth plurality of filters includes a drug interaction filter. The drug interaction filter is configured to be fired at least when the second plurality of survey results indicates that the subject indicates that the subject has started taking a medication that interacts (e.g., a pharmacokinetic interaction and/or a pharmacodynamic interaction) with the PDE$_5$ inhibitor pharmaceutical composition. In some embodiments, the drug interaction filter is fired when the second plurality of survey results indicates that the subject has started taking a medication selected from the group consisting of an alpha blocker (e.g., terazosin, tamsulosin, doxazosin mesylate, prazosin HCl, alfuzosin, dutasteride and tamsulosin HCl, and silodosin), an HIV protease inhibitor (e.g., ritonavir), an antifungal medication (e.g., ketoconazole and itraconazole), an antibiotic (e.g., clarithromycin, telithromycin, and erythromycin), a blood pressure medication (e.g., a medication to treat hypertension), and an erectile dysfunction medication (block 462). When the drug interaction filter is fired, the device transmits a warning corresponding to the drug interaction filter, and requires the user to acknowledge the warning before authorizing a provision of the PDE$_5$ inhibitor pharmaceutical composition. As previously described, these interactions can be pharmacodynamic drug-drug interactions or pharmacokinetic drug-drug interactions. In some embodiments, the interactions (e.g., triggering conditions 224) that are capable of firing the second drug interaction filter are the same as the interactions that are capable of firing the first drug interaction filter assuming that the PDE$_5$ inhibitor pharmaceutical composition is the same between the fulfillment process and the re-fulfillment process. In some embodiments, the second plurality of survey results indicates that the subject has started taking a medication that interacts with the PDE$_5$ inhibitor pharmaceutical composition when the second plurality of survey results indicate that the subject is taking a medication that interacts with the PDE$_5$ inhibitor since receiving their last provision of the PDE$_5$ inhibitor pharmaceutical composition.

Referring to block 506, in some embodiments the second survey results further includes whether the subject has developed side effects associated with the PDE$_5$ inhibitor pharmaceutical composition since receiving their last provision of the PDE$_5$ inhibitor pharmaceutical composition. Accordingly, in some embodiments, the fourth plurality of filters further comprises a side effect filter that is configured to be fired at least when the second survey results indicate that the subject has developed side effects since receiving their last provision of the PDE$_5$ inhibitor pharmaceutical composition. Side effects that are capable of triggering (e.g., triggering condition) the side effect filter indicate headaches, abnormal vision, muscle pain, nausea, dizziness, and a skin rash. In some embodiments, side effects that are capable of triggering the side effect filter include a stuffy nose, a runny nose, back pain, and/or indigestion. When the side effect filter is fired, the device transmits a warning corresponding to the medical issue filter, and requires the user to acknowledge the warning before authorizing a provision of the metformin pharmaceutical composition.

Referring to block 508, in some embodiments when a respective filter in the third plurality of filters or fourth plurality of filters is fired, a record associated with the firing of the respective filter is stored (e.g., memorializing an adverse event that is required to be reported to a regulatory agency). This record is stored in an adverse event module 242 which comprises records of filter firing events associated with a plurality of subjects (e.g., an aggregation of adverse events associated with the PDE$_5$ inhibitor pharmaceutical composition across a population of subjects taking the PDE$_5$ inhibitor pharmaceutical composition over-the-counter). In some embodiments, an indication the adverse event is communicated to a third party (e.g., a medical practitioner associated with the subject, a health care provider of the subject, a manufacturer/promoter of the PDE$_5$ inhibitor pharmaceutical composition, and/or a regulatory agency). In some embodiments, the indication is automatically stored in the adverse event module 242 when a response submitted by a subject as part of the second survey, triggers a filter associated with an adverse event.

Referring to block 510, in some embodiments the method also includes obtaining acknowledgment from the subject for each warning issued to the subject by any filter in the fourth plurality of filters. As described with respect to the warnings issued in conjunction with the second plurality of filters of the second category class, in some embodiments, the warning includes a prompt for the subject to indicate whether they have discussed the risk factor underlying the respective filter in the second plurality of filters that was fired with a health care practitioner (e.g., a licensed medical practitioner), e.g., and the health care practitioner indicated that the subject should take a $PDE_5$ inhibitor pharmaceutical composition in view of the underlying risk factor. Accordingly, acknowledgement is obtained from the subject when the subject indicates that they have discussed the risk factor underlying the respective filter in the fourth plurality of filters that was fired with a health care provider.

Referring to block 512 of FIG. 4I, in some embodiments the procedure further includes proceeding with the re-fulfillment process when the re-fulfillment process is not already terminated by the firing of a filter in the third plurality of filters (e.g., the second erectile dysfunction filter). In order for completion of the re-fulfillment process, the subject is required to acknowledge each warning associated with each filter 22 in the fourth plurality of filters that was fired.

Referring to block 514, in some embodiments the re-fulfillment process also includes storing a record in the user profile 234 of the subject of a re-order 238 for the $PDE_5$ inhibitor pharmaceutical composition.

The re-fulfillment process also includes communicating an over-the-counter drug facts label 230 for the $PDE_5$ inhibitor pharmaceutical composition to the subject. As previously described, communication of the over-the-counter drug facts label 230 can occur in a variety of means. Upon confirmation from the subject that the over-the-counter drug facts label 230 has been received and read, the method includes authorizing a re-order provision of the $PDE_5$ inhibitor pharmaceutical composition to the subject. In some embodiments, this re-order provision includes the destination of the subject.

FIG. 7 illustrates an example method (700) (e.g., performed at an electric device) for qualifying a subject for an over-the-counter $PDE_5$ inhibitor pharmaceutical composition. In some embodiments, the method of FIG. 7 is utilized when the subject has not been previously qualified for the $PDE_5$ inhibitor pharmaceutical composition. In some embodiments, the method of FIG. 7 is utilized when the subject was previously qualified for the $PDE_5$ inhibitor composition but a predetermined period of time elapsed since the previous qualification/re-qualification occurred (e.g., the most recent qualification of the subject was greater than one year ago).

Referring to FIG. 7, the device prompts (702) the subject to acknowledge a privacy notice. Since the present disclosure requires the subject to know and input sensitive medical information (e.g., information only the subject and a medical practitioner have access to), privacy of this information is important. Once the subject has acknowledged they have the requisite privacy for continuing, the device proceeds with the qualification process.

The device prompts the subject to provide information about their gender and then applies (704) the answer received from the subject to a gender filter. When the gender filter is fired (e.g., when the answer indicates the subject is not male), the device terminates (701) the qualification process without authorizing provision of the $PDE_5$ inhibitor pharmaceutical agent and, optionally, transmits advice to the user as to why they should not take the $PDE_5$ inhibitor pharmaceutical agent.

When the gender filter is not fired, the device proceeds with the qualification process, prompting the subject to provide information indicating their age and then applies (706) the answer received from the subject to an age filter. When the age filter is fired (e.g., when the answer indicates the subject is younger than eighteen years old), the device terminates (701) the qualification process without authorizing provision of the $PDE_5$ inhibitor pharmaceutical agent and, optionally, transmits advice to the user as to why they should not take the $PDE_5$ inhibitor pharmaceutical agent and/or to return once they have obtained an age at which it would be appropriate to take a $PDE_5$ inhibitor pharmaceutical agent.

When the age filter is not fired, the device proceeds with the qualification process, prompting to provide information indicating whether the subject has erectile dysfunction and then applies (708) the answer received from the subject to an erectile dysfunction filter. When the erectile dysfunction filter is fired (e.g., when the answer indicates the subject does not have erectile dysfunction), the device terminates (701) the qualification process without authorizing provision of the $PDE_5$ inhibitor pharmaceutical agent and, optionally, transmits advice to the user as to why they should not take the $PDE_5$ inhibitor pharmaceutical agent.

When the erectile dysfunction filter is not fired, the device proceeds with the qualification process, prompting the subject to provide information indicating whether the subject is taking a nitrate or nitrite vasodilator composition and then applies (710) the answer received from the subject to a vasodilator filter. When the vasodilator filter is fired (e.g., when the answer indicates the subject is taking a nitrate or nitrite vasodilator), the device terminates (701) the qualification process without authorizing provision of the $PDE_5$ inhibitor pharmaceutical agent and, optionally, transmits advice to the user as to why they should not take the $PDE_5$ inhibitor pharmaceutical agent.

When the vasodilator filter is not fired, the device proceeds with the qualification process, prompting the subject to provide information indicating whether the subject is taking a guanylate cyclase stimulator medication and then applies (712) the answer received from the subject to a guanylate cyclase stimulator filter. When the guanylate cyclase stimulator filter is fired (e.g., when the answer indicates the subject is taking a guanylate cyclase stimulator composition), the device terminates (701) the qualification process without authorizing provision of the $PDE_5$ inhibitor pharmaceutical agent and, optionally, transmits advice to the user as to why they should not take the $PDE_5$ inhibitor pharmaceutical agent When the guanylate cyclase stimulator filter is not fired, the device proceeds with the qualification process, prompting the subject to provide information indicating whether the subject is taking a $PDE_5$ inhibitor composition and then applies (714) the answer received from the subject to a $PDE_5$ inhibitor filter. When the $PDE_5$ inhibitor filter is fired (e.g., when the answer indicates the subject is taking a $PDE_5$ inhibitor composition), the device terminates (701) the qualification process without authorizing provision of the $PDE_5$ inhibitor pharmaceutical agent and, optionally, transmits advice to the user as to why they should not take the $PDE_5$ inhibitor pharmaceutical agent.

When the PDE$_5$ inhibitor filter is not fired, the device proceeds with the qualification process, prompting the subject to provide information indicating whether the subject has ever had a heart problem and then applies (716) the answer received from the subject to a heart problem filter. When the heart problem filter is fired (e.g., when the answer indicates that the subject has been diagnosed with a heart problem) the device initiates (711-1) an override procedure (e.g., creates a record indicating that the user must confirm they have discussed taking a PDE$_5$ inhibitor pharmaceutical composition with a heath care provider). When the heart problem filter is not fired (e.g., when the answer indicates the subject has not had a heart problem), the device proceeds with the qualification process, prompting the subject to provide information indicating a pulmonary hypertension status and then applies (718) the answer received from the subject to a pulmonary hypertension filter. When the pulmonary hypertension filter is fired (e.g., when the answer indicates that the subject has been diagnosed with pulmonary hypertension) the device initiates (711-2) an override procedure (e.g., creates a record indicating that the user must confirm they have discussed taking a PDE$_5$ inhibitor pharmaceutical composition with a heath care provider). When the pulmonary hypertension filter is not fired, the device proceeds with the qualification process, prompting the subject to provide information indicating a blood pressure status and then applies (720) the answer received from the subject to a blood pressure filter. As previously described, in some embodiments, the pulmonary hypertension filter and the blood pressure filter are combined as a single filter. When the blood pressure filter is fired (e.g., when the answer indicates that the subject has high blood pressure) the device initiates (711-3) an override procedure (e.g., creates a record indicating that the user must confirm they have discussed taking a PDE$_5$ inhibitor pharmaceutical composition with a heath care provider). When the blood pressure problem filter is not fired (e.g., when the answer indicates the subject has normal blood pressure or controlled high blood pressure), the device proceeds with the qualification process, prompting the subject to provide information indicating whether the subject has ever had a stroke and then applies (722) the answer received from the subject to a stroke filter. When the stroke filter is fired (e.g., when the answer indicates that the subject has had a stroke) the device initiates (711-4) an override procedure (e.g., creates a record indicating that the user must confirm they have discussed taking a PDE$_5$ inhibitor pharmaceutical composition with a heath care provider). When the stroke filter is not fired (e.g., when the answer indicates the subject has not had a stroke), the device proceeds with the qualification process, prompting the subject to provide information indicating whether the subject has a liver problem and then applies (724) the answer received from the subject to a liver disease filter. When the liver disease filter is fired (e.g., when the answer indicates that the subject has been diagnosed with a liver problem) the device initiates (711-1) an override procedure (e.g., creates a record indicating that the user must confirm they have discussed taking a PDE$_5$ inhibitor pharmaceutical composition with a heath care provider). When the liver disease filter is not fired (e.g., when the answer indicates the subject does not have a liver problem), the device proceeds with the qualification process, prompting the subject to provide information indicating a kidney function status of the subject and then applies (726) the answer received from the subject to a kidney disease filter. When the kidney disease filter is fired (e.g., when the answer indicates that the subject has been diagnosed with a kidney problem) the device initiates (711-6) an override procedure (e.g., creates a record indicating that the user must confirm they have discussed taking a PDE$_5$ inhibitor pharmaceutical composition with a heath care provider). When the kidney disease filter is not fired (e.g., when the answer indicates the subject does not have a kidney problem), the device proceeds with the qualification process, prompting the subject to provide information indicating whether the subject has retinitis pigmentosa and then applies (728) the answer received from the subject to a retinitis pigmentosa filter. When the retinitis pigmentosa filter is fired (e.g., when the answer indicates that the subject has been diagnosed with retinitis pigmentosa) the device initiates (711-7) an override procedure (e.g., creates a record indicating that the user must confirm they have discussed taking a PDE$_5$ inhibitor pharmaceutical composition with a heath care provider). When the retinitis pigmentosa filter is not fired (e.g., when the answer indicates the subject does not have retinitis pigmentosa), the device proceeds with the qualification process, prompting the subject to provide information indicating whether the subject has developed vision loss and then applies (730) the answer received from the subject to a vision deterioration filter. When the vision deterioration filter is fired (e.g., when the answer indicates that the subject has experienced vision loss) the device initiates (711-8) an override procedure (e.g., creates a record indicating that the user must confirm they have discussed taking a PDE$_5$ inhibitor pharmaceutical composition with a heath care provider). When the vision deterioration filter is not fired (e.g., when the answer indicates the subject has not developed vision deterioration), the device proceeds with the qualification process, prompting the subject to provide information indicating whether the subject has ever had a stomach ulcer and then applies (732) the answer received from the subject to a stomach ulcer filter. When the stomach ulcer filter is fired (e.g., when the answer indicates that the subject has developed a stomach ulcer) the device initiates (711-9) an override procedure (e.g., creates a record indicating that the user must confirm they have discussed taking a PDE$_5$ inhibitor pharmaceutical composition with a heath care provider). when the answer indicates the subject has not had a stomach ulcer), the device proceeds with the qualification process, prompting the subject to provide information indicating whether the subject has a bleeding disorder and then applies (734) the answer received from the subject to a bleeding disorder filter. When the bleeding disorder filter is fired (e.g., when the answer indicates that the subject has been diagnosed with a bleeding disorder) the device initiates (711-10) an override procedure (e.g., creates a record indicating that the user must confirm they have discussed taking a PDE$_5$ inhibitor pharmaceutical composition with a heath care provider). When the bleeding disorder filter is not fired (e.g., when the answer indicates the subject has not had a bleeding disorder), the device proceeds with the qualification process, prompting the subject to provide information indicating a genital status of the subject and then applies (736) the answer received from the subject to a genital abnormality filter. When the genital abnormality filter is fired (e.g., when the answer indicates that the subject has a deformed penis or Peyronie's disease) the device initiates (711-11) an override procedure (e.g., creates a record indicating that the user must confirm they have discussed taking a PDE$_5$ inhibitor pharmaceutical composition with a heath care provider). When the genital abnormality filter is not fired (e.g., when the answer indicates the subject has a normal penile shape), the device proceeds with the qualification process, prompting the subject to provide information indicating whether the subject has ever experienced priapism and then applies (738) the answer received from the subject to a priapism filter. When the priapism filter is fired (e.g., when the answer indicates that the subject has had an erection lasting longer than four hours) the device initiates (711-12) an override procedure (e.g., creates a record indicating that the user must confirm they have discussed taking a $PDE_5$ inhibitor pharmaceutical composition with a heath care provider). When the priapism filter is not fired (e.g., when the answer indicates the subject has not experienced priapism), the device proceeds with the qualification process, prompting the subject to provide information indicating whether the subject has a blood cell disorder and then applies (740) the answer received from the subject to a blood cell disorder filter. When the blood cell disorder filter is fired (e.g., when the answer indicates that the subject has been diagnosed with a blood cell disorder) the device initiates (711-13) an override procedure (e.g., creates a record indicating that the user must confirm they have discussed taking a $PDE_5$ inhibitor pharmaceutical composition with a heath care provider). When the blood cell disorder filter is not fired (e.g., when the answer indicates the subject does not have a blood cell disorder), the device proceeds with the qualification process.

The device then proceeds with the qualification process, prompting the subject to provide information indicating whether the subject is taking a medication that interacts with the $PDE_5$ inhibitor pharmaceutical composition and then applies (742-752) the answer received from the subject to a drug interaction filter. In some embodiments, the drug interaction filter comprises a plurality of filters, where each filter in the plurality of filters is configured for a specific drug interaction. For instance, in some embodiments the drug interaction filter comprises an alpha blocker filter, a hypertension medication filter, an HIV protease inhibitor filter, an oral antifungal filter, an antibiotics filter, and an erectile dysfunction medication filter. When the drug interaction filter is fired (e.g., when the answer indicates the subject is taking a medication that interacts with the $PDE_5$ inhibitor pharmaceutical composition), the device initiates (711-14-711-18) an override procedure (e.g., creates a record indicating that the user must confirm they have discussed taking a $PDE_5$ inhibitor pharmaceutical composition with a heath care provider).

The device proceeds with the qualification process, determining (753) whether the override procedure has been triggered (e.g., by firing of one or more of the heart problem filter, the pulmonary hypertension filter, the blood pressure filter, the stroke filter, the liver disease filter, the kidney problem filter, the retinitis pigmentosa filter, the sensory deterioration filter, the stomach ulcer filter, the bleeding problem filter, the genital abnormality filter, the priapism filter, or the blood cell disorder filter, the alpha blocker filter, the hypertension medication filter, the HIV protease inhibitor filter, the oral antifungal filter, the antibiotics filter, and/or the erectile dysfunction medication filter). If the override procedure has been triggered, the device prompts (717) the user to confirm that they have spoken with a medical professional about taking a $PDE_5$ inhibitor pharmaceutical composition (e.g., in view of the underlying risk factor that triggered the heart problem filter, the pulmonary hypertension filter, the blood pressure filter, the stroke filter, the liver disease filter, the kidney problem filter, the retinitis pigmentosa filter, the sensory deterioration filter, the stomach ulcer filter, the bleeding problem filter, the genital abnormality filter, the priapism filter, the blood cell disorder filter, the alpha blocker filter, the hypertension medication filter, the HIV protease inhibitor filter, the oral antifungal filter, the antibiotics filter, and/or the erectile dysfunction medication filter) and the medical professional recommended taking the $PDE_5$ inhibitor pharmaceutical composition. If the user's response indicates they have not spoken with a medical professional or the medical professional did not recommend taking the $PDE_5$ inhibitor pharmaceutical composition, the device terminates (703) the process and, optionally, transmits advice for the subject to consult a medical professional.

If the override procedure was not triggered, or the override procedure was triggered and the subject's response indicated that a medical professional recommended they take a $PDE_5$ inhibitor pharmaceutical composition (e.g., in view of the underlying risk factor triggering the override procedure), the device then proceeds with the qualification process, prompting (754) the subject to confirm their answers. If the user confirms their answers, the device transmits (831) a drug facts label for the $PDE_5$ inhibitor pharmaceutical composition and prompts the user to read the drug facts label. If the subject confirms they have read the drug facts label, the device proceeds to authorize (758) purchase of the $PDE_5$ inhibitor pharmaceutical composition.

FIG. 8 illustrates an example method for qualifying a subject for a refill of an over-the-counter $PDE_5$ inhibitor pharmaceutical composition (e.g., following a prescription from a medical professional or initial qualification by a method described herein). Referring to FIG. 8, the device prompts (802) the subject to acknowledge a privacy notice. Once the subject has acknowledged they have the requisite privacy for continuing, the device proceeds with the process, prompting the user to indicate their erectile dysfunction status and applies (804) the answer received from the subject to an erectile dysfunction filter. When the erectile dysfunction filter is fired (e.g., when the answer indicates the subject does not have erectile dysfunction), the device terminates (801) the qualification process, optionally transmitting advice to the user as to why they should not take the $PDE_5$ inhibitor pharmaceutical agent.

When the erectile dysfunction filter is not fired, the device proceeds with the qualification process, prompting the subject to provide information indicating whether the subject has started to take a nitrate or nitrite vasodilator composition since receiving their last provision of the $PDE_5$ inhibitor pharmaceutical composition and then applies (806) the answer received from the subject to a vasodilator filter. When the vasodilator filter is fired (e.g., when the answer indicates that the subject is taking a vasodilator composition including a nitrate or a nitrite), the device terminates (801) the qualification process without authorizing provision of the $PDE_5$ inhibitor pharmaceutical agent and, optionally, transmits advice to the user as to why they should not take the $PDE_5$ inhibitor pharmaceutical agent. When the vasodilator filter is not fired, the device proceeds with the qualification process, prompting the subject to provide information indicating whether the subject has started to take a recreational drug known as "popper(s)" and then applies (808) the answer received from the subject to the vasodilator filter. As previously described, in some embodiments the prompts and processes (806,808) associated with the vasodilator filter are combined into a single prompt and process (807).

When the vasodilator filter is not fired, the device proceeds with the qualification process, prompting the subject to provide information indicating whether the subject has started to take a guanylate cyclase stimulator medication since receiving their last provision of the $PDE_5$ inhibitor pharmaceutical composition and then applies (810) the answer received from the subject to a guanylate cyclase stimulator filter. When the guanylate cyclase stimulator filter is fired (e.g., when the answer indicates the subject is taking a guanylate cyclase stimulator composition), the device terminates (801) the qualification process without authorizing provision of the PDE$_5$ inhibitor pharmaceutical agent and, optionally, transmits advice to the user as to why they should not take the PDE$_5$ inhibitor pharmaceutical agent.

When the guanylate cyclase stimulator filter is not fired, the device proceeds with the qualification process, prompting the subject to provide information indicating whether the subject is taking a PDE$_5$ inhibitor composition and then applies (812) the answer received from the subject to a PDE$_5$ inhibitor filter. When the PDE$_5$ inhibitor filter is fired (e.g., when the answer indicates the subject is taking a PDE$_5$ inhibitor composition), the device terminates (801) the qualification process without authorizing provision of the PDE$_5$ inhibitor pharmaceutical agent and, optionally, transmits advice to the user as to why they should not take the PDE$_5$ inhibitor pharmaceutical agent.

When the PDE$_5$ inhibitor filter is not fired, the device proceeds with the qualification process, prompting the subject to provide information indicating whether the subject has developed symptoms of heart problems during sexual intercourse since receiving their last provision of the PDE$_5$ inhibitor pharmaceutical composition and then applies (814) the answer received from the subject to a sexual intercourse filter. When the sexual intercourse inhibitor filter is fired (e.g., when the answer indicates the subject has developed symptoms of heart problems during sexual intercourse since receiving their last provision of the PDE$_5$ inhibitor pharmaceutical composition), the device terminates (803,805) the qualification process without authorizing provision of the PDE$_5$ inhibitor pharmaceutical agent and, optionally, transmits advice to the user as to why they should not take the PDE$_5$ inhibitor pharmaceutical agent. In some embodiments, this advice is advice to seek immediate medical attention.

When the sexual intercourse filter is not fired, the device proceeds with the qualification process, prompting the subject to provide information indicating whether the subject has experienced priapism since receiving their last provision of the PDE$_5$ inhibitor pharmaceutical composition and then applies (816) the answer received from the subject to a priapism filter. When the priapism filter is fired (e.g., when the answer indicates the subject has experienced priapism since receiving their last provision of the PDE$_5$ inhibitor pharmaceutical composition), the device terminates (803, 805) the qualification process without authorizing provision of the PDE$_5$ inhibitor pharmaceutical agent and, optionally, transmits advice to the user as to why they should not take the PDE$_5$ inhibitor pharmaceutical agent.

When the priapism filter is not fired, the device proceeds with the qualification process, prompting the subject to provide information indicating whether the subject has developed vision loss since receiving their last provision of the PDE$_5$ inhibitor pharmaceutical composition and then applies (818) the answer received from the subject to a sensory deterioration filter. When the sensory deterioration is fired (e.g., when the answer indicates the subject has developed sudden vision loss since receiving their last provision of the PDE$_5$ inhibitor pharmaceutical composition), the device terminates (803,805) the qualification process without authorizing provision of the PDE$_5$ inhibitor pharmaceutical agent and, optionally, transmits advice to the user as to why they should not take the PDE$_5$ inhibitor pharmaceutical agent.

When the sensory deterioration filter is not fired, the device proceeds with the qualification process, prompting the subject to provide information indicating whether the subject has developed hearing loss since receiving their last provision of the PDE$_5$ inhibitor pharmaceutical composition and then applies (820) the answer received from the subject to the sensory deterioration filter. When the sensory deterioration is fired (e.g., when the answer indicates the subject has developed sudden hearing loss since receiving their last provision of the PDE$_5$ inhibitor pharmaceutical composition), the device terminates (803,805) the qualification process without authorizing provision of the PDE$_5$ inhibitor pharmaceutical agent and, optionally, transmits advice to the user as to why they should not take the PDE$_5$ inhibitor pharmaceutical agent. As previously described, in some embodiments the prompts and processes (818,820) associated with the sensory deterioration filter are combined as a single prompt and process.

When the sensory deterioration filter is not fired, the device proceeds with the qualification process, prompting the subject to provide information indicating whether the subject has developed a symptom of heart problems since receiving their last provision of the PDE$_5$ inhibitor pharmaceutical composition and then applies (822) the answer received from the subject to a heart problem filter. When the heart problem filter is fired (e.g. when the answer indicates that the subject has developed a heart problem since receiving their las provision of a PDE$_5$ inhibitor pharmaceutical composition), the device initiates (811-1) an override procedure (e.g., creates a record indicating that the user must confirm they have discussed taking a PDE$_5$ inhibitor pharmaceutical composition with a health care provider). When the heart problem filter is not fired (e.g., when the answer indicates the subject has not developed a heart problem), the device proceeds with the qualification process, prompting the subject to provide information indicating a pulmonary hypertension status and then applies (824) the answer received from the subject to a blood pressure filter. When the blood pressure filter is fired (e.g. when the answer indicates that the subject has developed pulmonary hypertension since receiving their las provision of a PDE$_5$ inhibitor pharmaceutical composition), the device initiates (811-2) an override procedure (e.g., creates a record indicating that the user must confirm they have discussed taking a PDE$_5$ inhibitor pharmaceutical composition with a health care provider). When the blood pressure filter is not fired, the device proceeds with the qualification process, prompting the subject to provide information indicating a blood pressure status and then applies (826) the answer received from the subject to the blood pressure filter. As previously described, in some embodiments the prompts and processes (824,826) associated with the blood pressure filter are combined as a single prompt and process. When the blood pressure filter is fired (e.g. when the answer indicates that the subject has developed low blood pressure or uncontrolled high blood pressure since receiving their las provision of a PDE$_5$ inhibitor pharmaceutical composition), the device initiates (811-3) an override procedure (e.g., creates a record indicating that the user must confirm they have discussed taking a PDE$_5$ inhibitor pharmaceutical composition with a health care provider). When the blood pressure filter is not fired (e.g., when the answer indicates the subject has not developed low blood pressure or uncontrolled high blood pressure), the device proceeds with the qualification process, prompting the subject to provide information indicating whether the subject has had a stroke since receiving their last provision of the PDE$_5$ inhibitor pharmaceutical composition and then applies (828) the answer received from the subject to a stroke filter. When the stroke filter is fired (e.g. when the answer indicates that the subject has experienced a stroke since receiving their las provision of a $PDE_5$ inhibitor pharmaceutical composition), the device initiates (811-4) an override procedure (e.g., creates a record indicating that the user must confirm they have discussed taking a $PDE_5$ inhibitor pharmaceutical composition with a health care provider). When the stroke filter is not fired (e.g., when the answer indicates the subject has not had a stroke since receiving their last provision of the $PDE_5$ inhibitor), the device proceeds with the qualification process, prompting the subject to provide information indicating whether the subject has developed a liver problem since receiving their last provision of the $PDE_5$ inhibitor pharmaceutical composition and then applies (830) the answer received from the subject to a liver disease filter. When the liver disease filter is fired (e.g. when the answer indicates that the subject has developed a liver problem since receiving their last provision of a $PDE_5$ inhibitor pharmaceutical composition), the device initiates (811-5) an override procedure (e.g., creates a record indicating that the user must confirm they have discussed taking a $PDE_5$ inhibitor pharmaceutical composition with a health care provider). When the liver disease filter is not fired (e.g., when the answer indicates the subject has not developed a liver problem), the device proceeds with the qualification process, prompting the subject to provide information indicating a kidney function status of the subject and then applies (832) the answer received from the subject to a kidney disease filter. When the kidney disease filter is fired (e.g. when the answer indicates that the subject has developed a kidney disease since receiving their last provision of a $PDE_5$ inhibitor pharmaceutical composition), the device initiates (811-6) an override procedure (e.g., creates a record indicating that the user must confirm they have discussed taking a $PDE_5$ inhibitor pharmaceutical composition with a health care provider). When the kidney disease filter is not fired (e.g., when the answer indicates the subject has not developed a kidney problem), the device proceeds with the qualification process, prompting the subject to provide information indicating whether the subject has developed retinitis pigmentosa since receiving their last provision of the $PDE_5$ inhibitor pharmaceutical composition and then applies (834) the answer received from the subject to a retinitis pigmentosa filter. When the retinitis pigmentosa filter is fired (e.g. when the answer indicates that the subject has developed retinitis pigmentosa since receiving their last provision of a $PDE_5$ inhibitor pharmaceutical composition) the device initiates (811-7) an override procedure (e.g., creates a record indicating that the user must confirm they have discussed taking a $PDE_5$ inhibitor pharmaceutical composition with a health care provider). When the retinitis pigmentosa filter is not fired (e.g., when the answer indicates the subject has not been diagnosed with retinitis pigmentosa), the device proceeds with the qualification process, prompting the subject to provide information indicating whether the subject has developed a stomach ulcer since receiving their last provision of the $PDE_5$ inhibitor pharmaceutical composition and then applies (836) the answer received from the subject to a stomach ulcer filter. When the stomach ulcer filter is fired (e.g. when the answer indicates that the subject has developed a stomach ulcer since receiving their last provision of a $PDE_5$ inhibitor pharmaceutical composition), the device initiates (811-8) an override procedure (e.g., creates a record indicating that the user must confirm they have discussed taking a $PDE_5$ inhibitor pharmaceutical composition with a health care provider). When the stomach ulcer filter is not fired (e.g., when the answer indicates the subject has not developed a stomach ulcer), the device proceeds with the qualification process, prompting the subject to provide information indicating whether the subject has developed a bleeding disorder since receiving their last provision of the $PDE_5$ inhibitor pharmaceutical composition and then applies (838) the answer received from the subject to a bleeding disorder filter. When the bleeding disorder filter is fired (e.g. when the answer indicates that the subject has developed a bleeding disorder since receiving their last provision of a $PDE_5$ inhibitor pharmaceutical composition), the device initiates (811-9) an override procedure (e.g., creates a record indicating that the user must confirm they have discussed taking a $PDE_5$ inhibitor pharmaceutical composition with a health care provider). When the bleeding disorder filter is not fired (e.g., when the answer indicates the subject has not developed a bleeding disorder), the device proceeds with the qualification process, prompting the subject to provide information indicating whether the subject has developed an abnormal genital shape since receiving their last provision of the $PDE_5$ inhibitor pharmaceutical composition and then applies (840) the answer received from the subject to a genital abnormality filter. When the genital abnormality filter is fired (e.g. when the answer indicates that the subject has developed pulmonary hypertension since receiving their last provision of a $PDE_5$ inhibitor pharmaceutical composition), the device initiates (811-10) an override procedure (e.g., creates a record indicating that the user must confirm they have discussed taking a $PDE_5$ inhibitor pharmaceutical composition with a health care provider). When the genital abnormality filter is not fired (e.g., when the answer indicates the subject has not developed an abnormal penile shape), the device proceeds with the qualification process, prompting the subject to provide information indicating whether the subject has developed a blood cell disorder since receiving their last provision of the $PDE_5$ inhibitor pharmaceutical composition and then applies (842) the answer received from the subject to a blood cell disorder filter. When the blood cell disorder filter is fired (e.g. when the answer indicates that the subject has developed a blood cell disorder since receiving their last provision of a $PDE_5$ inhibitor pharmaceutical composition), the device initiates (811-11) an override procedure (e.g., creates a record indicating that the user must confirm they have discussed taking a $PDE_5$ inhibitor pharmaceutical composition with a health care provider).

The device then proceeds with the qualification process, prompting the subject to provide information indicating whether the subject has started taking a medication that interacts with the $PDE_5$ inhibitor pharmaceutical composition since receiving their last provision of the $PDE_5$ inhibitor pharmaceutical composition and then applies (844-854) the answer received from the subject to a drug interaction filter. As previously described, in some embodiments the drug interaction filter comprises a plurality of filters, where each filter in the plurality of filters is configured for a specific drug interaction. For instance, in some embodiments the drug interaction filter comprises an alpha blocker filter, a hypertension medication filter, an HIV protease inhibitor filter, an oral antifungal, and other medications for treating erectile dysfunction. When the drug interaction filter is fired (e.g., when the answer indicates the subject is taking a medication that interacts with the $PDE_5$ inhibitor pharmaceutical composition), the device initiates (811-12-811-17) an override procedure (e.g., creates a record indicating that the user must confirm they have discussed taking a $PDE_5$ inhibitor pharmaceutical composition with a health care provider).

The device proceeds with the qualification process, determining (855) whether the override procedure has been triggered (e.g., by firing of one or more of the heart problem filter, the pulmonary hypertension filter, the blood pressure filter, the stroke filter, the liver disease filter, the kidney problem filter, the retinitis pigmentosa filter, the stomach ulcer filter, the bleeding problem filter, the genital abnormality filter, the blood cell disorder filter, the alpha blocker filter, the hypertension medication filter, the HIV protease inhibitor filter, the oral antifungal filter, the antibiotics filter, and/or the erectile dysfunction medication filter). If the override procedure has been triggered, the device prompts (817) the user to confirm that they have spoken with a medical professional about taking a $PDE_5$ inhibitor pharmaceutical composition (e.g., in view of the underlying risk factor that triggered the heart problem filter, the pulmonary hypertension filter, the blood pressure filter, the stroke filter, the liver disease filter, the kidney problem filter, the retinitis pigmentosa filter, the sensory deterioration filter, the stomach ulcer filter, the bleeding problem filter, the genital abnormality filter, the priapism filter, the blood cell disorder filter, the alpha blocker filter, the hypertension medication filter, the HIV protease inhibitor filter, the oral antifungal filter, the antibiotics filter, and/or the erectile dysfunction medication filter) and the medical professional recommended taking the $PDE_5$ inhibitor pharmaceutical composition. If the user's response indicates they have not spoken with a medical professional or the medical professional did not recommend taking the $PDE_5$ inhibitor pharmaceutical composition, the device terminates (803, 805) the process and, optionally, transmits advice for the subject to consult a medical professional.

If the override procedure was not triggered, or the override procedure was triggered and the subject's response indicated that a medical professional recommended they take a $PDE_5$ inhibitor pharmaceutical composition (e.g., in view of the underlying risk factor triggering the override procedure), the device proceeds with the qualification process, prompting (856) the subject to confirm their answers. If the user confirms their answers, the device transmits (831) a drug facts label for the $PDE_5$ inhibitor pharmaceutical composition and prompts the user to read the drug facts label. If the subject confirms they have read the drug facts label, the device proceeds to authorize (860) purchase of the $PDE_5$ inhibitor pharmaceutical composition.

Specific Embodiments

In one aspect, the disclosure provides methods, software, and computer systems for qualifying a human subject for over-the-counter delivery of a $PDE_5$ inhibitor pharmaceutical composition for treating erectile dysfunction. In one embodiment, a computer system (e.g., computer system 250 in FIG. 2) includes instructions for conducting a survey of the subject (e.g., including survey questions 208 and 212 administered via assessment module 252 in FIG. 2) to obtain information about the subject necessary to run against at least two series of filters (e.g., filters 216 and 222 in first filter category class 214-1 and second filter category class 220-2, respectively, in FIG. 2). The computer system also includes instructions for running the survey results against the filters. Filters 216 in the first series of filters 214 prevent authorization of a provision of the OTC $PDE_5$ inhibitor where the subject's survey results identify a contraindication for the OTC $PDE_5$ inhibitor. Filters 222 in the second series of filters 220 generate a warning 226 where the subject's survey results identify a risk factor for the OTC $PDE_5$ inhibitor. In some embodiments, the warning 226 includes a prompt requiring the subject to confirm they have discussed the risk factor with a physician in order to proceed with qualification for the OTC $PDE_5$ inhibitor.

In one aspect, the disclosure provides methods, software, and computer systems for re-qualifying a human subject for over-the-counter delivery of a $PDE_5$ inhibitor pharmaceutical composition for treating erectile dysfunction. In one embodiment, a computer system (e.g., computer system 250 in FIG. 2) includes instructions for conducting a survey of the subject (e.g., administered via reassessment module 254 in FIG. 2) to obtain information about the subject necessary to run against at least two series of filters. The computer system also includes instructions for running the survey results against the filters. Filters 216 in the third series of filters prevent authorization for delivery of the OTC $PDE_5$ inhibitor where the subject's survey results identify a contraindication for the OTC $PDE_5$ inhibitor. Filters 222 in the fourth series of filters generate a warning 226 where the subject's survey results identify a risk factor for the OTC $PDE_5$ inhibitor. In some embodiments, the warning 226 includes a prompt requiring the subject to confirm they have discussed the risk factor with a physician in order to proceed with qualification for the OTC $PDE_5$ inhibitor.

In one aspect, the disclosure provides a computer system for qualifying a human subject for over-the-counter delivery of a $PDE_5$ inhibitor pharmaceutical composition to treat erectile dysfunction. The computer system comprising one or more processors and a memory, the memory comprising non-transitory instructions which, when executed by the one or more processor, perform a method for qualifying a human subject for over-the-counter delivery of the $PDE_5$ inhibitor pharmaceutical composition. The method includes conducting a first survey of the subject thereby obtaining a first plurality of survey results necessary to run against a first plurality of filters of a first category class and a second plurality of filters of a second category class. The method also includes running all or a portion of the first plurality of survey results against a first plurality of filters of a first category class, wherein, when a respective filter in the first plurality of filters is fired, the subject is deemed not qualified for delivery of the $PDE_5$ inhibitor pharmaceutical composition and the method is terminated without delivery of the $PDE_5$ inhibitor pharmaceutical composition to the subject. The method also includes running all or a portion of the first plurality of survey results against a second plurality of filters of a second category class, wherein, when a respective filter in the second plurality of filters is fired, the subject is provided with a warning corresponding to the respective filter. The method also includes obtaining acknowledgment from the subject for the warning issued to the subject by any filter in the second plurality of filters. The method also includes proceeding with a fulfillment process when no filter in the first plurality of filters has been fired and the subject has acknowledged each warning associated with each filter in the second plurality of filters that was fired. The fulfillment process includes: storing an indication in a subject profile of an initial order for the $PDE_5$ inhibitor pharmaceutical composition, communicating an over-the-counter drug facts label for the $PDE_5$ inhibitor pharmaceutical composition to the subject, and authorizing, upon confirmation from the subject that the over-the-counter drug facts label has been received and read, provision of the $PDE_5$ inhibitor pharmaceutical composition to the subject. In some embodiments, the authorization includes a destination associated with the subject.

In some embodiments, the first plurality of survey results includes a plurality of survey results selected from the survey results listed in Table 1. In one embodiment, the first plurality of survey results indicates: a gender of the subject, an age of the subject, an erectile dysfunction status of the subject, whether the subject is taking a nitrate or nitrite vasodilator composition, whether the subject is taking a guanylate cyclase stimulator medication, whether the subject is taking a $PDE_5$ inhibitor composition, whether the subject has ever had a heart problem, a blood pressure status of the subject, whether the subject has ever had a stroke, whether the subject has a liver problem, a kidney function status of the subject, whether the subject has retinitis pigmentosa, whether the subject has developed vision loss, whether the subject has ever had a stomach ulcer, whether the subject has a bleeding disorder, a genital status of the subject, whether the subject has ever experienced priapism, whether the subject has a blood cell disorder, and whether the subject is taking a medication that interacts (e.g., a pharmacokinetic interaction and/or a pharmacodynamic interaction) with the $PDE_5$ inhibitor pharmaceutical composition.

In some embodiments, the first plurality of filters includes a plurality of filters selected from the filters listed in Table 2. In one embodiment, the first plurality of filters includes a gender filter, an age filter, an erectile dysfunction filter, a vasodilator filter, a guanylate cyclase stimulator filter, and a $PDE_5$ inhibitor filter.

In some embodiments, the second plurality of filters includes a plurality of filters selected from the filters listed in Table 3. In one embodiment, the second plurality of filters includes a heart problem filter, a blood pressure filter, a stroke filter, a liver disease filter, a kidney disease filter, a retinitis pigmentosa filter, a stomach ulcer filter, a bleeding problem filter, a genital abnormality filter, a priapism filter, a blood cell disorder, and a drug interaction filter.

In some embodiments, the first and second plurality of filters includes filters selected from the filters listed in Table 8. In some embodiments, the first plurality of filters of the first category class include a first sub-plurality of the filters listed in Table 8, for example, 2, 3, 4, 5, 6, 7, 8, 9, 10, 11, 12, 13, 14, 15, 16, 17, 18, or all 19 of the filters listed in Table 8, and the second plurality of filters of the first category class include a second sub-plurality of the filters listed in Table 8, which is different from the first sub-plurality of filters, for example, 2, 3, 4, 5, 6, 7, 8, 9, 10, 11, 12, 13, 14, 15, 16, 17, 18, or all 19 of the filters listed in Table 8. In some embodiments, each of the filters in the first sub-plurality of filters is different from each of the filters in the second sub-plurality of filters (e.g., no filter listed in Table 8 is included in both the first sub-plurality and the second sub-plurality of filters). In some embodiments, a system for qualifying a subject for delivery of an over-the-counter $PDE_5$ inhibitor pharmaceutical composition includes instructions for applying only one plurality of filters, e.g., only filters of a single category class of filters. In some embodiments, where the method, system, or software applies a single plurality of filters, the plurality of filters includes a plurality of filters selected from the filters listed in Table 8, e.g., at least 2, 3, 4, 5, 6, 7, 8, 9, 10, 11, 12, 13, 14, 15, 16, 17, 18, or all 19 of the filters listed in Table 8. In some embodiments, where a filter listed in Table 8 corresponds to a filter listed in Table 2 or Table 3, a threshold level sufficient to fire the corresponding filter listed in Table 2 or Table 3, as described in detail above, is sufficient to fire the filter listed in Table 8.

TABLE 8

Example filters for qualifying a subject for an over-the-counter provision of a $PDE_5$ inhibitor pharmaceutical composition

| Filter | Example Criteria |
|---|---|
| 1b | a gender filter |
| 2b | an age filter |
| 3b | an erectile dysfunction filter |
| 4b | a vasodilator filter |
| 5b | a guanylate cyclase filter |
| 6b | a $PDE_5$ inhibitor filter |
| 7b | a heart problem filter |
| 8b | a blood pressure filter |
| 9b | a stroke filter |
| 10b | a liver disease filter |
| 11b | a kidney disease filter |
| 12b | a retinitis pigmentosa filter |
| 13b | a vision deterioration filter |
| 14b | a stomach ulcer filter |
| 15b | a bleeding problem filter |
| 16b | a genital abnormality filter |
| 17b | a priapism filter |
| 18b | a blood cell disorder filter |
| 19b | a drug interaction filter |

In one aspect, the disclosure provides methods, software, and computer systems for qualifying a human subject for a re-order of an over-the-counter provision of a $PDE_5$ inhibitor pharmaceutical composition to treat erectile dysfunction. In one embodiment, a computer system includes instructions, responsive to receiving a re-order request from the subject for the $PDE_5$ inhibitor pharmaceutical composition, for performing a re-fulfillment procedure comprising conducting a second survey of the subject thereby obtaining a second plurality of survey results necessary to run against a third plurality of filters of a first category class and a fourth plurality of filters of a second category class. The method also includes running all or a portion of the second plurality of survey results against a third plurality of filters of a first category class, wherein, when a respective filter in the third plurality of filters is fired, the subject is deemed not qualified for delivery of the $PDE_5$ inhibitor pharmaceutical composition and the method is terminated without delivery of the $PDE_5$ inhibitor pharmaceutical composition to the subject. The method also includes running all or a portion of the second plurality of survey results against a fourth plurality of filters of a second category class, wherein, when a respective filter in the fourth plurality of filters is fired, the subject is provided with a warning corresponding to the respective filter. The method also includes obtaining acknowledgment from the subject for the warning issued to the subject by any filter in the fourth plurality of filters. The method also includes proceeding with a re-fulfillment process when no filter in the third plurality of filters has been fired and the subject has acknowledged each warning associated with each filter in the fourth plurality of filters that was fired. The re-fulfillment process includes: storing an indication in a subject profile of a re-order for the $PDE_5$ inhibitor pharmaceutical composition, communicating the over-the-counter drug facts label for $PDE_5$ inhibitor pharmaceutical composition to the subject, and authorizing, upon confirmation from the subject that the over-the-counter drug facts label has been received and read, provision of the $PDE_5$ inhibitor pharmaceutical composition to the subject.

In some embodiments, the third series of filters includes one or more filters listed in Table 5. In some embodiments, the third plurality of filters includes an erectile dysfunction filter, a vasodilator filter, a guanylate cyclase stimulator filter, a PDE$_5$ inhibitor filter, a sexual intercourse filter, a priapism filter, and a sensory deterioration filter.

In some embodiments, the fourth series of filters includes one or more filters listed in Table 6. In some embodiments, the fourth plurality of filters includes a heart problem filter, a blood pressure filter, a stroke filter, a liver disease filter, a kidney disease filter, a retinitis pigmentosa filter, a stomach ulcer filter, a bleeding problem filter, a genital abnormality filter, a blood cell disorder, and a drug interaction filter.

In some embodiments, the third and fourth plurality of filters includes filters selected from the filters listed in Table 9. In some embodiments, the third plurality of filters of the first category class include a third sub-plurality of the filters listed in Table 9, for example, 2, 3, 4, 5, 6, 7, 8, 9, 10, 11, 12, 13, 14, 15, 16, 17, or all 18 of the filters listed in Table 9, and the fourth plurality of filters of the first category class include a fourth sub-plurality of the filters listed in Table 9, which is different from the third sub-plurality of filters, for example, 2, 3, 4, 5, 6, 7, 8, 9, 10, 11, 12, 13, 14, 15, 16, 17, or all 18 of the filters listed in Table 9. In some embodiments, each of the filters in the third sub-plurality of filters is different from each of the filters in the fourth sub-plurality of filters (e.g., no filter listed in Table 9 is included in both the first sub-plurality and the second sub-plurality of filters). In some embodiments, a system for qualifying a subject for delivery of an over-the-counter PDE$_5$ inhibitor pharmaceutical composition includes instructions for applying only one plurality of filters, e.g., only filters of a single category class of filters. In some embodiments, where the method, system, or software applies a single plurality of filters, the plurality of filters includes a plurality of filters selected from the filters listed in Table 9, e.g., at least 2, 3, 4, 5, 6, 7, 8, 9, 10, 11, 12, 13, 14, 15, 16, 17, or all 18 of the filters listed in Table 9. In some embodiments, where a filter listed in Table 9 corresponds to a filter listed in Table 2, Table 3, Table 5, or Table 6, a threshold level sufficient to fire the corresponding filter listed in Table 2, Table 3, Table 5, or Table 6, as described in detail above, is sufficient to fire the filter listed in Table 9.

TABLE 9

Example filters for re-qualifying a subject for an over-the-counter provision of a PDE$_5$ inhibitor pharmaceutical composition

| Filter | Example Criteria |
| --- | --- |
| 1b | an erectile dysfunction filter |
| 2b | a vasodilator filter |
| 3b | a guanylate cyclase stimulator filter |
| 4b | a PDE$_5$ inhibitor filter |
| 5b | a sexual intercourse filter |
| 6b | a priapism filter |
| 7b | a deterioration filter |
| 8b | a heart problem filter |
| 9b | a blood pressure filter |
| 10b | a stroke filter |
| 11b | a liver disease filter |
| 12b | a kidney disease filter |
| 13b | a retinitis pigmentosa filter |
| 14b | a stomach ulcer filter |
| 15b | a bleeding problem filter |
| 16b | a genital abnormality filter |
| 17b | a blood cell disorder filter |
| 18b | a drug interaction filter |

In one aspect, the present disclosure provides a computer system for qualifying a human subject for over-the-counter delivery of a PDE$_5$ inhibitor pharmaceutical composition for treating erectile dysfunction, the computer system comprising one or more processors and a memory, the memory comprising non-transitory instructions which, when executed by the one or more processor, perform a method comprising: a) conducting a first survey of the subject thereby obtaining a first plurality of survey results, wherein the first plurality of survey results indicates: a gender of the subject, an age of the subject, an erectile dysfunction status of the subject, whether the subject is taking a nitrate or nitrite vasodilator composition, whether the subject is taking a guanylate cyclase stimulator medication, whether the subject is taking a PDE$_5$ inhibitor composition, whether the subject has ever had a heart problem, a blood pressure status of the subject, whether the subject has ever had a stroke, whether the subject has a liver problem, a kidney function status of the subject, whether the subject has retinitis pigmentosa, whether the subject has developed vision loss, whether the subject has ever had a stomach ulcer, whether the subject has a bleeding disorder, a genital status of the subject, whether the subject has ever experienced priapism, whether the subject has a blood cell disorder, and whether the subject is taking a medication that interacts (e.g., a pharmacokinetic interaction and/or a pharmacodynamic interaction) with the PDE$_5$ inhibitor pharmaceutical composition; b) running all or a portion of the first plurality of survey results against a first plurality of filters of a first category class, wherein, when a respective filter in the first plurality of filters is fired, the subject is deemed not qualified for delivery of the PDE$_5$ inhibitor pharmaceutical composition and the method is terminated without delivery of the PDE$_5$ inhibitor pharmaceutical composition to the subject, wherein the first plurality of filters comprises: a gender filter that is fired when the first plurality of survey results indicates that the subject is not male, an age filter, a first erectile dysfunction filter that is fired at least when the first plurality of survey results indicates that the subject does not have erectile dysfunction, a first vasodilator filter that is fired at least when the first plurality of survey results indicates that the subject is taking a vasodilator composition comprising a nitrate or a nitrite, a first guanylate cyclase stimulator filter that is fired at least when the first plurality of survey results indicates that the subject is taking a guanylate cyclase stimulator mediation, and a first PDE$_5$ inhibitor filter that is fired at least when the first plurality of survey results indicates that the subject is taking a PDE$_5$ inhibitor composition; c) running all or a portion of the first plurality of survey results against a second plurality of filters of a second category class, wherein, when a respective filter in the second plurality of filters is fired, the subject is provided with a warning corresponding to the respective filter, and wherein the second plurality of filters comprises: a first heart problem filter that is fired at least when the first plurality of survey results indicates that the subject has had a heart problem, a first blood pressure filter that this fired at least when the first plurality of survey results indicates that the subject has either low blood pressure, uncontrolled high blood pressure, or pulmonary hypertension, a first stroke filter that is fired at least when the first plurality of survey results indicates that the subject has had a stroke, a first liver disease filter that is fired at least when the first plurality of survey results indicates that the subject has a liver problem, a first kidney disease filter that is fired at least when the first plurality of survey results indicates that the subject has a kidney problem, and a first retinitis pigmentosa filter that is fired at least when the first plurality of survey results indicates that the subject has retinitis pigmentosa, a first vision deterioration filter that is fired at least when the first plurality of survey results indicates that the subject has had severe vision loss, a first stomach ulcer filter that is fired at least when the first plurality of survey results indicates that the subject has had a stomach ulcer, a first bleeding problem filter that is fired at least when the first plurality of survey results indicates that the subject has a bleeding disorder, a first genital abnormality filter that is fired at least when the first plurality of survey results indicates that the subject has an abnormal penile shape, a first priapism filter that is fired at least when the first plurality of survey results indicates that the subject has experienced priapism, a first blood cell disorder filter that is fired at least when the first plurality of survey results indicates that the subject has a blood cell disorder selected from the group consisting of sickle cell anemia, multiple myeloma, and leukemia, a first drug interaction filter that is fired at least when the first plurality of survey results indicates that the subject is taking a medication that interacts with the $PDE_5$ inhibitor pharmaceutical composition; d) obtaining acknowledgment from the subject for the warning issued to the subject by any filter in the second plurality of filters; and e) proceeding with a fulfillment process when (i) no filter in the first plurality of filters has been fired and (ii) the subject has acknowledged each warning associated with each filter in the second plurality of filters that was fired, wherein the fulfillment process comprises: storing an indication in a subject profile of an initial order for the $PDE_5$ inhibitor pharmaceutical composition, communicating an over-the-counter drug facts label for the $PDE_5$ inhibitor pharmaceutical composition to the subject, and authorizing, upon confirmation from the subject that the over-the-counter drug facts label has been received and read, provision of the $PDE_5$ inhibitor pharmaceutical composition to the subject.

In some embodiments, the $PDE_5$ inhibitor pharmaceutical composition has the structure:

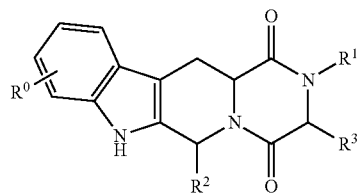

where: $R^0$ represents hydrogen, halogen or $C_{1-6}$ alkyl; $R^1$ represents hydrogen, $C_{1-6}$ alkyl, $C_{2-6}$ alkenyl, $C_{2-6}$ alkynyl, halo$C_{1-6}$ alkyl, $C_{3-8}$ cycloalkyl, $C_{3-8}$ cycloalkyl-$C_{1-3}$ alkyl, aryl$C_{1-3}$ alkyl or heteroaryl$C_{1-3}$ alkyl; $R^2$ represents an optionally substituted mono-cyclic aromatic ring selected from benzene, thiophene, furan and pyridine or an optionally substituted bicyclic ring

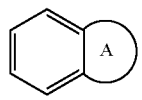

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and $R^3$ represents hydrogen or C1-3 alkyl, or $R^1$ and $R^3$ together represent a 3- or 4-membered alkyl or alkenyl chain, or a pharmaceutically acceptable salt thereof.

In some embodiments, the $PDE_5$ inhibitor pharmaceutical composition includes tadalafil. In some embodiments, the $PDE_5$ inhibitor includes a pharmaceutically acceptable salt of tadalafil.

In some embodiments, upon confirmation from the subject that the over the counter drug facts label has been received and read, the subject is authorized for provision of a dosage of from 2.5 mg to 10 mg of tadalafil no more than once per day.

In some embodiments, upon confirmation from the subject that the over the counter drug facts label has been received and read, the subject is authorized for provision of a dosage of 5 mg of tadalafil no more than once per day.

In some embodiments, the $PDE_5$ inhibitor pharmaceutical composition includes vardenafil.

In some embodiments, upon confirmation from the subject that the over the counter drug facts label has been received and read, the subject is authorized for provision of a dosage of from 2.5 mg to 20 mg of vardenafil no more than once per day.

In some embodiments, upon confirmation from the subject that the over the counter drug facts label has been received and read, the subject is authorized for provision of a dosage of 5 mg of vardenafil no more than once per day.

In some embodiments, the age filter is fired when the first plurality of survey results indicates that the subject is less than eighteen years old.

In some embodiments, the vasodilator composition, which is capable of firing the first vasodilator filter, includes a compound selected from the group consisting of nitroglycerin, amyl nitrate, amyl nitrite, and butyl nitrate.

In some embodiments, the heart problem, which is capable of firing the first heart problem filter, is selected from the group consisting of a heart attack, arrhythmia, angina, chest pain, narrowing of the aortic valve, and heart failure.

In some embodiments, the first drug interaction filter is fired when the first plurality of survey results indicates that the subject is taking a medication selected from the group consisting of an alpha blocker, an HIV protease inhibitor, an antifungal medication, an antibiotic, a blood pressure medication, and an erectile dysfunction medication.

In some embodiments, the warning corresponding to a respective filter in the second plurality of filters comprises a prompt for the subject to indicate whether they have discussed the risk factor underlying the respective filter in the second plurality of filters that was fired with a health care provider. Acknowledgement is obtained from the subject when the subject indicates that they have discussed the risk factor underlying the respective filter in the second plurality of filters that was fired with a health care provider.

In some embodiments, the fulfillment process further comprises storing a destination associated with the subject in the subject profile.

In some embodiments, coordinating shipping of the $PDE_5$ inhibitor pharmaceutical composition to a physical address associated with the subject.

In some embodiments of the aspects disclosed above, the method further comprises: f) responsive to receiving a re-order request from the subject for the $PDE_5$ inhibitor pharmaceutical composition, performing a re-fulfillment procedure comprising: (i) conducting a second survey of the subject thereby obtaining a second plurality of survey results, wherein the second plurality of survey results indicates: an erectile dysfunction status of the subject, whether the subject has started to take a nitrate or nitrite vasodilator composition since receiving their last provision of the $PDE_5$ inhibitor pharmaceutical composition, whether the subject has started to take a guanylate cyclase stimulator medication since receiving their last provision of the $PDE_5$ inhibitor pharmaceutical composition, whether the subject has started to take a $PDE_5$ inhibitor composition since receiving their last provision of the $PDE_5$ inhibitor pharmaceutical composition, whether the subject has developed symptoms of heart problems during sexual intercourse since receiving their last provision of the $PDE_5$ inhibitor pharmaceutical composition, whether the subject has experienced priapism since receiving their last provision of the $PDE_5$ inhibitor pharmaceutical composition, whether the subject has developed hearing or vision loss since receiving their last provision of the $PDE_5$ inhibitor pharmaceutical composition, whether the subject has developed symptoms of heart problems since receiving their last provision of the $PDE_5$ inhibitor pharmaceutical composition, a blood pressure status of the subject, whether the subject has had a stroke since receiving their last provision of the $PDE_5$ inhibitor pharmaceutical composition, whether the subject has developed a liver problem since receiving their last provision of the $PDE_5$ inhibitor pharmaceutical composition, a kidney function status of the subject, whether the subject has developed retinitis pigmentosa since receiving their last provision of the $PDE_5$ inhibitor pharmaceutical composition, whether the subject has developed a stomach ulcer since receiving their last provision of the $PDE_5$ inhibitor pharmaceutical composition, whether the subject has developed a bleeding disorder since receiving their last provision of the $PDE_5$ inhibitor pharmaceutical composition, whether the subject has developed an abnormal genital shape since receiving their last provision of the $PDE_5$ inhibitor pharmaceutical composition, whether the subject has developed a blood cell disorder since receiving their last provision of the $PDE_5$ inhibitor pharmaceutical composition, and whether the subject has started taking a medication that interacts with the $PDE_5$ inhibitor pharmaceutical composition since receiving their last provision of the $PDE_5$ inhibitor pharmaceutical composition; (ii) running all or a portion of the second plurality of survey results against a third plurality of filters of the first category class, wherein, when a respective filter in the third plurality of filters is fired, the subject is deemed not qualified for the $PDE_5$ inhibitor pharmaceutical composition and the re-fulfillment process is terminated without delivery of the $PDE_5$ inhibitor pharmaceutical composition to the subject, wherein the third plurality of filters comprise: a second erectile dysfunction filter that is fired at least when the second plurality of survey results indicates that the subject does not have erectile dysfunction, a second vasodilator filter that is fired at least when the second plurality of survey results indicates that the subject is taking a vasodilator composition comprising a nitrate or a nitrite, a second guanylate cyclase stimulator filter that is fired at least when the second plurality of survey results indicates that the subject is taking a guanylate cyclase stimulator mediation, a second $PDE_5$ inhibitor filter that is fired at least when the second plurality of survey results indicates that the subject is taking a $PDE_5$ inhibitor composition, a sexual intercourse filter that is fired at least when the second plurality of survey results indicates that the subject has developed symptoms of heart problems during sexual intercourse since receiving their last provision of the $PDE_5$ inhibitor pharmaceutical composition, a second priapism filter that is fired at least when the second plurality of survey results indicates that the subject has had priapism since receiving their last provision of the $PDE_5$ inhibitor pharmaceutical composition, and a sensory deterioration filter that is fired at least when the second plurality of survey results indicates that the subject has developed sudden vision loss or sudden hearing loss since receiving their last provision of the cGMP-specific phosphodiesterase 5 ($PDE_5$) inhibitor pharmaceutical composition; (iii) running all or a portion of the second plurality of survey results against a fourth plurality of filters of the second category class, wherein, when a respective filter in the fourth plurality of filters is fired, the subject is provided with a warning corresponding to the respective filter, and wherein the fourth plurality of filters comprises: a second heart problem filter that is fired at least when the second plurality of survey results indicates that the subject has developed a heart problem since receiving their last provision of the $PDE_5$ inhibitor pharmaceutical composition, a second blood pressure filter that this fired at least when the second plurality of survey results indicates that the subject has developed either low blood pressure, uncontrolled high blood pressure, or pulmonary hypertension, a second stroke filter that is fired at least when the second plurality of survey results indicates that the subject has had a stroke since receiving their last provision of the $PDE_5$ inhibitor pharmaceutical composition, a second liver disease filter that is fired at least when the second plurality of survey results indicates that the subject has developed liver disease since receiving their last provision of the $PDE_5$ inhibitor pharmaceutical composition, a second kidney disease filter that is fired at least when the second plurality of survey results indicates that the subject has developed a kidney problem since receiving their last provision of the $PDE_5$ inhibitor pharmaceutical composition, a second retinitis pigmentosa filter that is fired at least when the second plurality of survey results indicates that the subject has been diagnosed with retinitis pigmentosa since receiving their last provision of the $PDE_5$ inhibitor pharmaceutical composition, a second stomach ulcer filter that is fired at least when the second plurality of survey results indicates that the subject has developed a stomach ulcer since receiving their last provision of the $PDE_5$ inhibitor pharmaceutical composition, a second bleeding problem filter that is fired at least when the second plurality of survey results indicates that the subject has developed a bleeding disorder since receiving their last provision of the $PDE_5$ inhibitor pharmaceutical composition, a second genital abnormality filter that is fired at least when the second plurality of survey results indicates that the subject has developed an abnormal genital shape since receiving their last provision of the $PDE_5$ inhibitor pharmaceutical composition, a second blood cell disorder filter that is fired at least when the second plurality of survey results indicates that the subject has developed a blood disorder selected from the group consisting of sickle cell anemia, multiple myeloma, and leukemia, since receiving their last provision of the $PDE_5$ inhibitor pharmaceutical composition, and a second drug interaction filter that is fired at least when the second plurality of survey results indicates that the subject has started taking a medication that interacts with the $PDE_5$ inhibitor pharmaceutical composition since receiving their last provision of the $PDE_5$ inhibitor pharmaceutical composition; (iv) obtaining acknowledgment from the subject for the warning issued to the subject by any filter in the fourth plurality of filters; and (v) proceeding with the re-fulfillment process when (a) the re-fulfillment process is not already terminated by the firing of a filter in the third plurality of filters and (b) the subject has acknowledged each warning associated with each filter in the fourth plurality of filters that was fired, wherein the re-fulfillment process further comprises: storing an indication in the subject profile of a re-order for the $PDE_5$ inhibitor pharmaceutical composition, communicating the over-the-counter drug facts label for the $PDE_5$ inhibitor pharmaceutical composition to the subject, and authorizing, upon confirmation from the subject that the over-the-counter drug facts label has been received and read, a re-order provision of the $PDE_5$ inhibitor pharmaceutical composition to the subject.

In some embodiments of the aspects disclosed above, the second plurality of survey results further comprises whether the subject has side effects associated with the $PDE_5$ inhibitor pharmaceutical composition since receiving their last provision of the $PDE_5$ inhibitor pharmaceutical composition, and the fourth plurality of filters further comprises a side effect filter that is fired at least when the second plurality of survey results indicates that the subject has developed, since receiving their last provision of the $PDE_5$ inhibitor pharmaceutical composition, a side effect selected from the group consisting of headaches, abnormal vision, muscle pain, nausea, dizziness, and a skin rash.

In some embodiments of the aspects disclosed above, the re-fulfillment process further comprises, when a respective filter in the third plurality of filters or fourth plurality of filters is fired, storing a record associated with the firing of the respective filter in an adverse event profile comprising records of filter firing events associated with a plurality of subjects.

In one aspect, the disclosure provides a method for treating erectile dysfunction in a subject in need thereof, the method comprising: administering a (e.g., low-dose) $PDE_5$ inhibitor pharmaceutical composition to a subject qualified for over-the-counter access to the $PDE_5$ inhibitor pharmaceutical composition. In some embodiments, the subject is qualified for the over-the-counter access to the $PDE_5$ inhibitor composition using a method, system, or computer readable medium disclosed herein.

In some embodiments, the $PDE_5$ inhibitor pharmaceutical composition has the structure:

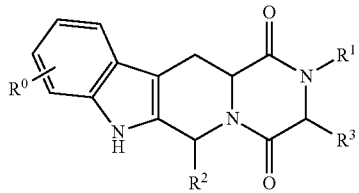

where: $R^0$ represents hydrogen, halogen or $C_{1-6}$ alkyl; $R^1$ represents hydrogen, $C_{1-6}$ alkyl, $C_{2-6}$ alkenyl, $C_{2-6}$ alkynyl, $haloC_{1-6}$ alkyl, $C_{3-8}$ cycloalkyl, $C_{3-8}$ cycloalkyl-$C_{1-3}$ alkyl, $arylC_{1-3}$ alkyl or heteroaryl$C_{1-3}$ alkyl; $R^2$ represents an optionally substituted mono-cyclic aromatic ring selected from benzene, thiophene, furan and pyridine or an optionally substituted bicyclic ring

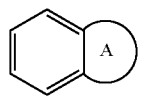

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and $R^3$ represents hydrogen or C1-3 alkyl, or $R^1$ and $R^3$ together represent a 3- or 4-membered alkyl or alkenyl chain, or a pharmaceutically acceptable salt thereof.

In some embodiments, the $PDE_5$ inhibitor pharmaceutical composition includes tadalafil or a pharmaceutically acceptable salt thereof.

In some embodiments, upon confirmation from the subject that the over the counter drug facts label has been received and read, the subject is authorized for provision of a dosage of from 2.5 mg to 10 mg of tadalafil no more than once per day.

In some embodiments, upon confirmation from the subject that the over the counter drug facts label has been received and read, the subject is authorized for provision of a dosage of 5 mg of tadalafil no more than once per day.

In some embodiments, the $PDE_5$ inhibitor pharmaceutical composition includes vardenafil.

In some embodiments, upon confirmation from the subject that the over the counter drug facts label has been received and read, the subject is authorized for provision of a dosage of from 2.5 mg to 20 mg of vardenafil no more than once per day.

In some embodiments, upon confirmation from the subject that the over the counter drug facts label has been received and read, the subject is authorized for provision of a dosage of 5 mg of vardenafil no more than once per day.

In some embodiments, the disclosure provides methods for treating erectile dysfunction with an over the counter cGMP-specific phosphodiesterase 5 ($PDE_5$) inhibitor pharmaceutical composition. The method includes providing a first survey for obtaining a first information set from the human, via a computer system having a processor programmed to perform the first survey, where the first information set includes information about the human that relates to potential risk factors and contraindications for the cGMP-specific phosphodiesterase 5 ($PDE_5$) inhibitor pharmaceutical composition, as described herein. The method also includes applying an algorithm to the first information set, via a computer system having a processor programmed to perform the algorithm. The algorithm runs all or a portion of the first information set against a first plurality of filters, where the human is deemed not qualified for treatment with the over the counter cGMP-specific phosphodiesterase 5 ($PDE_5$) inhibitor pharmaceutical composition for treating erectile dysfunction when a respective filter in the first plurality of filters is fired and the method is terminated without authorizing provision of the cGMP-specific phosphodiesterase 5 ($PDE_5$) inhibitor pharmaceutical composition to the human, where the first plurality of filters includes filters related to contraindications of the cGMP-specific phosphodiesterase 5 ($PDE_5$) inhibitor pharmaceutical composition as described herein. The algorithm also runs all or a portion of the first information set against a second plurality of filters, where, when a respective filter in the second plurality of filters is fired, the human is provided with a warning corresponding to the respective filter, and where the second plurality of filters includes filters related to risk factors for the cGMP-specific phosphodiesterase 5 ($PDE_5$) inhibitor pharmaceutical composition as described herein. The algorithm also obtains acknowledgment from the human of the risk factor associated with each warning issued to the human by any filter in the second plurality of filters. In some embodiments, the acknowledgement includes confirmation that the human has discussed the risk factor with a physician. The algorithm proceeds with a fulfillment process when (a) no filter in the first plurality of filters has been fired and (b) the human has acknowledged each warning associated with each filter in the second plurality of filters that was fired. The fulfillment process includes storing an indication in a subject profile of an initial order for the cGMP-specific phosphodiesterase 5 ($PDE_5$) inhibitor pharmaceutical composition, communicating an over the counter drug facts label for the cGMP-specific phosphodiesterase 5 ($PDE_5$) inhibitor pharmaceutical composition to the human, and authorizing, upon confirmation from the subject that the over the counter drug facts label has been received and read, provision of the cGMP-specific phosphodiesterase 5 ($PDE_5$) inhibitor pharmaceutical composition to the human, where the authorization includes a destination associated with the subject. In some embodiments, the method also includes treating the human to treat erectile dysfunction of the human, upon authorization of the provision e.g., by providing access to the cGMP-specific phosphodiesterase 5 ($PDE_5$) inhibitor pharmaceutical composition to the human and/or by administering the cGMP-specific phosphodiesterase 5 ($PDE_5$) inhibitor pharmaceutical composition to treat erectile dysfunction in the human.

EXAMPLES

Example 1

A computer system is configured for qualifying a subject for over-the-counter delivery of an tadalafil pharmaceutical composition (e.g., (6R,12aR)-6-(1,3-benzodioxol-5-yl)-2-methyl-2,3,6,7,12,12a-hexahydropyrazino[1',2':1,6]pyrido[3,4-b]indole-1,4-dione) to treat erectile dysfunction. The computer system includes instructions for conducting a survey of the subject. The survey is utilized to obtain one or more results of: a gender of the subject, an age of the subject, an erectile dysfunction status of the subject, whether the subject is taking a nitrate or nitrite vasodilator composition, whether the subject is taking a guanylate cyclase stimulator medication, whether the subject is taking a $PDE_5$ inhibitor composition, whether the subject has ever had a heart problem, a blood pressure status of the subject, whether the subject has ever had a stroke, whether the subject has a liver problem, a kidney function status of the subject, whether the subject has retinitis pigmentosa, whether the subject has developed vision loss, whether the subject has ever had a stomach ulcer, whether the subject has a bleeding disorder, a genital status of the subject, whether the subject has ever experienced priapism, whether the subject has a blood cell disorder, and whether the subject is taking a medication that interacts (e.g., a pharmacokinetic interaction and/or a pharmacodynamic interaction) with the tadalafil pharmaceutical composition.

The computer system runs survey results against a first series of filters that are each associated with a first filter category class. The first filter category class is configured to prevent authorization for OTC delivery of the OTC tadalafil when the subject's survey results identify a contraindication for the tadalafil. In some embodiments, the first series of filters includes one or more of a gender filter, an age filter, a first erectile dysfunction filter, a first vasodilator filter, a first guanylate cyclase stimulator filter, and a first $PDE_5$ inhibitor filter. The gender filter is configured to ensure the subject is male. The age filter is configured to ensure that the subject is eighteen years old or older. The erectile dysfunction filter is configured to ensure the subject has erectile dysfunction. The vasodilator filter is configured to ensure the subject is not taking an organic nitrate or nitrite. The guanylate cyclase stimulator is configured to ensure the subject is not taking a guanylate cyclase stimulator. Furthermore, the $PDE_5$ inhibitor is configured to ensure the subject is not taking additional $PDE_5$ inhibitors.

The computer system runs survey results against a second series of filters that each generates a warning where the subject's survey results identify a risk factor for the OTC tadalafil. In some embodiments, the second series of filters comprises a first heart problem filter, a first blood pressure filter, a first stroke filter, a first liver disease filter, a first kidney disease filter, a first retinitis pigmentosa filter, a first stomach ulcer filter, a first bleeding problem filter, a first genital abnormality filter, a first priapism filter, a first blood cell disorder, and a first drug interaction filter. The first heart problem filter is configured to ensure the subject has not developed heart problems. The first stroke filter is configured to ensure the subject has not had a stroke. The first liver disease filter is configured to ensure that the subject has adequate liver function. The first kidney disease filter is configured to ensure that the subject has adequate kidney function. The first retinitis pigmentosa filter is configured to ensure that the subject does not have a variety of vision conditions. The first stomach ulcer filter is configured to ensure that the subject has not had a stomach ulcer. The first bleeding problem filter is configured to ensure that the subject does not have a bleeding problem (e.g., a coagulation problem). The first genital abnormality filter is configured to ensure that the subject has a normal penile shape. The first priapism filter is configured to ensure that the subject has not experienced priapism. The first blood cell disorder filter is configured to ensure the subject has normal blood cells. The first drug interaction filter is configured to ensure the subject is not taking a substance that interacts with tadalafil. Substances that interact with tadalafil, and are therefore capable of firing the first drug interaction filter, include an alpha blocker (e.g., terazosin, tamsulosin, doxazosin mesylate, prazosin HCl, alfuzosin, dutasteride and tamsulosin HCl, and silodosin), an HIV protease inhibitor (e.g., ritonavir), an antifungal medication (e.g., ketoconazole and itraconazole), an antibiotic (e.g., clarithromycin, telithromycin, and erythromycin), a blood pressure medication (e.g., a medication to treat hypertension), and an erectile dysfunction medication.

The computer system then prompts the subject to acknowledge or deny having discussed these warnings with a medical professional (e.g., their physician or healthcare provider). The computer system then proceeds with a fulfillment process only when none of the first series of filters was fired and the subject acknowledged that they discussed each warning issued in association with the second series of filters that was fired.

The computer system stores an indication of an initial order of the OTC tadalafil in a subject profile, and communicates an over-the-counter drug facts label for the tadalafil pharmaceutical composition to the subject. Upon confirmation from the subject that they have received and read the over-the-counter drug facts label, the computer system authorizes provision of the OTC tadalafil pharmaceutical composition to the subject.

In some embodiments, the computer system includes instructions for conducting another survey of the subject responsive to a re-order request of the tadalafil pharmaceutical composition. This survey is utilized to obtain one or more results of: an erectile dysfunction status of the subject, whether the subject has started to take a nitrate or nitrite vasodilator composition since receiving their last provision of tadalafil, whether the subject has started to take a guanylate cyclase stimulator medication since receiving their last provision of tadalafil, whether the subject has started to take a $PDE_5$ inhibitor composition since receiving their last provision of tadalafil, whether the subject has developed symptoms of heart problems during sexual intercourse since receiving their last provision of tadalafil, whether the subject has experienced priapism since receiving their last provision of tadalafil, whether the subject has developed hearing or vision loss since receiving their last provision of tadalafil, whether the subject has developed a symptom of heart problems since receiving their last provision of tadalafil, a blood pressure status of the subject, whether the subject has had a stroke since receiving their last provision of tadalafil, whether the subject has developed a liver problem since receiving their last provision of tadalafil, a kidney function status of the subject, whether the subject has developed retinitis pigmentosa since receiving their last provision of tadalafil, whether the subject has developed a stomach ulcer since receiving their last provision of tadalafil, whether the subject has developed a bleeding disorder since receiving their last provision of tadalafil, whether the subject has developed an abnormal genital shape since receiving their last provision of tadalafil, whether the subject has developed a blood cell disorder since receiving their last provision of tadalafil, and whether the subject has started taking a medication that interacts with tadalafil since receiving their last provision of tadalafil.

The computer system runs survey results against a third series of filters that are each associated with the first filter category class. In some embodiments, the third series of filters includes one or more of a second erectile dysfunction filter, a second vasodilator filter, a second guanylate cyclase stimulator filter, a second $PDE_5$ inhibitor filter, a sexual intercourse filter, a second priapism filter, and a sensory deterioration filter. The second erectile dysfunction filter is configured to ensure the subject has erectile dysfunction. The second vasodilator filter is configured to ensure the subject is not taking an organic nitrate or nitrite since receiving their last provision of tadalafil. The second guanylate cyclase stimulator is configured to ensure the subject is not taking a guanylate cyclase stimulator since receiving their last provision of tadalafil. The second $PDE_5$ inhibitor is configured to ensure the subject is not taking additional $PDE_5$ inhibitors since receiving their last provision of tadalafil. The sexual intercourse filter is configured to ensure the subject has not developed heart problems during sexual intercourse since receiving their last provision of tadalafil. The second priapism filter is configured to ensure that the subject has not experienced priapism since receiving their last provision of tadalafil. The sensory deterioration filter is configured to ensure that the subject has not developed hearing loss or vision loss since receiving their last provision of tadalafil.

The computer system runs survey results against a fourth series of filters that each generates a warning where the subject's survey results identify a risk factor for the OTC tadalafil. In some embodiments, the fourth series of filters comprises a second heart problem filter, a second blood pressure filter, a second stroke filter, a second liver disease filter, a second kidney disease filter, a second retinitis pigmentosa filter, a second stomach ulcer filter, a second bleeding problem filter, a second genital abnormality filter, a second blood cell disorder, and a second drug interaction filter. The second heart problem filter is configured to ensure the subject has not developed heart problems since receiving their last provision of tadalafil. The second stroke filter is configured to ensure the subject has not had a stroke since receiving their last provision of tadalafil. The second liver disease filter is configured to ensure that the subject has adequate liver function since receiving their last provision of tadalafil. The second kidney disease filter is configured to ensure that the subject has adequate kidney function since receiving their last provision of tadalafil. The second retinitis pigmentosa filter is configured to ensure that the subject has not developed a variety of vision conditions since receiving their last provision of tadalafil. The second stomach ulcer filter is configured to ensure that the subject has not had a stomach ulcer since receiving their last provision of tadalafil. The second bleeding problem filter is configured to ensure that the subject does not have a bleeding problem (e.g., a coagulation problem) since receiving their last provision of tadalafil. The second genital abnormality filter is configured to ensure that the subject has a normal penile shape since receiving their last provision of tadalafil. The second priapism filter is configured to ensure that the subject has not experienced priapism since receiving their last provision of tadalafil. The second blood cell disorder filter is configured to ensure the subject has normal blood cells since receiving their last provision of tadalafil. The second drug interaction filter is configured to ensure the subject is not taking a substance that interacts with tadalafil since receiving their last provision of tadalafil. Substances that interact with tadalafil, and are therefore capable of firing the first drug interaction filter, include an alpha blocker (e.g., terazosin, tamsulosin, doxazosin mesylate, prazosin HCl, alfuzosin, dutasteride and tamsulosin HCl, and silodosin), an HIV protease inhibitor (e.g., ritonavir), an antifungal medication (e.g., ketoconazole and itraconazole), an antibiotic (e.g., clarithromycin, telithromycin, and erythromycin), a blood pressure medication (e.g., a medication to treat hypertension), and an erectile dysfunction medication.

The computer system then prompts the subject to acknowledge or deny having discussed these warnings with a medical professional (e.g., their physician or healthcare provider). The computer system then proceeds with a re-fulfillment process only when none of the third series of filters was fired the subject acknowledged that they discussed each warning issued in association with the fourth series of filters that was fired.

The computer system stores an indication of a re-order of the OTC tadalafil in the subject profile, and communicates the over-the-counter drug facts label for the tadalafil pharmaceutical composition to the subject. Upon confirmation from the subject that they have received and read the over-the-counter drug facts label, the computer system authorizes provision of the OTC tadalafil pharmaceutical composition to the subject.

Example 2

A computer system is configured for qualifying a subject for over-the-counter delivery of a vardenafil pharmaceutical composition (e.g., 4-[2-Ethoxy-5-(4-ethylpiperazin-1-yl)sulfonyl-phenyl]-9-methyl-7-propyl-3,5,6,8-tetrazabicyclo[4.3.0]nona-3,7,9-trien-2-one) to treat erectile dysfunction. The computer system includes instructions for conducting a survey of the subject. The survey is utilized to obtain one or more results of: a gender of the subject, an age of the subject, an erectile dysfunction status of the subject, whether the subject is taking a nitrate or nitrite vasodilator composition, whether the subject is taking a guanylate cyclase stimulator medication, whether the subject is taking a $PDE_5$ inhibitor composition, whether the subject has ever had a heart problem, a blood pressure status of the subject, whether the subject has ever had a stroke, whether the subject has a liver problem, a kidney function status of the subject, whether the subject has retinitis pigmentosa, whether the subject has developed vision loss, whether the subject has ever had a stomach ulcer, whether the subject has a bleeding disorder, a genital status of the subject, whether the subject has ever experienced priapism, whether the subject has a blood cell disorder, and whether the subject is taking a medication that interacts (e.g., a pharmacokinetic interaction and/or a pharmacodynamic interaction) with the vardenafil pharmaceutical composition.

The computer system runs survey results against a first series of filters that are each associated with a first filter category class. The first filter category class is configured to prevent authorization for OTC delivery of the OTC vardenafil when the subject's survey results identify a contraindication for the vardenafil. In some embodiments, the first series of filters includes one or more of a gender filter, an age filter, a first erectile dysfunction filter, a first vasodilator filter, a first $PDE_5$ inhibitor filter, and a first guanylate cyclase stimulator filter. The gender filter is configured to ensure the subject is male. The age filter is configured to ensure that the subject is over eighteen years old. The erectile dysfunction filter is configured to ensure the subject has erectile dysfunction. The vasodilator filter is configured to ensure the subject is not taking an organic nitrate or nitrite. The $PDE_5$ inhibitor is configured to ensure the subject is not taking additional $PDE_5$ inhibitors. Furthermore, the guanylate cyclase stimulator is configured to ensure the subject is not taking a guanylate cyclase stimulator.

The computer system runs survey results against a second series of filters that each generates a warning where the subject's survey results identify a risk factor for the OTC vardenafil. In some embodiments, the second series of filters comprises a first heart problem filter, a first blood pressure filter, a first stroke filter, a first liver disease filter, a first kidney disease filter, a first retinitis pigmentosa filter, a first stomach ulcer filter, a first bleeding problem filter, a first genital abnormality filter, a first priapism filter, a first blood cell disorder, and a first drug interaction filter. The first heart problem filter is configured to ensure the subject has not developed a heart problem. The first stroke filter is configured to ensure the subject has not had a stroke. The first liver disease filter is configured to ensure that the subject has adequate liver function. The first kidney disease filter is configured to ensure that the subject has adequate kidney function. The first retinitis pigmentosa filter is configured to ensure that the subject does not have a variety of vision conditions. The first stomach ulcer filter is configured to ensure that the subject has not had a stomach ulcer. The first bleeding problem filter is configured to ensure that the subject does not have a bleeding problem (e.g., a coagulation problem). The first genital abnormality filter is configured to ensure that the subject has a normal penile shape. The first priapism filter is configured to ensure that the subject has not experienced priapism. The first blood cell disorder filter is configured to ensure the subject has normal blood cells. The first drug interaction filter is configured to ensure the subject is not taking a substance that interacts with vardenafil. Substances that interact with vardenafil, and are therefore capable of firing the first drug interaction filter, include an alpha blocker (e.g., terazosin, tamsulosin, doxazosin mesylate, prazosin HCl, alfuzosin, dutasteride and tamsulosin HCl, and silodosin), an HIV protease inhibitor (e.g., ritonavir), an antifungal medication (e.g., ketoconazole and itraconazole), an antibiotic (e.g., clarithromycin, telithromycin, and erythromycin), a blood pressure medication (e.g., a medication to treat hypertension), and an erectile dysfunction medication.

The computer system then prompts the subject to acknowledge or deny having discussed these warnings with a medical professional (e.g., their physician or healthcare provider). The computer system then proceeds with a fulfillment process only when none of the first series of filters was fired and the subject acknowledged that they discussed each warning issued in association with the second series of filters that was fired.

The computer system stores an indication of an initial order of the OTC vardenafil in a subject profile, and communicates an over-the-counter drug facts label for the vardenafil pharmaceutical composition to the subject. Upon confirmation from the subject that they have received and read the over-the-counter drug facts label, the computer system authorizes provision of the OTC vardenafil pharmaceutical composition to the subject.

In some embodiments, the computer system includes instructions for conducting another survey of the subject responsive to a re-order request of the vardenafil pharmaceutical composition. This survey is utilized to obtain one or more results of: an erectile dysfunction status of the subject, whether the subject has started to take a nitrate or nitrite vasodilator composition since receiving their last provision of vardenafil, whether the subject has started to take a guanylate cyclase stimulator medication since receiving their last provision of vardenafil, whether the subject has started to take a $PDE_5$ inhibitor composition since receiving their last provision of vardenafil, whether the subject has developed symptoms of heart problems during sexual intercourse since receiving their last provision of vardenafil, whether the subject has experienced priapism since receiving their last provision of vardenafil, whether the subject has developed hearing or vision loss since receiving their last provision of vardenafil, whether the subject has developed a symptom of heart problems since receiving their last provision of vardenafil, a blood pressure status of the subject, whether the subject has had a stroke since receiving their last provision of vardenafil, whether the subject has developed a liver problem since receiving their last provision of vardenafil, a kidney function status of the subject, whether the subject has developed retinitis pigmentosa since receiving their last provision of vardenafil, whether the subject has developed a stomach ulcer since receiving their last provision of vardenafil, whether the subject has developed a bleeding disorder since receiving their last provision of vardenafil, whether the subject has developed an abnormal genital shape since receiving their last provision of vardenafil, whether the subject has developed a blood cell disorder since receiving their last provision of vardenafil, and whether the subject has started taking a medication that interacts with vardenafil since receiving their last provision of vardenafil.

The computer system runs survey results against a third series of filters that are each associated with the first filter category class. In some embodiments, the third series of filters includes one or more of a second erectile dysfunction filter, a second vasodilator filter, a second guanylate cyclase stimulator filter, a second $PDE_5$ inhibitor filter, a sexual intercourse filter, a second priapism filter, and a sensory deterioration filter. The second erectile dysfunction filter is configured to ensure the subject has erectile dysfunction. The second vasodilator filter is configured to ensure the subject is not taking an organic nitrate or nitrite since receiving their last provision of vardenafil. The second guanylate cyclase stimulator is configured to ensure the subject is not taking a guanylate cyclase stimulator since receiving their last provision of vardenafil. The second $PDE_5$ inhibitor is configured to ensure the subject is not taking additional $PDE_5$ inhibitors since receiving their last provision of vardenafil. The sexual intercourse filter is configured to ensure the subject has not developed heart problems during sexual intercourse since receiving their last provision of vardenafil. The second priapism filter is configured to ensure that the subject has not experienced priapism since receiving their last provision of vardenafil. The sensory deterioration filter is configured to ensure that the subject has not developed hearing loss or vision loss since receiving their last provision of vardenafil.

The computer system runs survey results against a fourth series of filters that each generates a warning where the subject's survey results identify a risk factor for the OTC vardenafil. In some embodiments, the fourth series of filters comprises a second heart problem filter, a second blood pressure filter, a second stroke filter, a second liver disease filter, a second kidney disease filter, a second retinitis pigmentosa filter, a second stomach ulcer filter, a second bleeding problem filter, a second genital abnormality filter, a second blood cell disorder, and a second drug interaction filter. The second heart problem filter is configured to ensure the subject has not developed a heart problem since receiving their last provision of vardenafil. The second stroke filter is configured to ensure the subject has not had a stroke since receiving their last provision of vardenafil. The second liver disease filter is configured to ensure that the subject has adequate liver function since receiving their last provision of vardenafil. The second kidney disease filter is configured to ensure that the subject has adequate kidney function since receiving their last provision of vardenafil. The second retinitis pigmentosa filter is configured to ensure that the subject does not have a variety of vision conditions since receiving their last provision of vardenafil. The second stomach ulcer filter is configured to ensure that the subject has not had a stomach ulcer since receiving their last provision of vardenafil. The second bleeding problem filter is configured to ensure that the subject does not have a bleeding problem (e.g., a coagulation problem) since receiving their last provision of vardenafil. The second genital abnormality filter is configured to ensure that the subject has a normal penile shape since receiving their last provision of vardenafil. The second priapism filter is configured to ensure that the subject has not experienced priapism since receiving their last provision of vardenafil. The second blood cell disorder filter is configured to ensure the subject has normal blood cells since receiving their last provision of vardenafil. The second drug interaction filter is configured to ensure the subject is not taking a substance that interacts with vardenafil since receiving their last provision of vardenafil. Substances that interact with vardenafil, and are therefore capable of firing the first drug interaction filter, include an alpha blocker (e.g., terazosin, tamsulosin, doxazosin mesylate, prazosin HCl, alfuzosin, dutasteride and tamsulosin HCl, and silodosin), an HIV protease inhibitor (e.g., ritonavir), an antifungal medication (e.g., ketoconazole and itraconazole), an antibiotic (e.g., clarithromycin, telithromycin, and erythromycin), a blood pressure medication (e.g., a medication to treat hypertension), and an erectile dysfunction medication.

The computer system then prompts the subject to acknowledge or deny having discussed these warnings with a medical professional (e.g., their physician or healthcare provider). The computer system then proceeds with a re-fulfillment process only when none of the third series of filters was fired the subject acknowledged that they discussed each warning issued in association with the fourth series of filters that was fired.

The computer system stores an indication of a re-order of the OTC vardenafil in the subject profile, and communicates the over-the-counter drug facts label for the vardenafil pharmaceutical composition to the subject. Upon confirmation from the subject that they have received and read the over-the-counter drug facts label, the computer system authorizes provision of the OTC vardenafil pharmaceutical composition to the subject.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a non-transitory computer readable storage medium. For instance, the computer program product could contain the program modules shown in any combination of FIGS. 1, 2, and 3 and/or described in FIG. 4 or 5. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A computer system for qualifying a human subject for over-the-counter delivery of a cGMP-specific phosphodiesterase 5 (PDE5) inhibitor pharmaceutical composition for treating erectile dysfunction, the computer system comprising one or more processors and a memory, the memory comprising non-transitory instructions which, when executed by the one or more processors, perform a method comprising:

a) conducting a first survey of the subject thereby obtaining a first plurality of survey results, wherein the first plurality of survey results comprises:
   a gender of the subject,
   an age of the subject,
   an erectile dysfunction status of the subject,
   whether the subject is taking a nitrate or nitrite vasodilator composition,
   whether the subject is taking a guanylate cyclase stimulator medication,
   whether the subject is taking a PDE5 inhibitor pharmaceutical composition,
   whether the subject has ever had a heart problem,
   a blood pressure status of the subject,
   whether the subject has ever had a stroke,
   whether the subject has a liver problem,
   a kidney function status of the subject, whether the subject has retinitis pigmentosa,
whether the subject has experienced vision loss,
whether the subject has ever had a stomach ulcer,
whether the subject has a bleeding disorder,
a genital status of the subject,
whether the subject has ever experienced priapism,
whether the subject has a blood cell disorder, and
whether the subject is taking a medication that interacts with the PDE5 inhibitor pharmaceutical composition;

b) running all or a portion of the first plurality of survey results against a first plurality of filters of a first category class, wherein, when a respective filter in the first plurality of filters is fired, the subject is deemed not qualified for delivery of the PDE5 inhibitor pharmaceutical composition and the method is terminated without delivery of the PDE5 inhibitor pharmaceutical composition to the subject, wherein the first plurality of filters comprises:

a gender filter that is fired when the first plurality of survey results indicates that the subject is female,
an age filter,
an first erectile dysfunction filter that is fired at least when the first plurality of survey results indicates that the subject does not have erectile dysfunction,
a first vasodilator filter that is fired at least when the first plurality of survey results indicates that the subject is taking a vasodilator composition comprising a nitrate or a nitrite,
a first PDE5 inhibitor filter that is fired at least when the first plurality of survey results indicates that the subject is taking a PDE5 inhibitor pharmaceutical composition, and
a first guanylate cyclase stimulator filter that is fired at least when the first plurality of survey results indicates that the subject is taking a guanylate cyclase stimulator mediation, and c) running all or a portion of the first plurality of survey results against a second plurality of filters of a second category class, wherein, when a respective filter in the second plurality of filters is fired, the subject is provided with a warning corresponding to the respective filter, and wherein the second plurality of filters comprises:

a first heart problem filter that is fired at least when the first plurality of survey results indicates that the subject has had a heart problem,
a first blood pressure filter that this fired at least when the first plurality of survey results indicates that the subject has either (i) low blood pressure, or (ii) uncontrolled high blood pressure,
a first stroke filter that is fired at least when the first plurality of survey results indicates that the subject has had a stroke,
a first liver disease filter that is fired at least when the first plurality of survey results indicates that the subject has a liver problem,
a first kidney disease filter that is fired at least when the first plurality of survey results indicates that the subject has a kidney problem, and
a first retinitis pigmentosa filter that is fired at least when the first plurality of survey results indicates that the subject has retinitis pigmentosa,
a first vision deterioration filter that is fired at least when the first plurality of survey results indicates that the subject has had severe vision loss,
a first stomach ulcer filter that is fired at least when the first plurality of survey results indicates that the subject has had a stomach ulcer,
a first bleeding problem filter that is fired at least when the first plurality of survey results indicates that the subject has a bleeding disorder,
a first genital abnormality filter that is fired at least when the first plurality of survey results indicates that the subject has an abnormal penile shape,
a first priapism filter that is fired at least when the first plurality of survey results indicates that the subject has experienced priapism,
a first blood cell disorder filter that is fired at least when the first plurality of survey results indicates that the subject has a blood cell disorder selected from the group consisting of sickle cell anemia, multiple myeloma, and leukemia, and
a first drug interaction filter that is fired at least when the first plurality of survey results indicates that the subject is taking a medication that interacts with the PDE5 inhibitor pharmaceutical composition;

d) obtaining acknowledgment from the subject for the warning issued to the subject by any filter in the second plurality of filters; and e) proceeding with a fulfillment process when (i) no filter in the first plurality of filters has been fired and (ii) the subject has acknowledged each warning associated with each filter in the second plurality of filters that was fired, wherein the fulfillment process comprises:

storing an indication in a subject profile of an initial order for the PDE5 inhibitor pharmaceutical composition,
communicating an over-the-counter facts label for the PDE5 inhibitor pharmaceutical composition to the subject, and
authorizing, upon confirmation from the subject that the over-the-counter drug facts label has been received and read, provision of the PDE5 inhibitor pharmaceutical composition to the subject,
wherein the PDE5 inhibitor pharmaceutical composition is administered to the subject after provision of the PDE5 inhibitor pharmaceutical composition has been authorized for the subject.

2. The computer system of claim 1, wherein the PDE5 inhibitor pharmaceutical composition has the structure:

wherein:
$R^0$ represents hydrogen, halogen or $C_{1-6}$ alkyl;
$R^1$ represents hydrogen, $C_{1-6}$ alkyl, $C_{2-6}$ alkenyl, $C_{2-6}$ alkynyl, halo$C_{1-6}$ alkyl, $C_{3-8}$ cycloalkyl, $C_{3-8}$ cycloalkyl-$C_{1-3}$ alkyl, aryl$C_{1-3}$ alkyl or heteroaryl$C_{1-3}$ alkyl;
$R^2$ represents an optionally substituted mono-cyclic aromatic ring selected from benzene, thiophene, furan and pyridine or an optionally substituted bicyclic ring

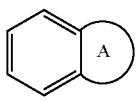

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and $R^3$ represents hydrogen or C1-3 alkyl, or $R^1$ and $R^3$ together represent a 3- or 4-membered alkyl or alkenyl chain, or a pharmaceutically acceptable salt thereof.

3. The computer system of claim 1, wherein the PDE5 inhibitor pharmaceutical composition is tadalafil or a pharmaceutically acceptable salt thereof.

4. The computer system of claim 3, wherein, upon confirmation from the subject that the over-the-counter drug facts label has been received and read, the subject is authorized for provision of a dosage of from 2.5 mg to 10 mg of tadalafil no more than once per day.

5. The computer system of claim 3, wherein, upon confirmation from the subject that the over-the-counter drug facts label has been received and read, the subject is authorized for provision of a dosage of 5 mg of tadalafil no more than once per day.

6. The computer system of claim 1, wherein the PDE5 inhibitor pharmaceutical composition is vardenafil.

7. The computer system of claim 1, wherein the age filter is fired when the first plurality of survey results indicates that the subject is less than eighteen years old.

8. The computer system of claim 1, wherein the vasodilator composition, which is capable of firing the first vasodilator filter, includes a compound selected from the group consisting of nitroglycerin, amyl nitrate, amyl nitrite, and butyl nitrate.

9. The computer system of claim 1, wherein the heart problem, which is capable of firing the first heart problem filter, is selected from the group consisting of a heart attack, arrhythmia, angina, chest pain, narrowing of the aortic valve, and heart failure.

10. The computer system of claim 1, wherein the first drug interaction filter is fired when the first plurality of survey results indicates that the subject is taking a medication selected from the group consisting of an alpha blocker, an HIV protease inhibitor, an antifungal medication, an antibiotic, a blood pressure medication, and an erectile dysfunction medication.

11. The computer system of claim 1, wherein:
the warning corresponding to a respective filter in the second plurality of filters comprises a prompt for the subject to indicate whether they have discussed the risk factor underlying the respective filter in the second plurality of filters that was fired with a health care provider; and
acknowledgement is obtained from the subject when the subject indicates that they have discussed the risk factor underlying the respective filter in the second plurality of filters that was fired with a health care provider.

12. The computer system of claim 1, wherein the fulfillment process further comprises:
storing a destination associated with the subject in the subject profile.

13. The computer system of claim 1, wherein the fulfillment process further comprises:
coordinating shipping of the PDE5 inhibitor pharmaceutical composition to a physical address associated with the subject.

14. The computer system of claim 1, wherein the method further comprises:
f) responsive to receiving a re-order request from the subject for the PDE5 inhibitor pharmaceutical composition, performing a re-fulfillment procedure comprising:
(i) conducting a second survey of the subject thereby obtaining a second plurality of survey results, wherein the second plurality of survey results comprises:
an erectile dysfunction status of the subject,
whether the subject has started to take a nitrate or nitrite vasodilator composition since receiving their last provision of the PDE5 inhibitor pharmaceutical composition,
whether the subject has started to take a guanylate cyclase stimulator medication since receiving their last provision of the PDE5 inhibitor pharmaceutical composition,
whether the subject has started to take a PDE5 inhibitor pharmaceutical composition since receiving their last provision of the PDE5 inhibitor pharmaceutical composition,
whether the subject has experienced a symptom of heart problems during sexual intercourse since receiving their last provision of the PDE5 inhibitor pharmaceutical composition,
whether the subject has experienced priapism since receiving their last provision of the PDE5 inhibitor pharmaceutical composition,
whether the subject has experienced hearing or vision loss since receiving their last provision of the PDE5 inhibitor pharmaceutical composition,
whether the subject has developed a symptom of heart problems since receiving their last provision of the PDE5 inhibitor pharmaceutical composition,
a blood pressure status of the subject,
whether the subject has had a stroke since receiving their last provision of the PDE5 inhibitor pharmaceutical composition,
whether the subject has developed a liver problem since receiving their last provision of the PDE5 inhibitor pharmaceutical composition,
a kidney function status of the subject,
whether the subject has developed retinitis pigmentosa since receiving their last provision of the PDE5 inhibitor pharmaceutical composition,
whether the subject has developed a stomach ulcer since receiving their last provision of the PDE5 inhibitor pharmaceutical composition,
whether the subject has developed a bleeding disorder since receiving their last provision of the PDE5 inhibitor pharmaceutical composition,
whether the subject has developed an abnormal genital shape since receiving their last provision of the PDE5 inhibitor pharmaceutical composition,
whether the subject has developed a blood cell disorder since receiving their last provision of the PDE5 inhibitor pharmaceutical composition, and
whether the subject has starting taking a medication that interacts with the PDE5 inhibitor pharmaceutical composition since receiving their last provision of the PDE5 inhibitor pharmaceutical composition;
(ii) running all or a portion of the second plurality of survey results against a third plurality of filters of the first category class, wherein, when a respective filter in the third plurality of filters is fired, the subject is deemed not qualified for the PDE5 inhibitor pharmaceutical composition and the re-fulfillment process is terminated without delivery of the PDE5 inhibitor pharmaceutical composition to the subject, wherein the third plurality of filters comprises:
a second erectile dysfunction filter that is fired at least when the second plurality of survey results indicates that the subject does not have erectile dysfunction,
a second vasodilator filter that is fired at least when the second plurality of survey results indicates that the subject is taking a vasodilator composition comprising a nitrate or a nitrite,
a second guanylate cyclase stimulator filter that is fired at least when the second plurality of survey results indicates that the subject is taking a guanylate cyclase stimulator mediation,
a second PDE5 inhibitor filter that is fired at least when the second plurality of survey results indicates that the subject is taking a PDE5 inhibitor pharmaceutical composition,
a sexual intercourse filter that is fired at least when the second plurality of survey results indicates that the subject has experienced a symptom of heart problems during sexual intercourse since receiving their last provision of the PDE5 inhibitor pharmaceutical composition,
a second priapism filter that is fired at least when the second plurality of survey results indicates that the subject has had priapism since receiving their last provision of the PDE5 inhibitor pharmaceutical composition, and
a sensory deterioration filter that is fired at least when the second plurality of survey results indicates that the subject has experienced a sudden vision loss or sudden hearing loss since receiving their last provision of the PDE5 inhibitor pharmaceutical composition;
(iii) running all or a portion of the second plurality of survey results against a fourth plurality of filters of the second category class, wherein, when a respective filter in the fourth plurality of filters is fired, the subject is provided with a warning corresponding to the respective filter, and wherein the fourth plurality of filters comprises:
a second heart problem filter that is fired at least when the second plurality of survey results indicates that the subject has developed a heart problem since receiving their last provision of the PDE5 inhibitor pharmaceutical composition,
a second blood pressure filter that this fired at least when the second plurality of survey results indicates that the subject has developed either (i) low blood pressure, or (ii) uncontrolled high blood pressure,
a second stroke filter that is fired at least when the second plurality of survey results indicates that the subject has had a stroke since receiving their last provision of the PDE5 inhibitor pharmaceutical composition,
a second liver disease filter that is fired at least when the second plurality of survey results indicates that the subject has developed liver disease since receiving their last provision of the PDE5 inhibitor pharmaceutical composition,
a second kidney disease filter that is fired at least when the second plurality of survey results indicates that the subject has developed a kidney problem since receiving their last provision of the PDE5 inhibitor pharmaceutical composition,
a second retinitis pigmentosa filter that is fired at least when the second plurality of survey results indicates that the subject has been diagnosed with retinitis pigmentosa since receiving their last provision of the PDE5 inhibitor pharmaceutical composition,
a second stomach ulcer filter that is fired at least when the second plurality of survey results indicates that the subject has developed a stomach ulcer since receiving their last provision of the PDE5 inhibitor pharmaceutical composition,
a second bleeding problem filter that is fired at least when the second plurality of survey results indicates that the subject has developed a bleeding disorder since receiving their last provision of the PDE5 inhibitor pharmaceutical composition,
a second genital abnormality filter that is fired at least when the second plurality of survey results indicates that the subject has developed an abnormal genital shape since receiving their last provision of the PDE5 inhibitor pharmaceutical composition,
a second blood cell disorder filter that is fired at least when the second plurality of survey results indicates that the subject has developed a blood disorder selected from the group consisting of sickle cell anemia, multiple myeloma, and leukemia, since receiving their last provision of the PDE5 inhibitor pharmaceutical composition, and
a second drug interaction filter that is fired at least when the second plurality of survey results indicates that the subject has started taking a medication that interacts with the PDE5 inhibitor pharmaceutical composition since receiving their last provision of the PDE5 inhibitor pharmaceutical composition;
(iv) obtaining acknowledgment from the subject for the warning issued to the subject by any filter in the fourth plurality of filters; and
(v) proceeding with the re-fulfillment process when (a) the re-fulfillment process is not already terminated by the firing of a filter in the third plurality of filters and (b) the subject has acknowledged each warning associated with each filter in the fourth plurality of filters that was fired, wherein the re-fulfillment process further comprises:
storing an indication in a subject profile of a re-order for the PDE5 inhibitor pharmaceutical composition,
communicating the over-the-counter drug facts label for the PDE5 inhibitor pharmaceutical composition to the subject, and
authorizing, upon confirmation from the subject that the over-the-counter drug facts label has been received and read, a re-order provision of the PDE5 inhibitor pharmaceutical composition to the subject.

15. The computer system of claim 14, wherein:
the second plurality of survey results further comprises whether the subject has experienced a side effect associated with the PDE5 inhibitor pharmaceutical composition since receiving their last provision of the PDE5 inhibitor pharmaceutical composition, and
the fourth plurality of filters further comprises a side effect filter that is fired at least when the second plurality of survey results indicates that the subject has experienced, since receiving their last provision of the PDE5 inhibitor pharmaceutical composition, a side effect selected from the group consisting of headaches, abnormal vision, muscle pain, nausea, dizziness, and a skin rash.

16. The computer system of claim 14, wherein the re-fulfillment process further comprises, when a respective filter in the third plurality of filters or fourth plurality of filters is fired, storing a record associated with the firing of the respective filter in an adverse event profile comprising records of filter firing events associated with a plurality of subjects.

17. A method for qualifying a human subject for over-the-counter delivery of a cGMP-specific phosphodiesterase 5 (PDE5) inhibitor pharmaceutical composition for treating erectile dysfunction, the method comprising:
a) conducting a first survey of the subject thereby obtaining a first plurality of survey results, wherein the first plurality of survey results comprises:
a gender of the subject,
an age of the subject,
an erectile dysfunction status of the subject,
whether the subject is taking a nitrate or nitrite vasodilator composition,
whether the subject is taking a guanylate cyclase stimulator medication,
whether the subject is taking a PDE5 inhibitor pharmaceutical composition,
whether the subject has ever had a heart problem,
a blood pressure status of the subject,
whether the subject has ever had a stroke,
whether the subject has a liver problem,
a kidney function status of the subject,
whether the subject has retinitis pigmentosa,
whether the subject has experienced vision loss,
whether the subject has ever had a stomach ulcer,
whether the subject has a bleeding disorder,
a genital status of the subject,
whether the subject has ever experienced priapism,
whether the subject has a blood cell disorder, and
whether the subject is taking a medication that interacts with the PDE5 inhibitor pharmaceutical composition;
b) running all or a portion of the first plurality of survey results against a first plurality of filters of a first category class, wherein, when a respective filter in the first plurality of filters is fired, the subject is deemed not qualified for delivery of the PDE5 inhibitor pharmaceutical composition and the method is terminated without delivery of the PDE5 inhibitor pharmaceutical composition to the subject, wherein the first plurality of filters comprises:
a gender filter that is fired when the first plurality of survey results indicates that the subject is female,
an age filter,
an first erectile dysfunction filter that is fired at least when the first plurality of survey results indicates that the subject does not have erectile dysfunction,
a first vasodilator filter that is fired at least when the first plurality of survey results indicates that the subject is taking a vasodilator composition comprising a nitrate or a nitrite,
a first PDE5 inhibitor filter that is fired at least when the first plurality of survey results indicates that the subject is taking a PDE5 inhibitor pharmaceutical composition, and
a first guanylate cyclase stimulator filter that is fired at least when the first plurality of survey results indicates that the subject is taking a guanylate cyclase stimulator mediation, and
c) running all or a portion of the first plurality of survey results against a second plurality of filters of a second category class, wherein, when a respective filter in the second plurality of filters is fired, the subject is provided with a warning corresponding to the respective filter, and wherein the second plurality of filters comprises:
a first heart problem filter that is fired at least when the first plurality of survey results indicates that the subject has had a heart problem,
a first blood pressure filter that this fired at least when the first plurality of survey results indicates that the subject has either (i) low blood pressure, or (ii) uncontrolled high blood pressure,
a first stroke filter that is fired at least when the first plurality of survey results indicates that the subject has had a stroke,
a first liver disease filter that is fired at least when the first plurality of survey results indicates that the subject has a liver problem,
a first kidney disease filter that is fired at least when the first plurality of survey results indicates that the subject has a kidney problem, and
a first retinitis pigmentosa filter that is fired at least when the first plurality of survey results indicates that the subject has retinitis pigmentosa,
a first vision deterioration filter that is fired at least when the first plurality of survey results indicates that the subject has had severe vision loss,
a first stomach ulcer filter that is fired at least when the first plurality of survey results indicates that the subject has had a stomach ulcer,
a first bleeding problem filter that is fired at least when the first plurality of survey results indicates that the subject has a bleeding disorder,
a first genital abnormality filter that is fired at least when the first plurality of survey results indicates that the subject has an abnormal penile shape,
a first priapism filter that is fired at least when the first plurality of survey results indicates that the subject has experienced priapism,
a first blood cell disorder filter that is fired at least when the first plurality of survey results indicates that the subject has a blood cell disorder selected from the group consisting of sickle cell anemia, multiple myeloma, and leukemia, and
a first drug interaction filter that is fired at least when the first plurality of survey results indicates that the subject is taking a medication that interacts with the PDE5 inhibitor pharmaceutical composition;
d) obtaining acknowledgment from the subject for the warning issued to the subject by any filter in the second plurality of filters; and
e) proceeding with a fulfillment process when (i) no filter in the first plurality of filters has been fired and (ii) the subject has acknowledged each warning associated with each filter in the second plurality of filters that was fired, wherein the fulfillment process comprises:
storing an indication in a subject profile of an initial order for the PDE5 inhibitor pharmaceutical composition,
communicating an over-the-counter facts label for the PDE5 inhibitor pharmaceutical composition to the subject, and
authorizing, upon confirmation from the subject that the over-the-counter drug facts label has been received and read, provision of the PDE5 inhibitor pharmaceutical composition to the subject,
wherein the PDE5 inhibitor pharmaceutical composition is administered to the subject after provision of the PDE5 inhibitor pharmaceutical composition has been authorized for the subject.

18. The method of claim 17, wherein the PDE5 inhibitor pharmaceutical composition has the structure:

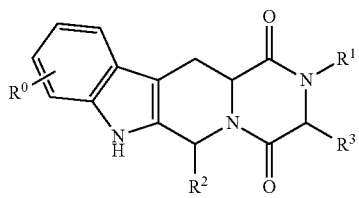

wherein:
$R^0$ represents hydrogen, halogen or $C_{1-6}$ alkyl;
$R^1$ represents hydrogen, $C_{1-6}$ alkyl, $C_{2-6}$ alkenyl, $C_{2-6}$ alkynyl, halo$C_{1-6}$ alkyl, $C_{3-8}$ cycloalkyl, $C_{3-8}$ cycloalkyl-$C_{1-3}$ alkyl, aryl$C_{1-3}$ alkyl or heteroaryl$C_{1-3}$ alkyl;
$R^2$ represents an optionally substituted mono-cyclic aromatic ring selected from benzene, thiophene, furan and pyridine or an optionally substituted bicyclic ring

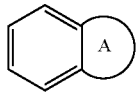

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and
$R^3$ represents hydrogen or C1-3 alkyl, or $R^1$ and $R^3$ together represent a 3- or 4-membered alkyl or alkenyl chain,
or a pharmaceutically acceptable salt thereof.

19. The method of claim 17, wherein the PDE5 inhibitor pharmaceutical composition is tadalafil or a pharmaceutically acceptable salt thereof.

20. The method of claim 19, wherein, upon confirmation from the subject that the over-the-counter drug facts label has been received and read, the subject is authorized for provision of a dosage of from 2.5 mg to 10 mg of tadalafil no more than once per day.

21. The method of claim 19, wherein, upon confirmation from the subject that the over-the-counter drug facts label has been received and read, the subject is authorized for provision of a dosage of 5 mg of tadalafil no more than once per day.

22. The method of claim 17, wherein the PDE5 inhibitor pharmaceutical composition is vardenafil.

23. The method of claim 17, wherein the age filter is fired when the first plurality of survey results indicates that the subject is less than eighteen years old.

24. The method of claim 17, wherein the vasodilator composition, which is capable of firing the first vasodilator filter, includes a compound selected from the group consisting of nitroglycerin, amyl nitrate, amyl nitrite, and butyl nitrate.

25. The method of claim 17, wherein the heart problem, which is capable of firing the first heart problem filter, is selected from the group consisting of a heart attack, arrhythmia, angina, chest pain, narrowing of the aortic valve, and heart failure.

26. The method of claim 17, wherein the first drug interaction filter is fired when the first plurality of survey results indicates that the subject is taking a medication selected from the group consisting of an alpha blocker, an HIV protease inhibitor, an antifungal medication, an antibiotic, a blood pressure medication, and an erectile dysfunction medication.

27. The method of claim 17, wherein:
the warning corresponding to a respective filter in the second plurality of filters comprises a prompt for the subject to indicate whether they have discussed the risk factor underlying the respective filter in the second plurality of filters that was fired with a health care provider; and
acknowledgement is obtained from the subject when the subject indicates that they have discussed the risk factor underlying the respective filter in the second plurality of filters that was fired with a health care provider.

28. The method of claim 17, wherein the fulfillment process further comprises:
storing a destination associated with the subject in the subject profile.

29. The method of claim 17, wherein the fulfillment process further comprises:
coordinating shipping of the PDE5 inhibitor pharmaceutical composition to a physical address associated with the subject.

30. The method of claim 17, wherein the method further comprises:
f) responsive to receiving a re-order request from the subject for the PDE5 inhibitor pharmaceutical composition, performing a re-fulfillment procedure comprising:
(i) conducting a second survey of the subject thereby obtaining a second plurality of survey results, wherein the second plurality of survey results comprises:
an erectile dysfunction status of the subject,
whether the subject has started to take a nitrate or nitrite vasodilator composition since receiving their last provision of the PDE5 inhibitor pharmaceutical composition,
whether the subject has started to take a guanylate cyclase stimulator medication since receiving their last provision of the PDE5 inhibitor pharmaceutical composition,
whether the subject has started to take a PDE5 inhibitor pharmaceutical composition since receiving their last provision of the PDE5 inhibitor pharmaceutical composition,
whether the subject has experienced a symptom of heart problems during sexual intercourse since receiving their last provision of the PDE5 inhibitor pharmaceutical composition,
whether the subject has experienced priapism since receiving their last provision of the PDE5 inhibitor pharmaceutical composition,
whether the subject has experienced hearing or vision loss since receiving their last provision of the PDE5 inhibitor pharmaceutical composition,
whether the subject has developed a symptom of heart problems since receiving their last provision of the PDE5 inhibitor pharmaceutical composition,
a blood pressure status of the subject,
whether the subject has had a stroke since receiving their last provision of PDE5 inhibitor pharmaceutical composition,
whether the subject has developed a liver problem since receiving their last provision of the PDE5 inhibitor pharmaceutical composition,
a kidney function status of the subject,
whether the subject has developed retinitis pigmentosa since receiving their last provision of the PDE5 inhibitor pharmaceutical composition,
whether the subject has developed a stomach ulcer since receiving their last provision of the PDE5 inhibitor pharmaceutical composition,
whether the subject has developed a bleeding disorder since receiving their last provision of the PDE5 inhibitor pharmaceutical composition,
whether the subject has developed an abnormal genital shape since receiving their last provision of the PDE5 inhibitor pharmaceutical composition,
whether the subject has developed a blood cell disorder since receiving their last provision of the PDE5 inhibitor pharmaceutical composition, and
whether the subject has starting taking a medication that interacts with the PDE5 inhibitor pharmaceutical composition since receiving their last provision of the PDE5 inhibitor pharmaceutical composition;

(ii) running all or a portion of the second plurality of survey results against a third plurality of filters of the first category class, wherein, when a respective filter in the third plurality of filters is fired, the subject is deemed not qualified for the PDE5 inhibitor pharmaceutical composition and the re-fulfillment process is terminated without delivery of the PDE5 inhibitor pharmaceutical composition to the subject, wherein the third plurality of filters comprises:
a second erectile dysfunction filter that is fired at least when the second plurality of survey results indicates that the subject does not have erectile dysfunction,
a second vasodilator filter that is fired at least when the second plurality of survey results indicates that the subject is taking a vasodilator composition comprising a nitrate or a nitrite,
a second guanylate cyclase stimulator filter that is fired at least when the second plurality of survey results indicates that the subject is taking a guanylate cyclase stimulator mediation,
a second PDE5 inhibitor filter that is fired at least when the second plurality of survey results indicates that the subject is taking a PDE5 inhibitor pharmaceutical composition,
a sexual intercourse filter that is fired at least when the second plurality of survey results indicates that the subject has experienced a symptom of heart problems during sexual intercourse since receiving their last provision of the PDE5 inhibitor pharmaceutical composition,
a second priapism filter that is fired at least when the second plurality of survey results indicates that the subject has had priapism since receiving their last provision of the PDE5 inhibitor pharmaceutical composition, and
a sensory deterioration filter that is fired at least when the second plurality of survey results indicates that the subject has experienced a sudden vision loss or sudden hearing loss since receiving their last provision of PDE5 inhibitor pharmaceutical composition;

(iii) running all or a portion of the second plurality of survey results against a fourth plurality of filters of the second category class, wherein, when a respective filter in the fourth plurality of filters is fired, the subject is provided with a warning corresponding to the respective filter, and wherein the fourth plurality of filters comprises:
a second heart problem filter that is fired at least when the second plurality of survey results indicates that the subject has developed a heart problem since receiving their last provision of the PDE5 inhibitor pharmaceutical composition,
a second blood pressure filter that this fired at least when the second plurality of survey results indicates that the subject has developed either (i) low blood pressure, or (ii) uncontrolled high blood pressure,
a second stroke filter that is fired at least when the second plurality of survey results indicates that the subject has had a stroke since receiving their last provision of the PDE5 inhibitor pharmaceutical composition,
a second liver disease filter that is fired at least when the second plurality of survey results indicates that the subject has developed liver disease since receiving their last provision of the PDE5 inhibitor pharmaceutical composition,
a second kidney disease filter that is fired at least when the second plurality of survey results indicates that the subject has developed a kidney problem since receiving their last provision of the PDE5 inhibitor pharmaceutical composition,
a second retinitis pigmentosa filter that is fired at least when the second plurality of survey results indicates that the subject has been diagnosed with retinitis pigmentosa since receiving their last provision of the PDE5 inhibitor pharmaceutical composition,
a second stomach ulcer filter that is fired at least when the second plurality of survey results indicates that the subject has developed a stomach ulcer since receiving their last provision of the PDE5 inhibitor pharmaceutical composition,
a second bleeding problem filter that is fired at least when the second plurality of survey results indicates that the subject has developed a bleeding disorder since receiving their last provision of the PDE5 inhibitor pharmaceutical composition,
a second genital abnormality filter that is fired at least when the second plurality of survey results indicates that the subject has developed an abnormal genital shape since receiving their last provision of the PDE5 inhibitor pharmaceutical composition, a second blood cell disorder filter that is fired at least when the second plurality of survey results indicates that the subject has developed a blood disorder selected from the group consisting of sickle cell anemia, multiple myeloma, and leukemia, since receiving their last provision of the PDE5 inhibitor pharmaceutical composition, and a second drug interaction filter that is fired at least when the second plurality of survey results indicates that the subject has started taking a medication that interacts with the PDE5 inhibitor pharmaceutical composition since receiving their last provision of the PDE5 inhibitor pharmaceutical composition;

(iv) obtaining acknowledgment from the subject for the warning issued to the subject by any filter in the fourth plurality of filters; and (v) proceeding with the re-fulfillment process when (a) the re-fulfillment process is not already terminated by the firing of a filter in the third plurality of filters and (b) the subject has acknowledged each warning associated with each filter in the fourth plurality of filters that was fired, wherein the re-fulfillment process further comprises:

storing an indication in a subject profile of a re-order for the PDE5 inhibitor pharmaceutical composition, communicating the over-the-counter drug facts label for PDE5 inhibitor pharmaceutical composition to the subject, and authorizing, upon confirmation from the subject that the over-the-counter drug facts label has been received and read, a re-order provision of the PDE5 inhibitor pharmaceutical composition to the subject.

31. The method of claim 30, wherein:
the second plurality of survey results further comprises whether the subject has experienced a side effect associated with the PDE5 inhibitor pharmaceutical composition since receiving their last provision of the PDE5 inhibitor pharmaceutical composition, and the fourth plurality of filters further comprises a side effect filter that is fired at least when the second plurality of survey results indicates that the subject has experienced, since receiving their last provision of the PDE5 inhibitor pharmaceutical composition, a side effect selected from the group consisting of headaches, abnormal vision, muscle pain, nausea, dizziness, and a skin rash.

32. The method of claim 30, wherein the re-fulfillment process further comprises, when a respective filter in the third plurality of filters or fourth plurality of filters is fired, storing a record associated with the firing of the respective filter in an adverse event profile comprising records of filter firing events associated with a plurality of subjects.

33. A non-transitory computer readable storage medium storing one or more programs, the one or more programs comprising instructions, which when executed by an electronic device with one or more processors and a memory cause the electronic device to perform a method for qualifying a human subject for over-the-counter delivery of a cGMP-specific phosphodiesterase 5 (PDE5) inhibitor pharmaceutical composition for treating erectile dysfunction, the method comprising:

a) conducting a first survey of the subject thereby obtaining a first plurality of survey results, wherein the first plurality of survey results comprises:
a gender of the subject,
an age of the subject,
an erectile dysfunction status of the subject,
whether the subject is taking a nitrate or nitrite vasodilator composition,
whether the subject is taking a guanylate cyclase stimulator medication,
whether the subject is taking a PDE5 inhibitor pharmaceutical composition,
whether the subject has ever had a heart problem,
a blood pressure status of the subject,
whether the subject has ever had a stroke,
whether the subject has a liver problem,
a kidney function status of the subject,
whether the subject has retinitis pigmentosa,
whether the subject has experienced vision loss,
whether the subject has ever had a stomach ulcer,
whether the subject has a bleeding disorder,
a genital status of the subject,
whether the subject has ever experienced priapism,
whether the subject has a blood cell disorder, and
whether the subject is taking a medication that interacts with the PDE5 inhibitor pharmaceutical composition;

b) running all or a portion of the first plurality of survey results against a first plurality of filters of a first category class, wherein, when a respective filter in the first plurality of filters is fired, the subject is deemed not qualified for delivery of the PDE5 inhibitor pharmaceutical composition and the method is terminated without delivery of the PDE5 inhibitor pharmaceutical composition to the subject, wherein the first plurality of filters comprises:
a gender filter that is fired when the first plurality of survey results indicates that the subject is female,
an age filter,
an first erectile dysfunction filter that is fired at least when the first plurality of survey results indicates that the subject does not have erectile dysfunction,
a first vasodilator filter that is fired at least when the first plurality of survey results indicates that the subject is taking a vasodilator composition comprising a nitrate or a nitrite,
a first PDE5 inhibitor filter that is fired at least when the first plurality of survey results indicates that the subject is taking a PDE5 inhibitor pharmaceutical composition, and
a first guanylate cyclase stimulator filter that is fired at least when the first plurality of survey results indicates that the subject is taking a guanylate cyclase stimulator mediation, and c) running all or a portion of the first plurality of survey results against a second plurality of filters of a second category class, wherein, when a respective filter in the second plurality of filters is fired, the subject is provided with a warning corresponding to the respective filter, and wherein the second plurality of filters comprises:
a first heart problem filter that is fired at least when the first plurality of survey results indicates that the subject has had a heart problem,
a first blood pressure filter that this fired at least when the first plurality of survey results indicates that the subject has either (i) low blood pressure, or (ii) uncontrolled high blood pressure, a first stroke filter that is fired at least when the first plurality of survey results indicates that the subject has had a stroke, a first liver disease filter that is fired at least when the first plurality of survey results indicates that the subject has a liver problem, a first kidney disease filter that is fired at least when the first plurality of survey results indicates that the subject has a kidney problem, and a first retinitis pigmentosa filter that is fired at least when the first plurality of survey results indicates that the subject has retinitis pigmentosa, a first vision deterioration filter that is fired at least when the first plurality of survey results indicates that the subject has had severe vision loss, a first stomach ulcer filter that is fired at least when the first plurality of survey results indicates that the subject has had a stomach ulcer, a first bleeding problem filter that is fired at least when the first plurality of survey results indicates that the subject has a bleeding disorder, a first genital abnormality filter that is fired at least when the first plurality of survey results indicates that the subject has an abnormal penile shape, a first priapism filter that is fired at least when the first plurality of survey results indicates that the subject has experienced priapism, a first blood cell disorder filter that is fired at least when the first plurality of survey results indicates that the subject has a blood cell disorder selected from the group consisting of sickle cell anemia, multiple myeloma, and leukemia, and a first drug interaction filter that is fired at least when the first plurality of survey results indicates that the subject is taking a medication that interacts with the PDE5 inhibitor pharmaceutical composition;

d) obtaining acknowledgment from the subject for the warning issued to the subject by any filter in the second plurality of filters; and e) proceeding with a fulfillment process when (i) no filter in the first plurality of filters has been fired and (ii) the subject has acknowledged each warning associated with each filter in the second plurality of filters that was fired, wherein the fulfillment process comprises:

storing an indication in a subject profile of an initial order for the PDE5 inhibitor pharmaceutical composition, communicating an over-the-counter facts label for the PDE5 inhibitor pharmaceutical composition to the subject, and authorizing, upon confirmation from the subject that the over-the-counter drug facts label has been received and read, provision of the PDE5 inhibitor pharmaceutical composition to the subject, wherein the PDE5 inhibitor pharmaceutical composition is administered to the subject after provision of the PDE5 inhibitor pharmaceutical composition has been authorized for the subject.

34. The non-transitory computer readable storage medium of claim 33, wherein the PDE5 inhibitor pharmaceutical composition has the structure:

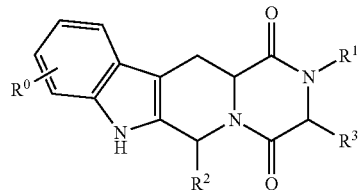

wherein:

$R^0$ represents hydrogen, halogen or $C_{1-6}$ alkyl;

$R^1$ represents hydrogen, $C_{1-6}$ alkyl, $C_{2-6}$ alkenyl, $C_{2-6}$ alkynyl, halo$C_{1-6}$ alkyl, $C_{3-8}$ cycloalkyl, $C_{3-8}$ cycloalkyl-$C_{1-3}$ alkyl, aryl$C_{1-3}$ alkyl or heteroaryl$C_{1-3}$ alkyl;

$R^2$ represents an optionally substituted mono-cyclic aromatic ring selected from benzene, thiophene, furan and pyridine or an optionally substituted bicyclic ring

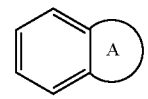

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and $R^3$ represents hydrogen or C1-3 alkyl, or $R^1$ and $R^3$ together represent a 3- or 4-membered alkyl or alkenyl chain, or a pharmaceutically acceptable salt thereof.

35. The non-transitory computer readable storage medium of claim 33, wherein the PDE5 inhibitor pharmaceutical composition is tadalafil or a pharmaceutically acceptable salt thereof.

36. The non-transitory computer readable storage medium of claim 35, wherein, upon confirmation from the subject that the over-the-counter drug facts label has been received and read, the subject is authorized for provision of a dosage of from 2.5 mg to 10 mg of tadalafil no more than once per day.

37. The non-transitory computer readable storage medium of claim 35, wherein, upon confirmation from the subject that the over-the-counter drug facts label has been received and read, the subject is authorized for provision of a dosage of 5 mg of tadalafil no more than once per day.

38. The non-transitory computer readable storage medium of claim 33, wherein the PDE5 inhibitor pharmaceutical composition is vardenafil.

39. The non-transitory computer readable storage medium of claim 33, wherein the age filter is fired when the first plurality of survey results indicates that the subject is less than eighteen years old.

40. The non-transitory computer readable storage medium of claim 33, wherein the vasodilator composition, which is capable of firing the first vasodilator filter, includes a compound selected from the group consisting of nitroglycerin, amyl nitrate, amyl nitrite, and butyl nitrate.

41. The non-transitory computer readable storage medium of claim 33, wherein the heart problem, which is capable of firing the first heart problem filter, is selected from the group consisting of a heart attack, arrhythmia, angina, chest pain, narrowing of the aortic valve, and heart failure.

42. The non-transitory computer readable storage medium of claim 33, wherein the first drug interaction filter is fired when the first plurality of survey results indicates that the subject is taking a medication selected from the group consisting of an alpha blocker, an HIV protease inhibitor, an antifungal medication, an antibiotic, a blood pressure medication, and an erectile dysfunction medication.

43. The non-transitory computer readable storage medium of claim 33, wherein:
the warning corresponding to a respective filter in the second plurality of filters comprises a prompt for the subject to indicate whether they have discussed the risk factor underlying the respective filter in the second plurality of filters that was fired with a health care provider; and
acknowledgement is obtained from the subject when the subject indicates that they have discussed the risk factor underlying the respective filter in the second plurality of filters that was fired with a health care provider.

44. The non-transitory computer readable storage medium of claim 33, wherein the fulfillment process further comprises:
storing a destination associated with the subject in the subject profile.

45. The non-transitory computer readable storage medium of claim 33, wherein the fulfillment process further comprises:
coordinating shipping of the PDE5 inhibitor pharmaceutical composition to a physical address associated with the subject.

46. The non-transitory computer readable storage medium of claim 33, wherein the method further comprises:
f) responsive to receiving a re-order request from the subject for the PDE5 inhibitor pharmaceutical composition, performing a re-fulfillment procedure comprising:
(i) conducting a second survey of the subject thereby obtaining a second plurality of survey results, wherein the second plurality of survey results comprises:
an erectile dysfunction status of the subject,
whether the subject has started to take a nitrate or nitrite vasodilator composition since receiving their last provision of the PDE5 inhibitor pharmaceutical composition,
whether the subject has started to take a guanylate cyclase stimulator medication since receiving their last provision of the PDE5 inhibitor pharmaceutical composition,
whether the subject has started to take a PDE5 inhibitor pharmaceutical composition since receiving their last provision of the PDE5 inhibitor pharmaceutical composition,
whether the subject has experienced a symptom of heart problems during sexual intercourse since receiving their last provision of the PDE5 inhibitor pharmaceutical composition,
whether the subject has experienced priapism since receiving their last provision of the PDE5 inhibitor pharmaceutical composition,
whether the subject has experienced hearing or vision loss since receiving their last provision of the PDE5 inhibitor pharmaceutical composition,
whether the subject has developed a symptom of heart problems since receiving their last provision of the PDE5 inhibitor pharmaceutical composition,
a blood pressure status of the subject,
whether the subject has had a stroke since receiving their last provision of PDE5 inhibitor pharmaceutical composition,
whether the subject has developed a liver problem since receiving their last provision of the PDE5 inhibitor pharmaceutical composition,
a kidney function status of the subject,
whether the subject has developed retinitis pigmentosa since receiving their last provision of the PDE5 inhibitor pharmaceutical composition,
whether the subject has developed a stomach ulcer since receiving their last provision of the PDE5 inhibitor pharmaceutical composition,
whether the subject has developed a bleeding disorder since receiving their last provision of the PDE5 inhibitor pharmaceutical composition,
whether the subject has developed an abnormal genital shape since receiving their last provision of the PDE5 inhibitor pharmaceutical composition,
whether the subject has developed a blood cell disorder since receiving their last provision of the PDE5 inhibitor pharmaceutical composition, and
whether the subject has starting taking a medication that interacts with the PDE5 inhibitor pharmaceutical composition since receiving their last provision of the PDE5 inhibitor pharmaceutical composition;
(ii) running all or a portion of the second plurality of survey results against a third plurality of filters of the first category class, wherein, when a respective filter in the third plurality of filters is fired, the subject is deemed not qualified for the PDE5 inhibitor pharmaceutical composition and the re-fulfillment process is terminated without delivery of the PDE5 inhibitor pharmaceutical composition to the subject, wherein the third plurality of filters comprises:
a second erectile dysfunction filter that is fired at least when the second plurality of survey results indicates that the subject does not have erectile dysfunction,
a second vasodilator filter that is fired at least when the second plurality of survey results indicates that the subject is taking a vasodilator composition comprising a nitrate or a nitrite,
a second guanylate cyclase stimulator filter that is fired at least when the second plurality of survey results indicates that the subject is taking a guanylate cyclase stimulator mediation,
a second PDE5 inhibitor filter that is fired at least when the second plurality of survey results indicates that the subject is taking a PDE5 inhibitor pharmaceutical composition,
a sexual intercourse filter that is fired at least when the second plurality of survey results indicates that the subject has experienced a symptom of heart problems during sexual intercourse since receiving their last provision of the PDE5 inhibitor pharmaceutical composition,
a second priapism filter that is fired at least when the second plurality of survey results indicates that the subject has had priapism since receiving their last provision of the PDE5 inhibitor pharmaceutical composition, and
a sensory deterioration filter that is fired at least when the second plurality of survey results indicates that the subject has experienced a sudden vision loss or sudden hearing loss since receiving their last provision of PDE5 inhibitor pharmaceutical composition;

(iii) running all or a portion of the second plurality of survey results against a fourth plurality of filters of the second category class, wherein, when a respective filter in the fourth plurality of filters is fired, the subject is provided with a warning corresponding to the respective filter, and wherein the fourth plurality of filters comprises:

a second heart problem filter that is fired at least when the second plurality of survey results indicates that the subject has developed a heart problem since receiving their last provision of the PDE5 inhibitor pharmaceutical composition, a second blood pressure filter that this fired at least when the second plurality of survey results indicates that the subject has developed either (i) low blood pressure, or (ii) uncontrolled high blood pressure, a second stroke filter that is fired at least when the second plurality of survey results indicates that the subject has had a stroke since receiving their last provision of the PDE5 inhibitor pharmaceutical composition, a second liver disease filter that is fired at least when the second plurality of survey results indicates that the subject has developed liver disease since receiving their last provision of the PDE5 inhibitor pharmaceutical composition, a second kidney disease filter that is fired at least when the second plurality of survey results indicates that the subject has developed a kidney problem since receiving their last provision of the PDE5 inhibitor pharmaceutical composition, a second retinitis pigmentosa filter that is fired at least when the second plurality of survey results indicates that the subject has been diagnosed with retinitis pigmentosa since receiving their last provision of the PDE5 inhibitor pharmaceutical composition, a second stomach ulcer filter that is fired at least when the second plurality of survey results indicates that the subject has developed a stomach ulcer since receiving their last provision of the PDE5 inhibitor pharmaceutical composition, a second bleeding problem filter that is fired at least when the second plurality of survey results indicates that the subject has developed a bleeding disorder since receiving their last provision of the PDE5 inhibitor pharmaceutical composition, a second genital abnormality filter that is fired at least when the second plurality of survey results indicates that the subject has developed an abnormal genital shape since receiving their last provision of the PDE5 inhibitor pharmaceutical composition, a second blood cell disorder filter that is fired at least when the second plurality of survey results indicates that the subject has developed a blood disorder selected from the group consisting of sickle cell anemia, multiple myeloma, and leukemia, since receiving their last provision of the PDE5 inhibitor pharmaceutical composition, and a second drug interaction filter that is fired at least when the second plurality of survey results indicates that the subject has started taking a medication that interacts with the PDE5 inhibitor pharmaceutical composition since receiving their last provision of the PDE5 inhibitor pharmaceutical composition;

(iv) obtaining acknowledgment from the subject for the warning issued to the subject by any filter in the fourth plurality of filters; and (v) proceeding with the re-fulfillment process when (a) the re-fulfillment process is not already terminated by the firing of a filter in the third plurality of filters and (b) the subject has acknowledged each warning associated with each filter in the fourth plurality of filters that was fired, wherein the re-fulfillment process further comprises:

storing an indication in a subject profile of a re-order for the PDE5 inhibitor pharmaceutical composition, communicating the over-the-counter drug facts label for PDE5 inhibitor pharmaceutical composition to the subject, and authorizing, upon confirmation from the subject that the over-the-counter drug facts label has been received and read, a re-order provision of the PDE5 inhibitor pharmaceutical composition to the subject.

47. The non-transitory computer readable storage medium of claim 46, wherein:

the second plurality of survey results further comprises whether the subject has experienced a side effect associated with the PDE5 inhibitor pharmaceutical composition since receiving their last provision of the PDE5 inhibitor pharmaceutical composition, and the fourth plurality of filters further comprises a side effect filter that is fired at least when the second plurality of survey results indicates that the subject has experienced, since receiving their last provision of the PDE5 inhibitor pharmaceutical composition, a side effect selected from the group consisting of headaches, abnormal vision, muscle pain, nausea, dizziness, and a skin rash.

48. The non-transitory computer readable storage medium of claim 46, wherein the re-fulfillment process further comprises, when a respective filter in the third plurality of filters or fourth plurality of filters is fired, storing a record associated with the firing of the respective filter in an adverse event profile comprising records of filter firing events associated with a plurality of subjects.

\* \* \* \* \*